US012644146B2

(12) United States Patent
Zheng

(10) Patent No.: US 12,644,146 B2
(45) Date of Patent: Jun. 2, 2026

(54) SINGLE-STRANDED END PRESERVING ADAPTORS

(71) Applicant: Canal Biosciences, INC, Lowell, MA (US)

(72) Inventor: Yu Zheng, Lexington, MA (US)

(73) Assignee: Canal Biosciences, Inc., Lowell, MA (US)

( * ) Notice: Subject to any disclaimer, the term of this patent is extended or adjusted under 35 U.S.C. 154(b) by 0 days.

(21) Appl. No.: 19/060,201

(22) Filed: Feb. 21, 2025

(65) Prior Publication Data

US 2025/0297301 A1     Sep. 25, 2025

Related U.S. Application Data

(60) Provisional application No. 63/556,538, filed on Feb. 22, 2024.

(51) Int. Cl.
C12N 9/22          (2006.01)
C12N 9/00          (2006.01)
(Continued)

(52) U.S. Cl.
CPC .............. C12Q 1/6806 (2013.01); C12N 9/22 (2013.01); C12N 9/2497 (2013.01); C12N 9/93 (2013.01);
(Continued)

(58) Field of Classification Search
None
See application file for complete search history.

(56) References Cited

U.S. PATENT DOCUMENTS

| | | |
|---|---|---|
| 5,695,934 A | 12/1997 | Brenner |
| 5,714,330 A | 2/1998 | Brenner et al. |

(Continued)

FOREIGN PATENT DOCUMENTS

| | | |
|---|---|---|
| EP | 3430154 B1 | 11/2020 |
| WO | WO-2000018957 A1 | 4/2000 |

(Continued)

OTHER PUBLICATIONS

Wang et al. (Mutational Analysis of Bacteriophage T4 RNA Ligase 1: Different Functional Groups Are Required for the Nucleotidyl Transfer and Phosphodiester Bond Formation Steps of the Ligation Reaction, JBC, 2003 (Year: 2003).*
(Continued)

*Primary Examiner* — Heather Calamita
*Assistant Examiner* — Elizabeth Rose Lafave
(74) *Attorney, Agent, or Firm* — Jason R. Bond; Casimir Jones, S.C.

(57) ABSTRACT

Provided herein are compositions, kits, systems, and methods employing single-stranded end-preserving adaptors. Such single-stranded adaptors are attached to DNA duplex molecules while preserving original 5' or 3' single-strand protruding ends (e.g., present in cell-free DNA) by attaching such adapters to 3' ends the DNA duplex molecules using a single strand ligase that has step 3 ligase activity, but not step 2 adenylyl transfer activity, and attaching such adapters to 5' ends of the DNA duplex molecules using a ligase enzyme (e.g., a circligase), thereby forming loop-like structures on one or each end of the DNA duplex molecules. In further embodiments, the loop-like structures are cleaved (e.g., by an endonuclease) as the single-stranded adapters have a cleavable portion, thereby generating a two-part adapter on one or both ends of the DNA duplex molecules that pre- (Continued)

serves the initial 5' or 3' single-strand protruding ends, along with any methylation present.

17 Claims, 23 Drawing Sheets

Specification includes a Sequence Listing.

(51) Int. Cl.

| | |
|---|---|
| *C12N 9/24* | (2006.01) |
| *C12Q 1/6806* | (2018.01) |
| *C12Q 1/6855* | (2018.01) |
| *C12Q 1/6869* | (2018.01) |
| *C12N 9/12* | (2006.01) |
| *C12Q 1/68* | (2018.01) |

(52) U.S. Cl.
CPC ......... *C12Q 1/6855* (2013.01); *C12Q 1/6869* (2013.01); *C12Q 2521/501* (2013.01); *C12Q 2525/186* (2013.01); *C12Q 2525/191* (2013.01); *C12Q 2531/113* (2013.01); *C12Q 2535/122* (2013.01); *C12Q 2563/179* (2013.01); *C12Y 301/21007* (2013.01); *C12Y 302/02027* (2013.01); *C12Y 605/01* (2013.01)

(56) References Cited

U.S. PATENT DOCUMENTS

| | | | |
|---|---|---|---|
| 5,750,341 | A | 5/1998 | Macevicz |
| 5,912,148 | A | 6/1999 | Eggerding |
| 6,130,073 | A | 10/2000 | Eggerding |
| 6,210,891 | B1 | 4/2001 | Uhlen et al. |
| 6,258,568 | B1 | 7/2001 | Nyren |
| 6,306,597 | B1 | 10/2001 | Macevicz |
| 6,432,360 | B1 | 8/2002 | Church |
| 6,485,944 | B1 | 11/2002 | Church et al. |
| 6,511,803 | B1 | 1/2003 | Church et al. |
| 6,787,308 | B2 | 9/2004 | Balasubramanian et al. |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,282,337 | B1 | 10/2007 | Harris |
| 7,329,492 | B2 | 2/2008 | Hardin et al. |
| 7,482,120 | B2 | 1/2009 | Buzby |
| 7,501,245 | B2 | 3/2009 | Quake et al. |
| 7,668,697 | B2 | 2/2010 | Volkov et al. |
| 8,383,345 | B2 | 2/2013 | Shendure et al. |
| 8,532,930 | B2 | 9/2013 | Rabinowitz et al. |
| 8,697,408 | B2 | 4/2014 | Kucera et al. |
| 9,598,731 | B2 | 3/2017 | Talasaz |
| 9,639,657 | B2 | 5/2017 | Rabinowitz et al. |
| 9,752,188 | B2 | 9/2017 | Schmitt et al. |
| 9,902,992 | B2 | 2/2018 | Talasaz et al. |
| 10,011,870 | B2 | 7/2018 | Zimmermann et al. |
| 10,570,451 | B2 | 2/2020 | Salk et al. |
| 10,801,063 | B2 | 10/2020 | Eltoukhy et al. |
| 10,876,172 | B2 | 12/2020 | Talasaz |
| 11,091,797 | B2 | 8/2021 | Talasaz et al. |
| 11,479,807 | B2 | 10/2022 | Kennedy et al. |
| 2005/0130173 | A1 | 6/2005 | Leamon et al. |
| 2008/0241951 | A1 | 10/2008 | Battulga et al. |
| 2009/0026082 | A1 | 1/2009 | Rothberg et al. |
| 2009/0035777 | A1 | 2/2009 | Kokoris et al. |
| 2009/0127589 | A1 | 5/2009 | Rothberg et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2012/0238738 | A1 | 9/2012 | Hendrickson |
| 2012/0244525 | A1 | 9/2012 | Hendrickson |
| 2015/0031026 | A1 | 1/2015 | Hendricks et al. |
| 2015/0218608 | A1 | 8/2015 | Lohman et al. |
| 2019/0062827 | A1* | 2/2019 | Zheng .................... C12Q 1/686 |
| 2021/0054366 | A1 | 2/2021 | Harkins Kincaid et al. |
| 2022/0010353 | A1 | 1/2022 | Lo et al. |
| 2022/0356467 | A1 | 11/2022 | Luthra et al. |
| 2025/0283134 | A1* | 9/2025 | Ding .................... C12Y 605/01 |

FOREIGN PATENT DOCUMENTS

| | | | |
|---|---|---|---|
| WO | WO-2006084132 A2 | 8/2006 | |
| WO | WO-2010094040 A1 | 8/2010 | |
| WO | WO-2017160788 A2 | 9/2017 | |
| WO | WO-2020206143 A1 * | 10/2020 | ........... C12Q 1/6869 |

OTHER PUBLICATIONS

Adessi C., et al., "Solid Phase DNA Amplification: Characterisation of Primer Attachment and Amplification Mechanisms", Nucleic Acids Research, Oct. 15, 2000, vol. 28, No. 20, e87, pp. 1-8.

Astier Y., et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," Journal of the American Chemical Society, Feb. 8, 2006, vol. 128, No. 5, pp. 1705-1710.

Bae J.H., et al., "Single Duplex DNA Sequencing with CODEC Detects Mutations with High Sensitivity", Nature Genetics, May 2023, vol. 55, No. 5, pp. 871-879 (26 Pages).

Bennett S.T., et al., "Toward the $1000 Human Genome," Pharmacogenomics, Jun. 2005, vol. 6, No. 4, pp. 373-382.

Birren B., et al., "Genome Analysis: Analyzing DNA", vol. 1, Cold Spring Harbor, N.Y, 1997, TOC only, 13 pages.

Bolger A.M., et al., "Trimmomatic: A Flexible Trimmer for Illumina Sequence Data", Bioinformatics, Aug. 1, 2014, vol. 30, No. 15, pp. 2114-2120, DOI:10.1093/bioinformatics/btu170, XP055862121.

Brenner S., et al., "Gene Expression Analysis by Massively Parallel Signature Sequencing (MPSS) on Microbead Arrays", Nature Biotechnology, Jun. 2000, vol. 18, No. 6, pp. 630-634.

Chakravarty A.K., et al., "The Sequential 2',3'-Cyclic Phosphodiesterase and 3'-Phosphate/5'-OH Ligation Steps of the RtcB RNA Splicing Pathway are GTP-dependent", Nucleic Acids Research, Sep. 2012, vol. 40, No. 17, pp. 8558-8567.

Chen F., et al., "Reconstructed Evolutionary Adaptive Paths Give Polymerases Accepting Reversible Terminators for Sequencing and SNP Detection", Proceedings of the National Academy of Sciences USA, Feb. 2, 2010, vol. 107, No. 5, pp. 1948-1953.

Clark J.M., "Novel Non-templated Nucleotide Addition Reactions Catalyzed by Procaryotic and Eucaryotic DNA Polymerases", Nucleic Acids Research, 1988, vol. 16, No. 20, pp. 9677-9686.

Costello M., et al., "Discovery and Characterization of Artifactual Mutations in Deep Coverage Targeted Capture Sequencing Data Due to Oxidative DNA Damage During Sample Preparation", Nucleic Acids Research, Apr. 1, 2013, vol. 41, No. 6, e67, 12 Pages.

Das U., et al., "Rewriting the rules for end joining via enzymatic splicing of DNA 3-PO4 and 5-OH ends", Proceedings of the National Academy of Sciences of the United States of America, Dec. 17, 2013, vol. 110, No. 51, pp. 20437-20442.

Desai K.K., et al., "Coevolution of RtcB and Archease Created a Multiple-turnover RNA Ligase", RNA, Nov. 2015, vol. 21, No. 11, pp. 1866-1872.

Ding S.C., et al., "Jagged Ends on Multinucleosomal Cell-Free DNA Serve as a Biomarker for Nuclease Activity and Systemic Lupus Erythematosus", Clinical Chemistry, vol. 68, No. 7, 2022, pp. 917-926.

Duan S., et al., "Purification and Enzymatic Characterization of the RNA Ligase Rtcb from Thermus Thermophilus", Biotechnol Lett, Sep. 2019, vol. 41, (8-9), pp. 1051-1057.

Fulcrumgenomics: fgbio. Retrieved from https://github.com/fulcrumgenomics/fgbio, On Dec. 1, 2025. 8 pages.

Gansauge M-T., et al., "Single-stranded DNA Library Preparation for the Sequencing of Ancient or Damaged DNA", Nature Protocols, vol. 8, No. 4, Apr. 2013, pp. 737-748.

(56) References Cited

OTHER PUBLICATIONS

Gregory T., et al., "Characterization and Mitigation of Fragmentation Enzyme-induced Dual Stranded Artifacts", NAR Genom Bioinform, Dec. 2020, vol. 2, No. 4, Iqaa070, 7 Pages.

Harkins K.M., et al., "A Novel NGS Library Preparation Method to Characterize Native Termini of Fragmented DNA", Nucleic Acids Research, Feb. 29, 2020, vol. 48, No. 8, 13 Pages.

Huang Q., et al., "Origin of Iodine Preferential Attack at Sulfur in Phosphorothioate and Subsequent P—O or P—S Bond Dissociation", Proceedings of the National Academy of Sciences of the United States of America, Apr. 26, 2022, vol. 119, No. 17, e2119032119, pp. 1-9.

International Search Report and Written Opinion for PCT/US2025/016835, dated Sep. 2, 2025, 26 pages.

Jacewicz A., et al., "Structures of RNA Ligase RtcB in Complexes with Divalent Cations and GTP", RNA, vol. 28, No. 11, Nov. 2022, pp. 1509-1518.

Jiang P., et al., "Detection and Characterization of Jagged Ends of Double-Stranded DNA in Plasma", Genome Research, Aug. 2020, vol. 30, No. 8, pp. 1144-1153.

Jiang P., et al., "Lengthening and Shortening of Plasma DNA in Hepatocellular Carcinoma Patients," Proceedings of the National Academy of Sciences of the United States of America, Mar. 17, 2015, vol. 112, No. 11, pp. E1317-E1325.

Lanman R.B., et al., "Analytical and Clinical Validation of a Digital Sequencing Panel for Quantitative, Highly Accurate Evaluation of Cell-Free Circulating Tumor DNA", PLoS One, Oct. 16, 2015, vol. 10, No. 10, e0140712, pp. 1-27.

Lau N.C., et al., "An Abundant Class of Tiny RNAs with Probable Regulatory Roles in Caenorhabditis elegans", Science, Oct. 26, 2001, vol. 294, No. 5543, pp. 858-862.

Lehman I.R., "DNA Ligase: Structure, Mechanism, and Function", Science, Nov. 29, 1974, vol. 186, No. 4166, pp. 790-797.

Li H., et al, "Fast and Accurate Short Read Alignment With Burrows-Wheeler Transform," Bioinformatics, Jul. 15, 2009, vol. 25, No. 14, pp. 1754-1760.

Li H., et al., "The Sequence Alignment/Map Format and SAMtools," Bioinformatics, Aug. 15, 2009, vol. 25, No. 16, pp. 2078-2079.

Lindahl T., et al., "Mammalian DNA Ligases", Annual Review of Biochemistry, 1992, vol. 61, pp. 251-281.

Liu Y., et al., "Bisulfite-free Direct Detection of 5-Methylcytosine and 5-Hydroxymethylcytosine at Base Resolution," Nature Biotechnology, 2019, vol. 37, pp. 424-429 (11 pages), doi: 10.1038/s41587-019-0041-2, XP055737047.

Lohman G.J.S., et al., "Kinetic Characterization of Single Strand Break Ligation in Duplex DNA by T4 Dna Ligase", Journal of Biological Chemistry, Dec. 23, 2011, vol. 286, No. 51, pp. 44187-44196.

Maclean D., et al., "Application of Next-generation Sequencing Technologies to Microbial Genetics", Nature Reviews Microbiology, Apr. 2009, vol. 7, pp. 287-296.

Magnuson V.L., et al., Substrate Nucleotide-determined Non-templated Addition of Adenine by Taq DNA Polymerase: implications for PCR-Based Genotyping and Cloning, Biotechniques, Oct. 1996, vol. 21, No. 4, pp. 700-709 (11 Pages).

Margulies M., et al., "Genome Sequencing in Microfabricated High-density Picolitre Reactors", Nature, Sep. 15, 2005, vol. 437, No. 7057, pp. 376-380 (14 Pages).

Mitra R.D., et al., "Fluorescent in Situ Sequencing on Polymerase Colonies," Analytical Biochemistry, Sep. 1, 2003, vol. 320, No. 1, pp. 55-65.

Morozova O., et al., "Applications of Next-generation Sequencing Technologies in Functional Genomics", Genomics, Nov. 2008, vol. 92, No. 5, pp. 255-264.

New England Biolabs: "NEBNext for Illumina NGS Sample Preparation", 2017, 32 pages.

Pennisi E., "Semiconductors Inspire New Sequencing Technologies," Genomics, Science, Mar. 5, 2010, vol. 327, No. 5970, pp. 1190.

Phelps C., et al., "Single-Molecule FRET and Linear Dichroism Studies of DNA Breathing and Helicase Binding at Replication Fork Junctions", Proceedings of the National Academy of Sciences of the United States of America, Oct. 22, 2013, vol. 110, No. 43, pp. 17320-17325.

Picard: Build Passing, Retrieved on https://followedbybroadinstitute.github.io/picard/ on Dec. 1, 2025, 5 Pages.

Picelli S., et al., "Tn5 Transposase and Tagmentation Procedures for Massively Scaled Sequencing Projects," Genome Research, Dec. 2014, vol. 24, No. 12, pp. 2033-2040.

Rossi R., et al., "Functional Characterization of the T4 DNA Ligase: a New Insight into the Mechanism of Action", Nucleic Acids Research, vol. 25, No. 11, Jun. 1, 1997, pp. 2106-2113.

Ruparel H., et al., "Design and Synthesis of a 3'-O-allyl Photocleavable Fluorescent Nucleotide as a Reversible Terminator for DNA Sequencing by Synthesis", Proceedings of the National Academy of Sciences of the United States of America, Apr. 26, 2005, vol. 102, No. 17, pp. 5932-5937.

Schmitt M.W., et al., "Detection of Ultra-rare Mutations by Next-generation Sequencing", Proceedings of the National Academy of Sciences of the United States of America, vol. 109, No. 36, Sep. 4, 2012, pp. 14508 14513.

Sgaramella V., et al., "Studies on polynucleotides, CXVI. A further study of the T4 ligase-catalyzed joining of DNA at base-paired ends", Journal of Molecular Biology, vol. 72, No. 3, Dec. 30, 1972, pp. 493-502.

Shendure J., et al., "Accurate Multiplex Polony Sequencing of an Evolved Bacterial Genome", Science, Sep. 9, 2005, vol. 309, No. 5741, pp. 1728-1732, 6 Pages.

Shuman S., "DNA Ligases: Progress and Prospects", Journal of Biological Chemistry, Jun. 26, 2009, vol. 284, No. 26, pp. 17365-17369 (6 Pages).

Shuman S., et al., "RNA Capping Enzyme and DNA ligase: A Superfamily of Covalent Nucleotidyl Transferases", Molecular Microbiology, vol. 17, No. 3, Aug. 1995, pp. 405-410.

Snyder M.W., et al., "Cell-free DNA Comprises an in Vivo Nucleosome Footprint That Informs its Tissues-of-origin", Cell, Jan. 14, 2016, vol. 164, pp. 57-68 (24 Pages).

Sriskanda V., et al., "Chlorella virus DNA ligase: Nick Recognition and Mutational Analysis", Nucleic Acids Research, vol. 26, No. 2, Jan. 15, 1998, pp. 525-531.

Tanaka N., et al., "RtcB is the RNA Ligase Component of an *Escherichia coli* RNA Repair Operon", The Journal of Biological Chemistry, Mar. 11, 2011, vol. 286, No. 10, pp. 7727-7731.

Thierry A.R., "Circulating DNA Fragmentomics and Cancer Screening", Cell Genomics, Jan. 11, 2023, vol. 3, No. 1, 100242, 15 Pages.

Tomkinson A.E., et al., "DNA Ligases: Structure, Reaction Mechanism, and Function", Chemical Reviews, Feb. 2006, vol. 106, No. 2, pp. 687-699.

Torchia C., et al., "Archaeal RNA Ligase Is a Homodimeric Protein That Catalyzes Intramolecular Ligation of Single-stranded RNA and DNA", Nucleic Acids Research, vol. 36, No. 19, Oct. 1, 2008, pp. 6218-6227.

Troll C.J., et al., "A Ligation-based Single-stranded Library Preparation Method to Analyze Cell-free DNA and Synthetic Oligos", BMC Genomics, Dec. 27, 2019, vol. 20, No. 1, 1023, 14 Pages.

Voelkerding K.V., et al., "Next-Generation Sequencing: From Basic Research to Diagnostics", Clinical Chemistry, Apr. 2009, vol. 55, No. 4, pp. 641-658.

Wang Y., et al., "Human DNA Ligase IV and the Ligase IV/XRCC4 Complex: Analysis of Nick Ligation Fidelity", Biochemistry, May 1, 2007, vol. 46, pp. 4962-4976.

Weiss B., et al., "Enzymatic Breakage and Joining of Deoxyribonucleic Acid, I. Repair of Single-strand Breaks in DNA by an Enzyme System from *Escherichia coli* Infected with T4 Bacteriophage", Proceedings of the National Academy of Sciences of the United States of America, Apr. 1967, vol. 57, No. 4, pp. 1021-1028.

Wu W., et al., "Termination of DNA Synthesis by N6-Alkylated, not 3'-O-Alkylated, Photocleavable 2'-Deoxyadenosine Triphosphates", Nucleic Acids Research, Sep. 18, 2007, vol. 35, No. 19, pp. 6339-6349.

(56) References Cited

OTHER PUBLICATIONS

Xiong K., et al., "Duplex-repair Enables Highly Accurate Sequencing, Despite DNA Damage", Nucleic Acids Research, Jan. 11, 2022, vol. 50, No. 1, e1, 10 Pages.
Yin S., et al., "Structure-Function Analysis of T4 RNA Ligase 2", Journal of Biological Chemistry, May 16, 2003, vol. 278, No. 20, pp. 17601-17608.
Zhelkovsky A.M., et al., "Structure-Function Analysis of Methanobacterium Thermoautotrophicum RNA Ligase—Engineering a Thermostable ATP Independent Enzyme", MC Molecular and Cell Biology, Jul. 18, 2012, vol. 13, No. 24, pp. 1-10.
Zheng Y., et al., "A Unique Family of Mrr-like Modification-dependent Restriction Endonucleases", Nucleic Acids Research, Sep. 2010, vol. 38, No. 16, pp. 5527-5534.
Zillig W., et al., "Hyperthermus Butylicus, a Hyperthermophilic Sulfur-reducing Archaebacterium That Ferments Peptides", Journal of Bacteriology, Jul. 1990, vol. 172, No. 7, pp. 3959-3965.

* cited by examiner

FIGURE 1A-C
A.
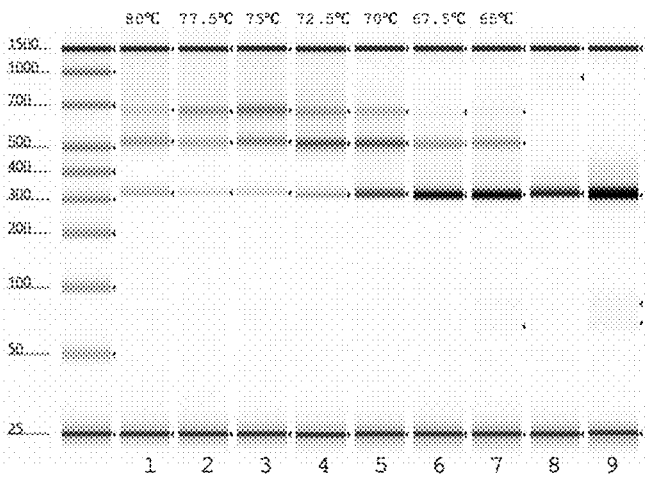
B.
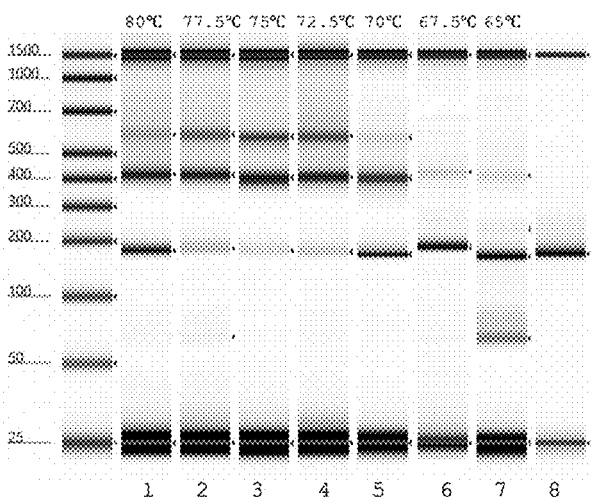
C.
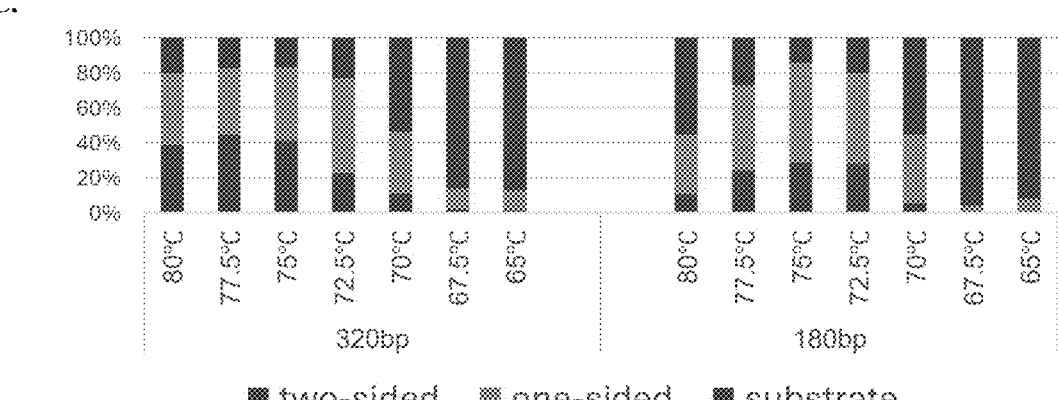

FIGURE 2A-C
A.
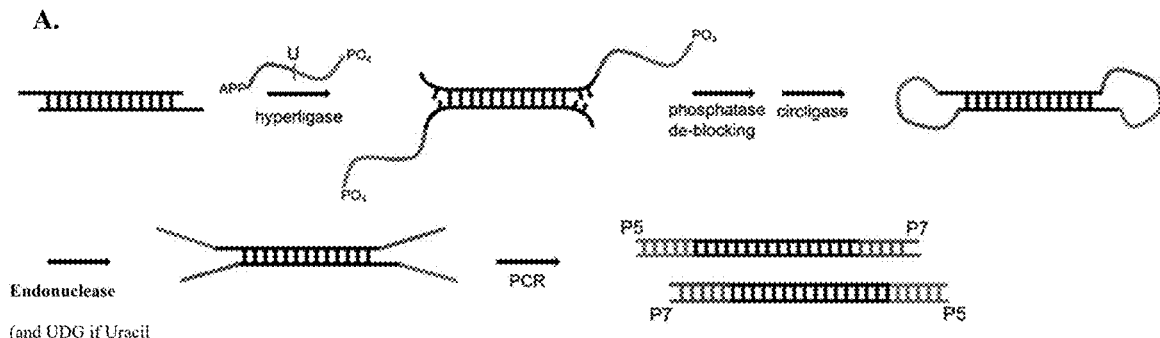
B.
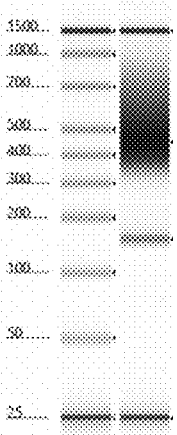
C.
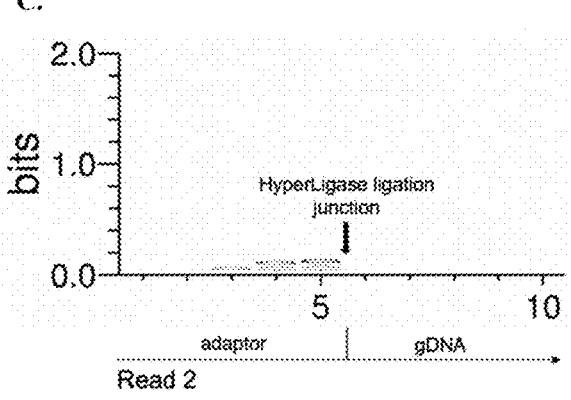
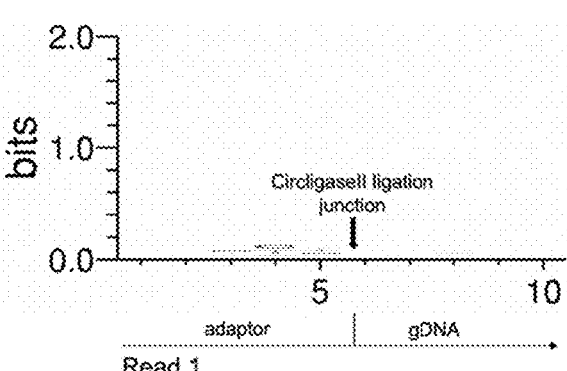

FIGURE 2D-E
D.
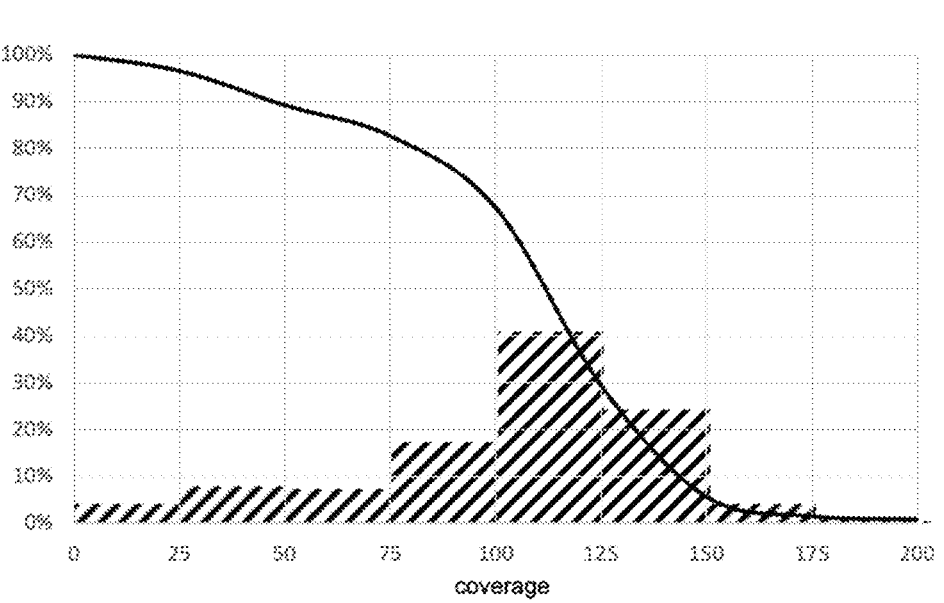
E.
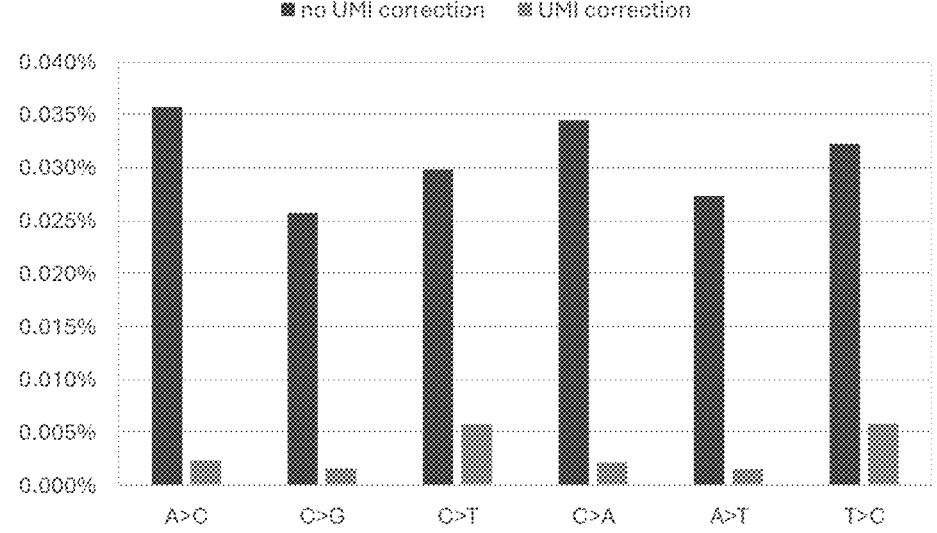

FIGURE 3A-B
A.
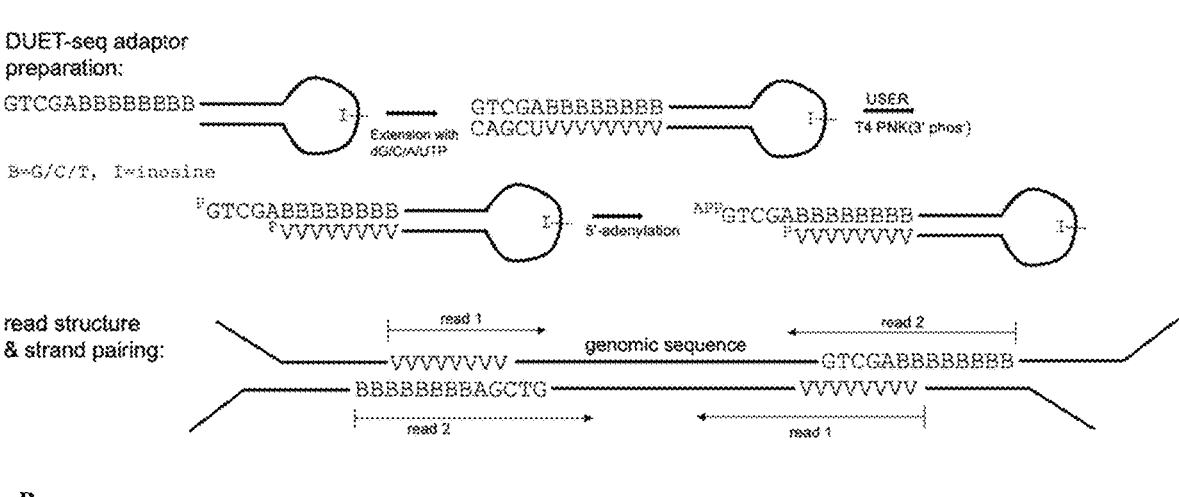
B.
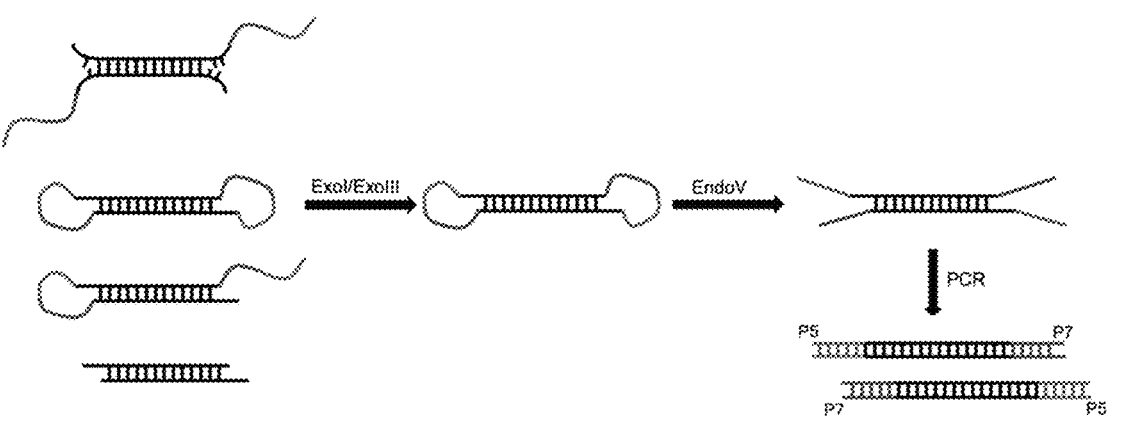

FIGURE 3C-D
C.
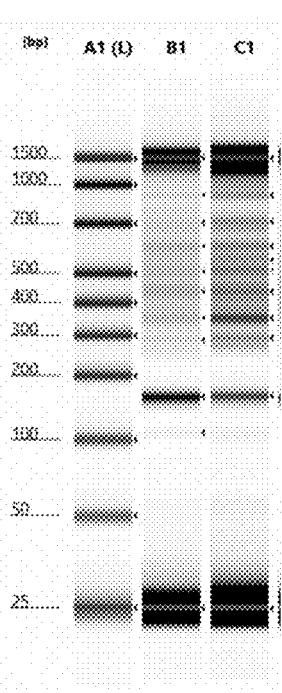
D.
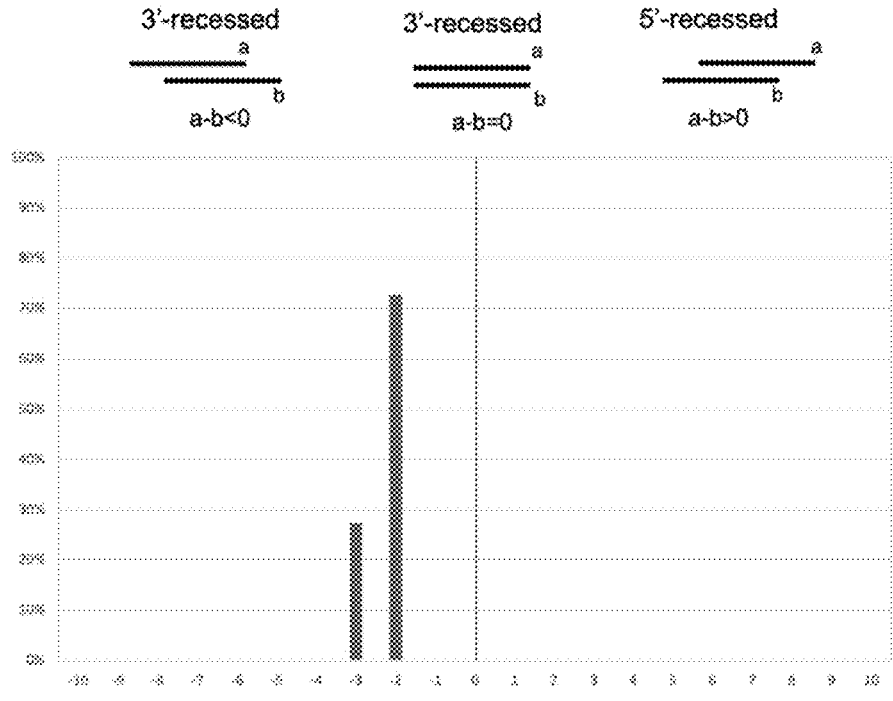

FIGURE 4A-B
A.
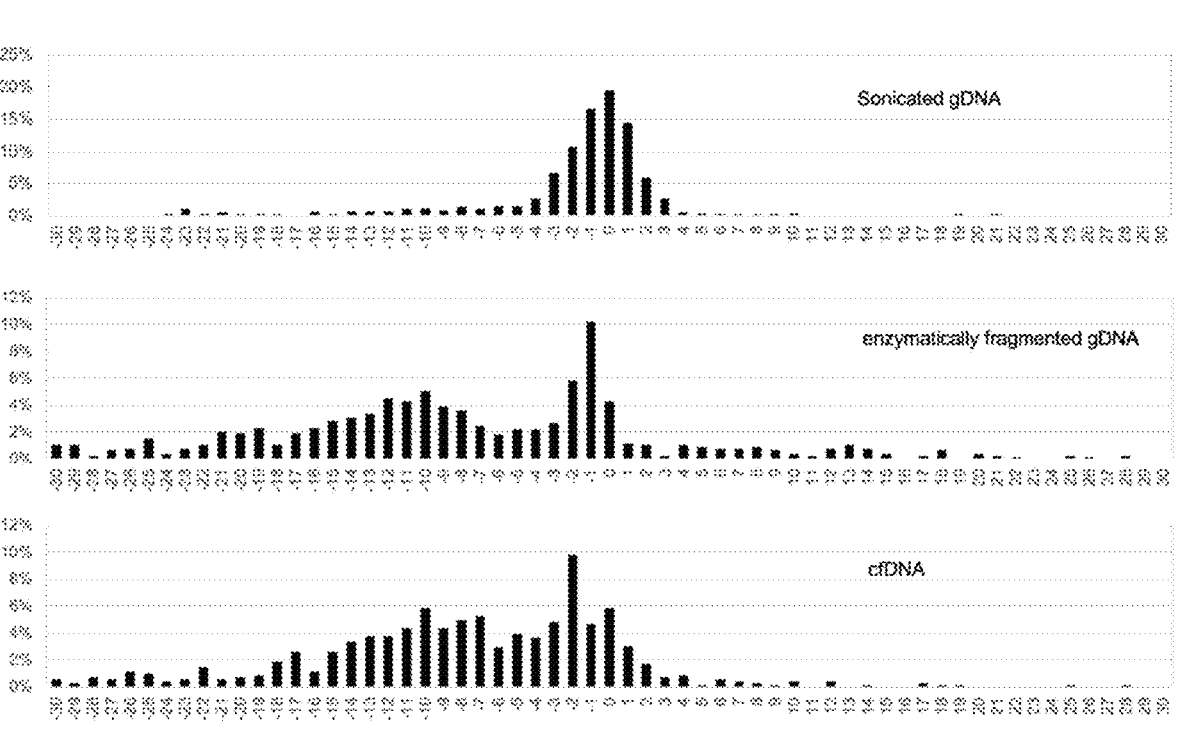
B.
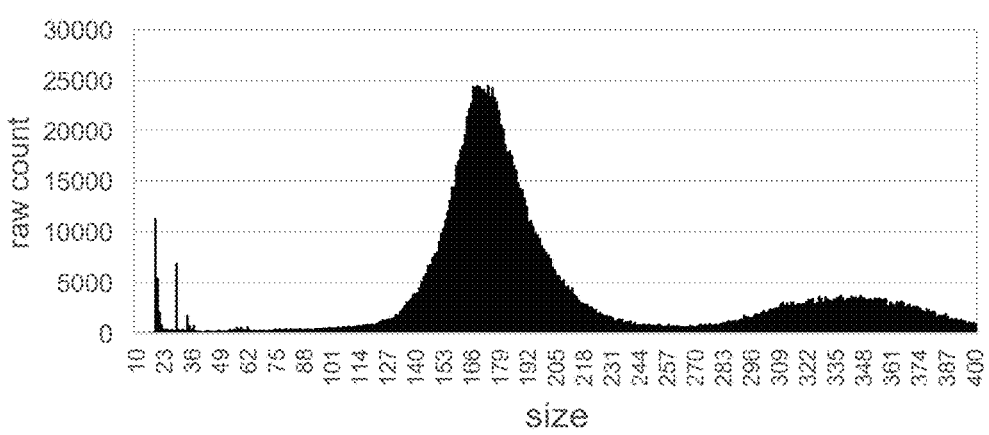

FIGURE 11A-F
A.
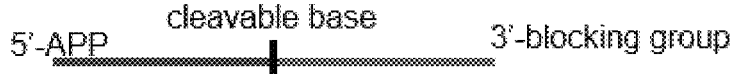
B.
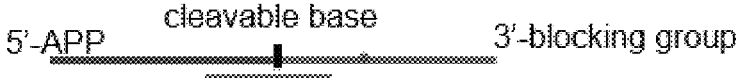
C.
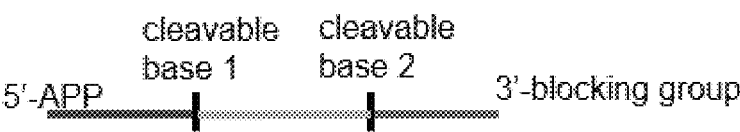
D.
cleavable    cleavable
base 1       base 2
5'-APP ──────┼───────────┼──────── 3'-blocking group
E.
5'-APP ──────────────── RNA    3'-blocking group
5'-APP ──────────────── RNA
F.
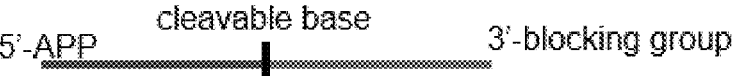

FIGURE 12A-B
A.
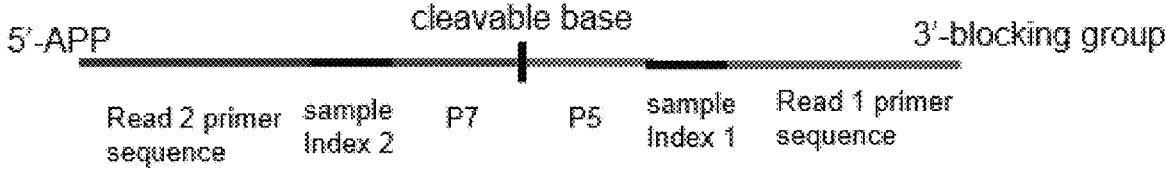
B.

FIGURE 13A-B
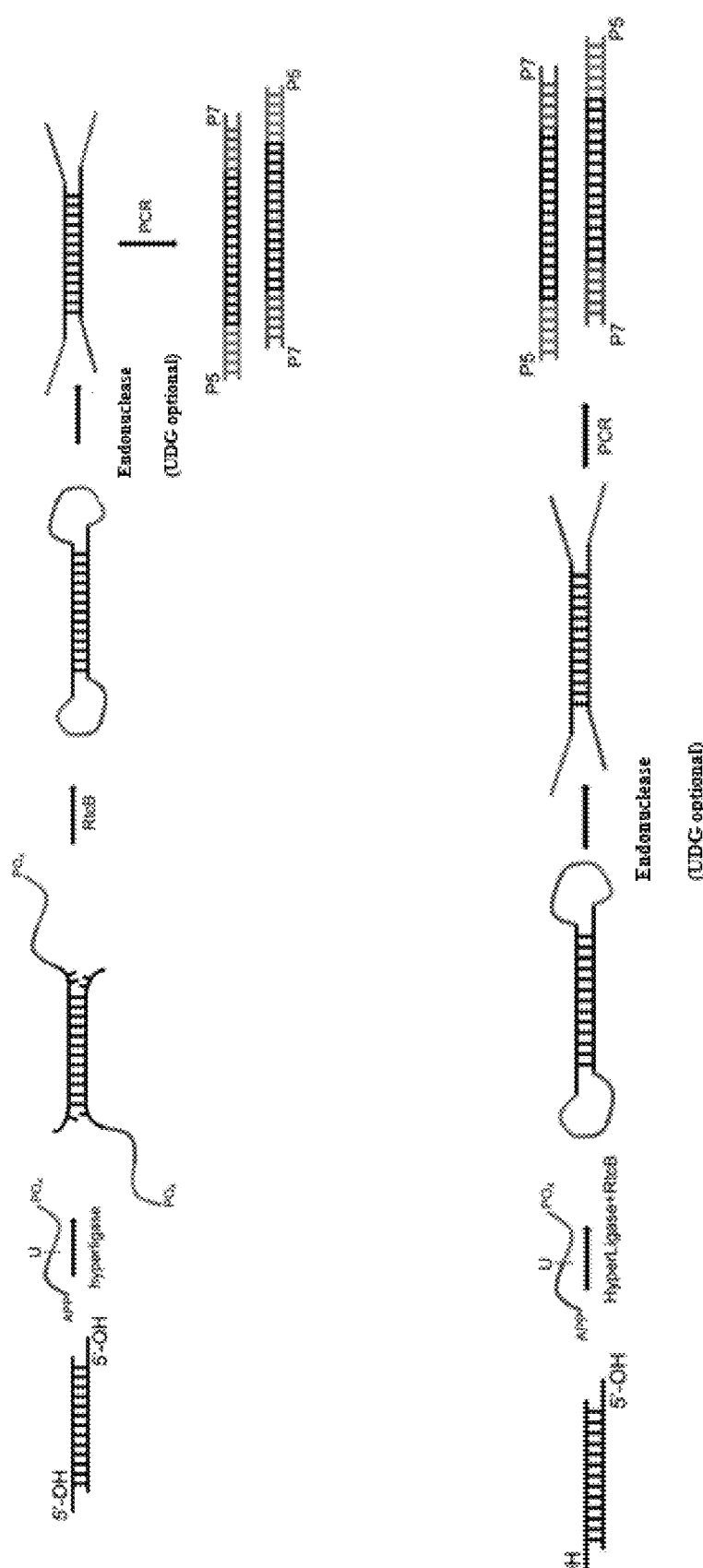

FIGURE 14A
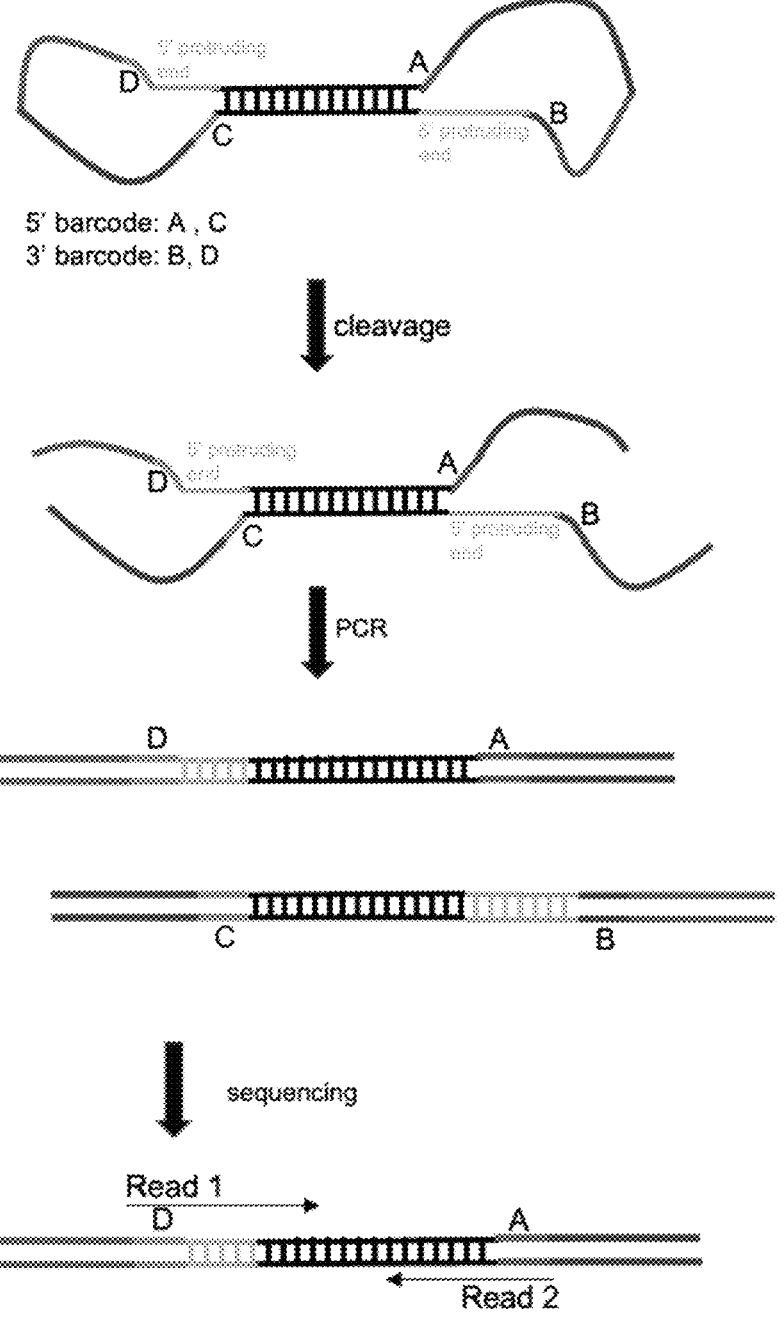
5' barcode: A , C
3' barcode: B, D
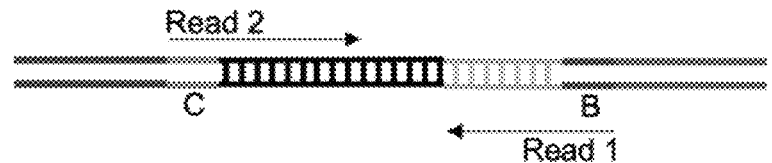

FIGURE 14B
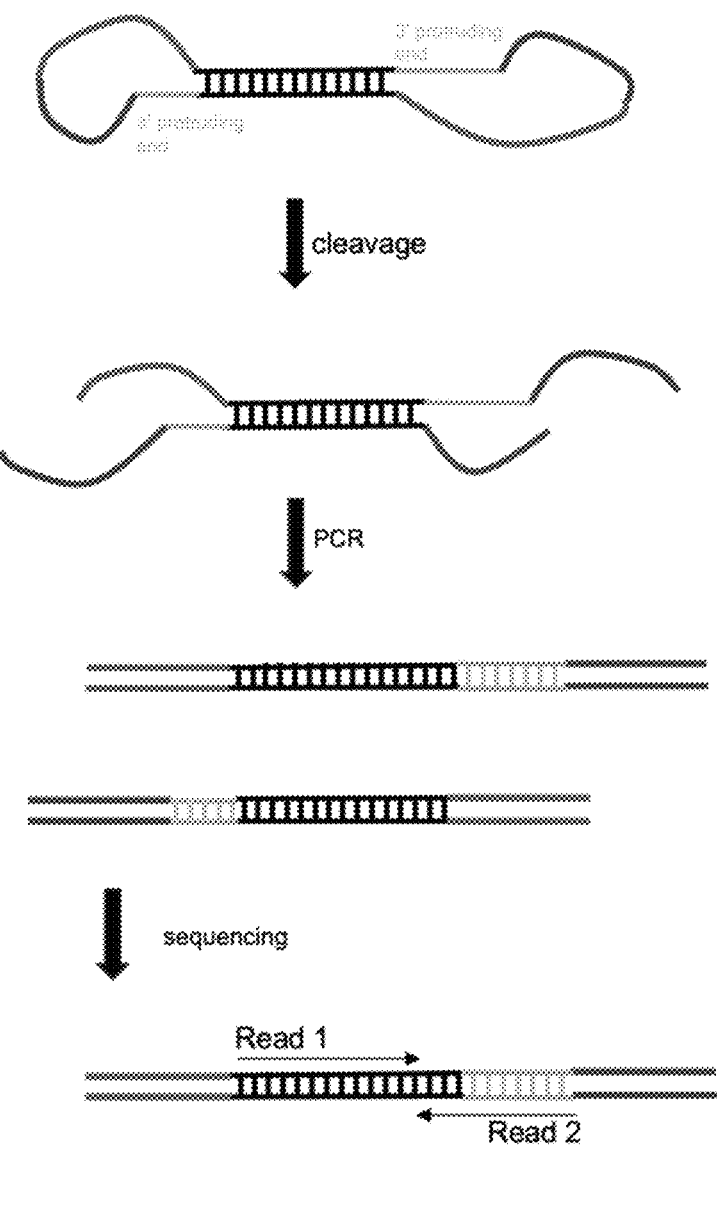
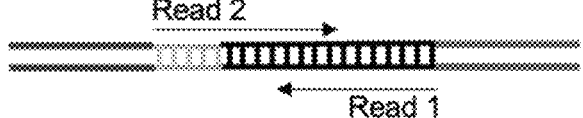

FIGURE 15A-B
A.
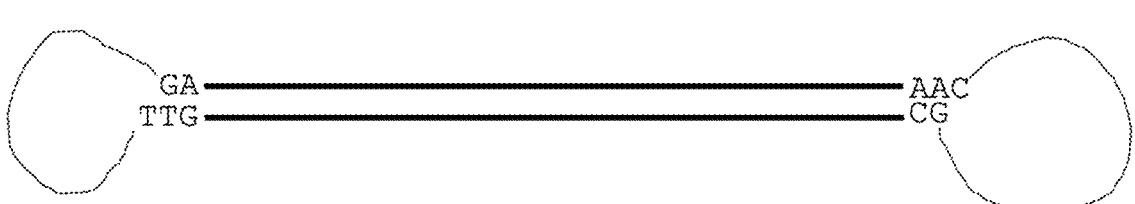
B.
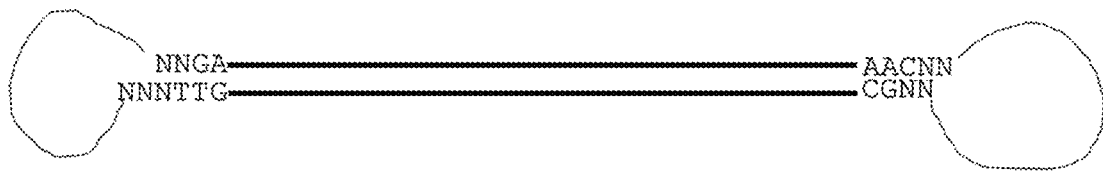

FIGURE 16A-B
A.
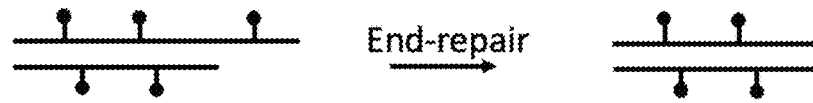
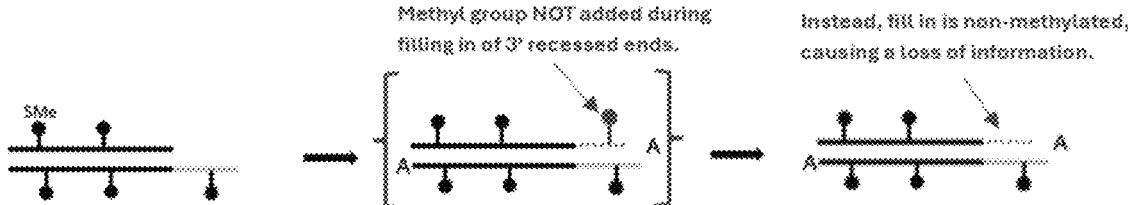
B.
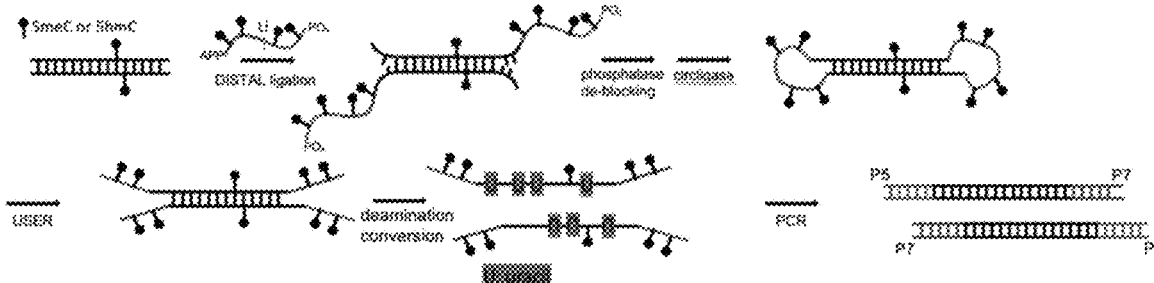

FIGURE 18A-B
A.
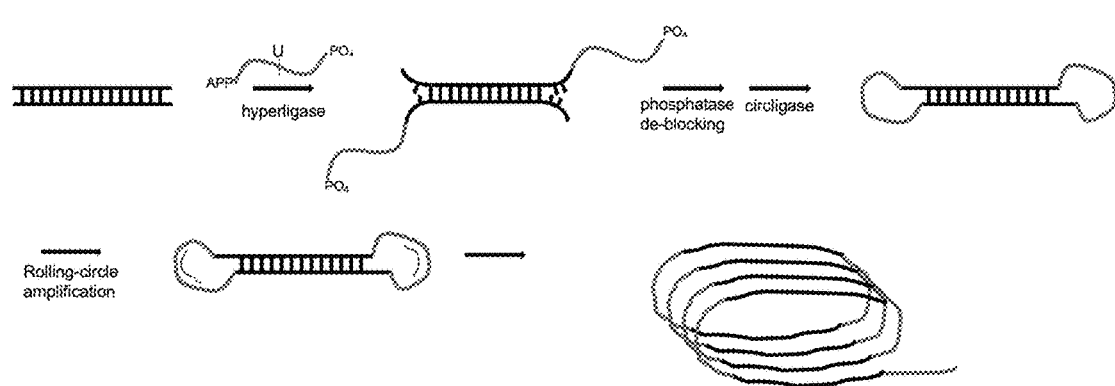
B.
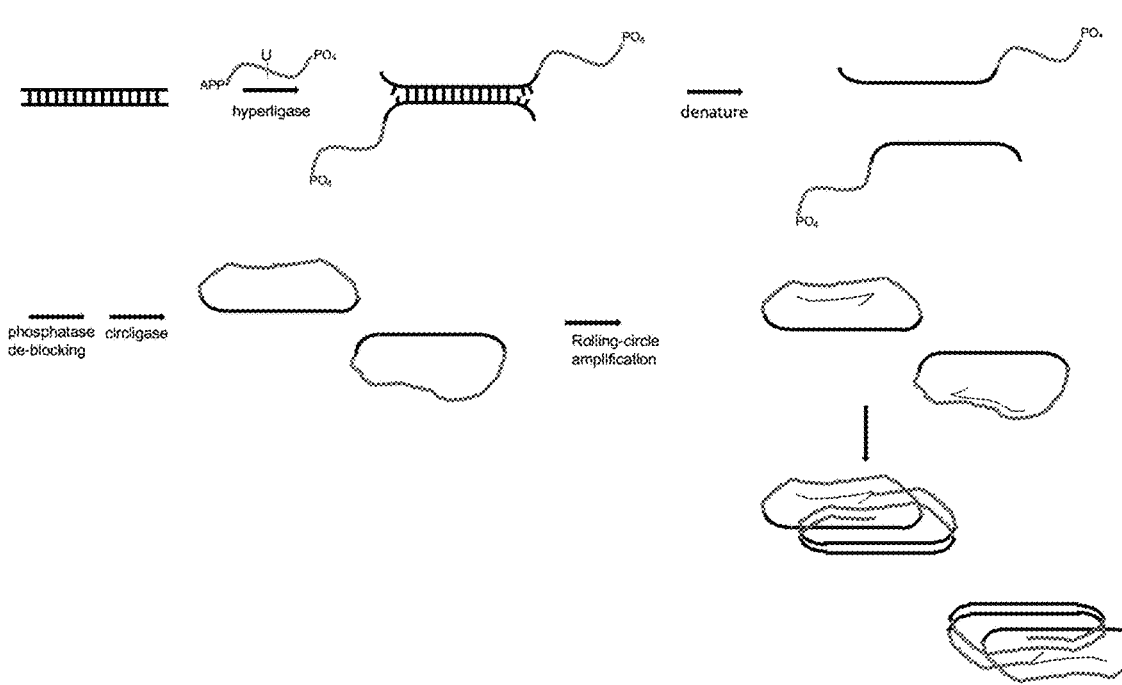

Read 1 sequencing primer (5APP)AGATCGGAAGAGCACACGTCTGAACTCCAGTCACUACACTCTTCCCTACACGACGCTCTTCCGATCT(3P)    SEQ ID NO:54

Read 2 sequencing primer

B.

(5APP)NNNNNNAGATCGGAAGAGCACACGTCTGAACTCCAGTCACUACACTCTTCCCTACACGACGCTCTTCCGATCTNNNNN(3P)    SEQ ID NO:55

C.

(5APP)(BARCODE1)AGATCGGAAGAGCACACGTCTGAACTCCAGTCACUACACTCTTCCCTACACGACGCTCTTCCGATCT(BARCODE2)(3P)    SEQ ID NO:54

D.

Read 2 sequencing primer     P7     P5     Read 1 sequencing primer (5APP)AGATCGGAAGAGCACACGTCTGAACTCCAGTCACATCTCGTATGCCGTCTTCTGCTTGAATGATACGGCGACCACCGAGATCTACACAGACTCTTTCCCTACACGACGCTCTTCCGATCT(3P)    SEQ ID NO:58

E.

Read 2 sequencing primer    i7 index     P7     P5    i5 index     Read 1 sequencing primer (5APP)AGATCGGAAGAGCACACGTCTGAACTCCAGTCAC(i7)ATCTCGTATGCCGTCTTCTGCTTGAATGATACGGCGACCACCGAGATCTACAC(i5)ACACTGTTTCCCTACACGACGCTCTTCCGATCT(3P)

SINGLE-STRANDED END PRESERVING ADAPTORS

The present application claims priority to U.S. Provisional application Ser. No. 63/556,538, filed Feb. 22, 2024, and which is herein incorporated by reference in its entirety.

FIELD

Provided herein are compositions, kits, systems, and methods employing single-stranded end-preserving adaptors. Such single-stranded adaptors are attached to DNA duplex molecules while preserving original 5' or 3' single-strand protruding ends (e.g., present in cell-free DNA) by attaching such adapters to 3's ends the DNA duplex molecules using a single strand ligase that has step 3 ligase activity, but not step 2 adenylyl transfer activity, and attaching such adapters to the 5' ends of the DNA duplex molecules using a ligase enzyme (e.g., a circligase), thereby forming loop-like structures on one or each end of the DNA duplex molecules. In further embodiments, the loop-like structures are cleaved (e.g., by an endonuclease) as the single-stranded adapters have a cleavable portion, thereby generating a two-part adapter on one or both ends of the DNA duplex molecules that preserves the initial 5' or 3' single-strand protruding ends (or blunt end(s)).

BACKGROUND

NGS (Next-generation sequencing) library preparation workflows are often composed of an end-repair and A-tailing step (ER/AT) on the fragmented DNA. During end repair (ER), 3'-single-strand protruding ends are filled in and 3'-protruding (i.e., 5'-single-strand protruding) ends are resected to form blunt-ended DNA duplexes. This is often catalyzed by the T4 DNA polymerase, which has both 5'-3' polymerase activity as well as 3'-5' exonuclease activity. During A-tailing (AT), Taq DNA polymerase or Klenow polymerase adds a non-templated A to the 3' ends of the DNA duplexes to facilitate the subsequent ligation with the T-overhang sequencing adaptors. The ER/AT step is necessary before the ligation step due to the biochemical substrate requirement of the T4 DNA ligase, which dictates ligation between two DNA duplex fragments.

There can be conceivable concerns associated with the conventional ER/AT process and its underlying chemistry. First, there are both "writing" (3'-single-strand protruding ends fill-in) and "erasing" (3'-protruding ends resection) done to the original DNA samples before they are amplified. The "writing" activity during ER/AT increases the likelihood of introducing replication errors, which can later be amplified and regarded as bona-fide mutations associated with the starting sample. As an example, it is observed that the polymerase-associated "writing" activity may create numerous sequencing artifacts due to its use for fragmentation (1). The "erasing," on the other hand, simply reduces sample input, leads to the fractional loss of the sequence information and can have a negative impact on the assay sensitivity for the genomic alteration discovery.

Second, it is discovered that the "writing" may not be limited to the ends. In fact, it was recently reported that a substantial level of DNA strand resynthesis may occur during the ER/AT step, oftentimes initiated from sites deep within the DNA duplexes (2). It is reported that "7-17% and 32-57% of interior 'duplex base pairs' from cell-free DNA and formalin-fixed tumor biopsies, respectively, could be resynthesized in vitro and potentially introduce false mutations" (2). In addition, for genomic assays aiming at mapping the epigenetic modifications of the bases, the synthesis and resynthesis during ER/AT will introduce confounding factors as the newly synthesized patches lack the biologically relevant epigenetic marks (3). As the result, resynthesis during ER/AT may dilute the biological epigenetic signals and results in underestimation of the modification levels (3).

Third, since the single strand overhangs of the starting DNA are destroyed after ER/AT, it is often hard to infer the original ends, especially for the 3'-ends, from the sequencing data. As such, the uncertainty of the 3'-end location may complicate signals inferred from the "fragmentomics" studies (4). As another example, by using duplex sequencing library preparation methods (5), where two strands originating from the same DNA duplex can be paired after analysis, the strand pairing can only reveal blunt end configuration after ER/AT. While it may not be crucial for DNA ends generated in vitro, it was discovered that the single strand overhangs of the ends (termed "jagged ends") of the cell-free plasma DNA may contain meaningful biological signals that differ between fetal/maternal as well as normal/cancerous origins (3). In their study (3), Jiang, P. et al. used the modified base 5methyl-dCTP to replace dCTP in ER/AT, so that synthesized patch can be distinguished from native DNA based on its epigenetic patterns, which then allows profiling of the 3'-single-strand protruding ends.

There are library preparation workflows that do not use the conventional ER/AT chemistry and have the benefit of minimal "writing" or "erasing" activities. For example, large genomic DNA can be sheared and tagged simultaneously with adaptors by transposase-based approach (6), but this is often not suitable for the already fragmented DNA, such as plasma-derived cell-free DNA or FFPE tissue extracted DNA. Other approaches, utilizing direct single strand ligation (7) or degenerate single strand mediated splint ligation (8), were reported. However, these methods often start with a heat denaturing step, during which DNA duplex and associated end information are lost. In addition, the hybridization based on complementarity among single strand DNA in the complex genomic library can be challenging. Harkins et al. reported a library preparation method that uses a pool of Y-adaptors with up to 6-nucleotide pre-defined degenerate ends to profile native ends of the library DNA (9). However, depending on the design of the adaptor pool, the limited possibilities may introduce bias to the analysis.

SUMMARY

Provided herein are compositions, kits, systems, and methods employing single-stranded end-preserving adaptors. Such single-stranded adaptors are attached to DNA duplex molecules while preserving original 5' or 3' single-strand protruding ends (e.g., present in cell-free DNA) by attaching such adapters to 3's ends the DNA duplex molecules using a single strand ligase that has step 3 ligase activity, but not step 2 adenylyl transfer activity, and attaching such adapters to the 5' ends of the DNA duplex molecules using a ligase enzyme (e.g., a circligase), thereby forming loop-like structures on one or each end of the DNA duplex molecules. In further embodiments, the loop-like structures are cleaved (e.g., by an endonuclease) as the single-stranded adapters have a cleavable portion, thereby generating a two-part adapter on one or both ends of the DNA duplex molecules that preserves the initial 5' or 3' single-strand protruding ends (or blunt ends), as the method does not require any end-repair or A-tailing. Unlike conventional end-repair/A-tailing used in library preparation, such methods do not alter DNA templates before the adaptor ligation step and are particularly useful in high-quality sequencing library preparation, including genomic and epigenomic sequencing library preparation and fragmentomic analyses.

In some embodiments, provided herein are methods of attaching an adaptor to a DNA duplex molecule (e.g., while preserving 5' or 3' single-strand protruding ends, along with any DNA modification present, such as methylation) comprising: a) generating a sample that comprises: a DNA duplex molecule, a first single-stranded adaptor, and a single strand ligase, wherein the single strand ligase has step 3 ligase activity, but not step 2 adenylyl transfer activity, wherein the DNA duplex molecule comprises: i) a first duplex end that comprises a 3' strand end and a 5' strand end, and has a 3' or 5' single-strand protruding end that is either a single non-adenine nucleotide (e.g., G, C, or T) or is at least two nucleotides in length (e.g., 2-15 nucleotides in length), and ii) a second duplex end that comprises a 3' strand end and a 5' strand end which optionally has a 3' or 5' single-strand protruding end (e.g., that is either a single non-adenine nucleotide (e.g., G, C, or T) or is at least two nucleotides in length (e.g., 2-15 nucleotides in length)), wherein the first single-stranded adaptor comprises a first nucleic acid sequence, and a 3' end blocking group attached to the 3' end of the first nucleic acid sequence, wherein the 5' end of the first nucleic acid sequence is adenylated, and wherein the first nucleic acid sequence comprises: a 5' region, a 3' region, and optionally a cleavable region between the 5' and 3' regions, b) incubating the sample at a temperature such that the single strand ligase ligates the 5' end of the first single-stranded adaptor to the 3' strand end of the first duplex end, c) optionally contacting the sample with a deblocking agent that removes or modifies the 3' end blocking group such that the 3' end of the first single-strand adaptor comprises a 3' end available for ligation; and d) optionally contacting the sample with a ligase enzyme that ligates the 3' end of the first single-stranded adaptor to the 5' strand end of the first duplex end thereby generating a first loop-like structure at the first duplex end of the DNA duplex molecule. In certain embodiments, any of, or all of, the protruding ends comprise at least one cytosine that is methylated. In particular embodiments, the first loop-structure is methylated at every (or almost every) cytosine present in the first loop-structure.

In further embodiments, the methods further comprise: e) contacting the sample with one or more enzymes such that the cleavable region of the first nucleic acid sequence is cleaved thereby generating a first two-part adaptor on the first duplex end that preserves the 3' or 5' single-strand protruding end of the first duplex end wherein the first two-part adaptor comprises: i) the 5' region of the first nucleic acid sequence attached to the 3' strand end of the first duplex end of the DNA duplex molecule, and ii) the 3' region of the first nucleic acid sequence attached to the 5' strand end of the first duplex end of the DNA duplex molecule. In other embodiments, sample in a) further comprises a second single-strand adaptor (e.g., that is identical with respect to elements present) to the first single-strand adaptor, wherein the second single-stranded adaptor comprises a second nucleic acid sequence and optionally a 3' blocking group attached to the 3' end of the second nucleic acid sequence, wherein the 5' end of the second nucleic acid sequence is adenylated, and wherein the second nucleic acid sequence comprises: a 5' region, a 3' region, and a cleavable region between the 5' and 3' regions, and wherein: i) during step b) the single strand ligase ligates the 5' end of the second single-stranded adaptor to the 3' strand end of the second duplex end, ii) optionally during step c) the deblocking agent removes or modifies the 3' end blocking group such that the 3' end of the second single-strand adaptor comprises a 3' end available for ligation; and iii) optionally during step d) the ligase enzyme ligates the free 3' end of the second single-stranded adaptor to the 5' strand end of the second duplex end of the DNA duplex molecule, thereby generating a second loop-like structure at the second duplex end of the DNA duplex molecule. In some embodiments, the first and/or second nucleic acid sequence is/are methylated at every (or almost every) cytosine present in the first and/or second nucleic acid sequence. In certain embodiments, the methylation is 5-methylcytosine (5mC) and/or 5-hydroxyl-methylcytosine (5hmC).

In additional embodiments, wherein during step e) the one or more enzymes cleave the cleavable region of the second nucleic acid sequence thereby generating a second two-part adaptor on the second duplex end, wherein the second two-part adaptor comprises: i) the 5' region of the second nucleic acid sequence attached to the 3' strand end of the second duplex end of the DNA duplex molecule, and ii) the 3' region of the second nucleic acid sequence attached to the 5' strand end of the second duplex end of the DNA duplex molecule.

In some embodiments, provided herein are methods of attaching adaptors to DNA duplex molecules while preserving 5' or 3' single-strand protruding ends (and any DNA modification present on the protruding ends, including methylation) of the DNA duplex molecules comprising: a) generating a sample that comprises: a plurality of DNA duplex molecules (e.g., cell-free DNA duplex molecules), a plurality of single-stranded adaptors, and a single strand ligase, wherein the single strand ligase has step 3 ligase activity, but not step 2 adenylyl transfer activity, wherein each of the DNA duplex molecules comprise: i) a first duplex end that comprises a 3' strand end and a 5' strand end, and has a 3' or 5' single-strand protruding end that is either a single non-adenine nucleotide or is at least two nucleotides in length, and ii) a second duplex end that comprises a 3' strand end and a 5' strand end which optionally has a 3' or 5' single-strand protruding or blunt end, wherein each of the single-stranded adaptors comprise a nucleic acid sequence and optionally a 3' blocking group attached to the 3' end of the nucleic acid sequence, wherein the 3' end blocking group is optionally a modified non-canonical nucleotide or a phosphate group, wherein the 5' end of the nucleic acid sequence is adenylated, and wherein the nucleic acid sequence comprises: a 5' region, a 3' region, and a cleavable region between the 5' and 3' regions, b) incubating the sample at a temperature such that the single strand ligase ligates the 5' ends of the single-stranded adaptors to the 3' strand ends of the first and second duplex ends, c) optionally contacting the sample with a deblocking agent that removes the 3' blocking group from the single-stranded adaptors if present; and d) contacting the sample with a ligase enzyme that ligates the 3' ends of the single-stranded adaptors to the 5' strand ends of the first and second duplex ends thereby generating a first loop-like structure at the first duplex ends of the plurality of the DNA duplex molecules, and generates a second looplike structure at the second duplex ends of the plurality of DNA duplex molecules. In certain embodiments, any of, or all of, the protruding ends comprise at least one cytosine (e.g., one, two, three, four, five or more cytosine) that is methylated.

In additional embodiments, the methods further comprise: e) contacting the sample with one or more enzymes such that the cleavable region of the nucleic acid sequences are cleaved thereby generating two-part adaptors on the first and second duplex ends of the plurality of duplex DNA molecules, wherein the two-part adaptors each comprise: i) the 5' region of the nucleic acid sequences attached to the 3' strand ends of the first duplex end of the plurality of DNA duplex molecules, and ii) the 3' region of the nucleic acid sequences attached to the 5' strand ends of the first duplex end of the plurality of DNA duplex molecules. In further embodiments, the plurality of DNA duplex molecules are contacted with bisulfite (or similar reagent or enzyme with the same function) to convert non-methylated (but not methylated) cytosines to uracil and sequenced as thymine. In additional embodiments, such DNA duplexes are employed to generate a sequencing library, which is then sequenced to generate a plurality of sequence reads (e.g., which can determine the location of originally methylated and non-methylated cytosines). In further embodiments, the plurality of DNA duplex molecules are contacted with chemicals or enzymes (e.g., in TAPS method or natural or engineered cytosine deaminases; see, e.g., Liu et al., Nature Biotechnology volume 37, pages 424-429 (2019), herein incorporated by reference) to convert only methylated cytosines (but not non-methylated cytosines) and sequenced as thymine.

In some embodiments, provided herein are methods of attaching an adaptor to a DNA duplex molecule comprising: a) generating a sample that comprises: a DNA duplex molecule, a first single-stranded adaptor, and a single strand ligase, wherein the single strand ligase has step 3 ligase activity, but not step 2 adenylyl transfer activity, wherein the DNA duplex molecule comprises: i) a first duplex end that comprises a 3' strand end and a 5' strand end, and ii) a second duplex end that comprises a 3' strand end, wherein the first single-stranded adaptor comprises a first nucleic acid sequence, and a 3' end blocking group attached to the 3' end of the first nucleic acid sequence, wherein the 5' end of the first nucleic acid sequence is adenylated, and wherein the first nucleic acid sequence comprises: a 5' region, a 3' region, and an cleavable region between the 5' and 3' regions, and b) incubating the sample at a temperature such that the single strand ligase ligates the 5' end of the first single-stranded adaptor to the 3' strand end of the first duplex end. In further embodiments, the methods further comprise: c) contacting the sample with a deblocking agent (if necessary) that removes or modifies the 3' end blocking group such that the 3' end of the first single-strand adaptor comprises a 3' end available for ligation; d) contacting the sample with a ligase enzyme that ligates the 3' end of the first single-stranded adaptor to the 5' strand end of the first duplex end thereby generating a first loop-like structure at the first duplex end of the DNA duplex molecule; and e) contacting the sample with one or more enzymes such that the cleavable region of the first nucleic acid sequence is cleaved thereby generating a first two-part adaptor on the first duplex end, wherein the first two-part adaptor comprises: i) the 5' region of the first nucleic acid sequence attached to the 3' strand end of the first duplex end of the DNA duplex molecule, and ii) the 3' region of the first nucleic acid sequence attached to the 5' strand end of the first duplex end of the DNA duplex molecule.

In further embodiments, the provided herein are methods of attaching an adaptor to a DNA duplex molecule while preserving 5' or 3' single-strand protruding ends comprising: a) generating a sample that comprises: a DNA duplex molecule, a first and second single-stranded adaptors, and a single strand ligase, wherein the single strand ligase has step 3 ligase activity, but not step 2 adenylyl transfer activity, wherein the DNA duplex molecule comprises: i) a first duplex end that comprises a 3' strand end and a 5' strand end, and has a 3' or 5' single-strand protruding end that is either a single non-adenine nucleotide or is at least two nucleotides in length, and ii) a second duplex end that comprises a 3' strand end and a 5' strand end which optionally has a 3' or 5' single-strand protruding end, wherein the first and second single-stranded adaptors each comprise a first nucleic acid sequence, and a 3' end blocking group attached to the 3' end of the first nucleic acid sequence, wherein the 5' end of the first nucleic acid sequence is adenylated, and wherein the first nucleic acid sequence comprises: a 5' region, a 3' region, and an cleavable region between the 5' and 3' regions, and b) incubating the sample at a temperature such that the single strand ligase: i) ligates the 5' end of the first single-stranded adaptor to the 3' strand end of the first duplex end, and ii) ligates the 5' end of the second single-stranded adaptor to the 3' strand end of the second duplex end, c) contacting the sample with a deblocking agent that removes or modifies the 3' end blocking group such that the 3' end of the first and second single-strand adaptors comprises a 3' end available for ligation; d) incubating the sample at a temperature such that the DNA duplex is denatured into first and second target-adaptor constructs; e) contacting the sample with a circligase enzyme such that the ends of the first and second target-adaptor constructs are ligated generating a first target-adaptor loop structure and a second target-adaptor loop structure; and f) optionally contacting the sample with one or more enzymes such that the cleavable region of the first nucleic acid sequence of the first and second adapters is cleaved thereby generating: i) a first two-part adaptor on the first duplex end that preserves the 3' or 5' single-strand protruding end of the first duplex end, and ii) a second two-part adaptor on the second duplex end.

In certain embodiments, provided herein are compositions comprising: a) a plurality of single-stranded adaptors, wherein each of the single-stranded adaptors comprises a nucleic acid sequence and optionally a 3' end blocking group attached to the 3' end of the nucleic acid sequence, wherein the 3' end blocking group is optionally a modified non-canonical nucleotide or a phosphate group, wherein the 5' end of the nucleic acid sequence is adenylated, and wherein the nucleic acid sequence comprises: a 5' region, a 3' region, and a cleavable region between the 5' and 3' regions; and b) a single strand ligase, wherein the single strand ligase has step 3 ligase activity, but not step 2 adenylyl transfer activity. In certain embodiments, the nucleic acid sequence is methylated at every (or almost every) cytosine present in the nucleic acid sequence. In certain embodiments, the methylation is 5-methylcytosine (5mC) and/or 5-hydroxylmethyl-cytosine (5hmC).

In some embodiments, provided herein are compositions, kits, and systems comprising: a) a plurality of single-stranded adaptors (or a single single-stranded adapter), wherein each of the single-stranded adaptors (or the adapter) comprises a single stranded nucleic acid sequence that is DNA except for one uracil base, wherein the single stranded nucleic acid sequence comprises: i) a first sequencing primer binding site which optionally comprises SEQ ID NO:56, ii) a second sequencing primer binding site which optionally comprises SEQ ID NO:57, iii) a 5' end that is adenylated, and iv) a 3' end that comprises a phosphate group; and wherein the uracil base is between the first and second sequencing primer binding sites, and optionally wherein the nucleic acid sequence is methylated at every, or almost every, cytosine present in the nucleic acid sequence.

In particular embodiments, the plurality of single-stranded adapters comprise at least 50 single-stranded adapters, and wherein each of the nucleic acid sequences further comprises a different barcode sequence, wherein the barcode sequence is optionally 2-12, or 13-18 (e.g., 2, 3, 4, 5, 6, 7, 8, 9, 10, 11, 12, 13, 14, 15, 16, 17, or 18) nucleotides in length. In other embodiments, the compositions, kits, and systems further comprise: b) a single strand ligase, wherein the single strand ligase has step 3 ligase activity, but not step 2 adenylyl transfer activity. In certain embodiments, the single stranded nucleic acid sequence further comprises: i) a first flow cell binding sequence which optionally comprises SEQ ID NO:59, and ii) a second flow cell binding sequence which optionally comprises SEQ ID NO:60. In other embodiments, the single stranded nucleic acid sequence further comprises: i) a first index sequence which optionally comprises SEQ ID NO:62, and ii) a second index sequence which optionally comprises SEQ ID NO:63. In further embodiments, the single stranded sequence comprises a sequence selected from: SEQ ID NOs: 54, 55, 58, and 61.

In additional embodiments, the compositions further comprise a deblocking agent. In further embodiments, the compositions further comprise a ligase enzyme selected from: a circligase, RtcB ligase from *E. coli.* and homologous RtcB ligases, thermostable RtcB such as that from *Thermus thermophilus* (27) or that from *Pyrococcus horikoshii* (28,30), Circligase I, Circligase II, TS2126 RNA ligase, and Mth DNA ligase, T4 RNA ligase 1, and T4 RNA ligase 2. In other embodiments, the compositions further comprise one or more enzymes capable of cleaving the cleavable region of the nucleic acid sequence. In additional embodiments, the compositions further comprise a plurality of DNA duplex molecules, wherein each of the DNA duplex molecule comprise: i) a first duplex end that comprises a 3' strand end and a 5' strand end, and has a 3' or 5' single-strand protruding or blunt end, and ii) a second duplex end that comprises a 3' strand end and a 5' strand end which optionally has a 3' or 5' single-strand protruding or blunt end. In additional embodiments, each of the DNA duplex molecules comprises a loop-like structure on the first duplex end and second duplex end, wherein the loop-like structure is composed of the nucleic acid sequence.

In further embodiments, provided herein are compositions comprising: a plurality of DNA duplex molecules which are fragmented genomic DNA duplex molecules and/or cell-free DNA duplex molecules, wherein each of the DNA duplex molecule comprise: i) a first duplex end that comprises a 3' strand end and a 5' strand end, and has a 3' or 5' single-strand protruding end that is either a single non-adenine nucleotide or is at least two nucleotides in length, and ii) a second duplex end that comprises a 3' strand end and a 5' strand end which optionally has a 3' or 5' single-strand protruding or blunt end, and wherein neither the first duplex or second duplex ends have not been changed by the addition or deletion of nucleotides, and wherein either: i) wherein each of the DNA duplex molecules comprises a loop-like structure on the first duplex end and second duplex end, wherein the loop-like structure is composed of the nucleic acid sequence that comprises: a 5' region, a 3' region, and a cleavable region between the 5' and 3' regions; or ii) wherein each of the DNA duplex molecules comprises a first two-part adaptor on the first duplex end, wherein each first two-part adaptor comprises: A) the 5' region of the nucleic acid sequence attached to the 3' strand end of the first duplex end of the DNA duplex molecule, and B) the 3' region of the first nucleic acid sequence attached to the 5' strand end of the first duplex end of the DNA duplex molecule. In certain embodiments, any of, or all of, the protruding ends comprise at least one cytosine that is methylated (e.g., all the cytosines present are methylated).

In certain embodiments, wherein, for part ii), each of the DNA duplex molecules further comprises a second two-part adaptor on the second duplex end, wherein each second two-part adaptor comprises: A) the 5' region of the second nucleic acid sequence attached to the 3' strand end of the second duplex end of the DNA duplex molecule, and B) the 3' region of the second nucleic acid sequence attached to the 5' strand end of the second duplex end of the DNA duplex molecule. In particular embodiments, a sequencing library is generated from at least some of the DNA duplex molecules, and optionally the sequencing library is sequenced to generate a plurality of sequence reads. In further embodiments, the fragmented genomic or cell free DNA duplex is from a human or mammalian species, optionally from a bodily fluid sample, which is optionally plasma, blood, urine, or semen. In some embodiments, the first and/or second nucleic acid sequence is methylated at every (or almost every) cytosine present in the first and/or second nucleic acid sequence. In certain embodiments, the methylation is 5-methylcytosine (5mC) and/or 5-hydroxylmethylcytosine (5hmC).

In some embodiments, provided herein are kits and compositions comprising: a) a plurality of single-stranded adaptors, wherein each of the single-stranded adaptors comprises a nucleic acid sequence and optionally a 3' end blocking group attached to the 3' end of the nucleic acid sequence, wherein the 3' end blocking group is optionally a modified non-canonical nucleotide or a phosphate group, wherein the 5' end of the nucleic acid sequence is adenylated, and wherein the nucleic acid sequence comprises: a 5' region, a 3' region, and a cleavable region between the 5' and 3' regions; and b) a single strand ligase, wherein the single strand ligase has step 3 ligase activity, but not step 2 adenylyl transfer activity. In certain embodiments, the nucleic acid sequence is methylated at every (or almost every) cytosine present in the nucleic acid sequence. In certain embodiments, the methylation is 5-methylcytosine (5mC) and/or 5-hydroxylmethylcytosine (5hmC).

In certain embodiments, the kits and systems further comprise a deblocking agent. In additional embodiments, the kits and systems further comprise a ligase enzyme selected from: a circligase, RtcB ligase from *E. coli.* or related homologous RtcB, thermostable RtcB, Circligase I, Circligase II, TS2126 RNA ligase, and Mth DNA ligase, T4 RNA ligase 1, and T4 RNA ligase 2. In additional embodiments, the kits and system further comprise one or more enzymes capable of cleaving the cleavable region of the nucleic acid sequence. In additional embodiments, the kits and systems further comprise a plurality of DNA duplex molecules, wherein each of the DNA duplex molecule comprise: i) a first duplex end that comprises a 3' strand end and a 5' strand end, and has a 3' or 5' single-strand protruding end that is either a single non-adenine nucleotide or is at least two nucleotides in length, and ii) a second duplex end that comprises a 3' strand end and a 5' strand end which optionally has a 3' or 5' single-strand protruding or blunt end. In further embodiments, each of the DNA duplex molecules comprises a loop-like structure on the first duplex end and second duplex end, wherein the loop-like structure is composed of the nucleic acid sequence. In some embodiments, the kits and systems further comprise one or more containers for collectively or separately holding the recited components, optionally, wherein the components are present inside the container. In additional embodiments, the one or more containers is selected from a cardboard box, a plastic bag or box, glass vials, and plastic vials. In certain embodiments, any of, or all of, the protruding ends comprise at least one cytosine (e.g., 1, 2, 3, or more) that is methylated.

In some embodiments, provided herein are compositions, kits, and system comprising: a plurality of single-stranded adaptors, wherein each of said single-stranded adaptors comprises a nucleic acid sequence, wherein the 5' end of said nucleic acid sequence is adenylated, wherein said nucleic acid sequence comprises: a 5' region, a 3' region, and a cleavable region between said 5' and 3' regions, wherein said 5' and 3' regions of said first nucleic acid sequence each comprise a barcode sequence that have predefined relationship to each other, and wherein at least one of the following: i) wherein said barcode in said 5' region is not complementary to said barcode in said 3' region, and/or ii) wherein said barcode in said 5' region has a different length than said barcode in said 3' region. In further embodiments, the pre-defined association of the barcodes is based on a look up table (e.g., tables 5-8). In further embodiments, barcode in said 5' region is same as barcode in 3' region (Table 8). In other embodiments, a 3' end blocking group is attached to said 3' end of said nucleic acid sequence, wherein said 3' end blocking group is optionally a modified non-canonical nucleotide or a phosphate group. In certain embodiments, the nucleic acid sequence is methylated at every (or almost every) cytosine present in the nucleic acid sequence. In certain embodiments, the methylation is 5-methylcytosine (5mC) and/or 5-hydroxylmethylcytosine (5hmC).

In particular embodiments, provided herein are compositions comprising: a sequencing library comprising a plurality of DNA duplex molecules with Y-shaped adapters attached at each end, wherein each of said Y-shaped adapters comprises a 5' arm and 3' arm, wherein said 5' arm has a first barcode and said 3' arm has a second barcode, and wherein at least one of the following: i) said first barcode is non-complementary to said second barcode, and/or ii) said first barcode is of a different length than said second barcode. In certain embodiments, the first and second barcodes have the same sequence. In certain embodiments, the Y-shaped adapters are methylated at every, or almost every, cytosine present in the nucleic acid sequence. In certain embodiments, the methylation is 5-methylcytosine (5mC) and/or 5-hydroxylmethylcytosine (5hmC).

In some embodiments, the 3' or 5' single-strand protruding end is exactly, or is at least, 3 nucleotides in length, and optionally, wherein the 3' or 5' single-strand protruding end is exactly, or is at least, 3, 4, 5, 6, 7, 8, 9, 10, 11, 12, 13, 14, 15, 16, or 20 nucleotides in length. In further embodiments, the 5' region and 3' region of the first two-part adaptor substantially, or completely, do not hybridize to each other. In additional embodiments, the first two-part adaptor forms a general V-configuration after ligation and cleavage (i.e., Y-shaped adapter minus the annealed lower stem part). In other embodiments, the 5' region and 3' region of the second two-part adaptor substantially, or completely, do not hybridize to each other. In additional embodiments, the second two-part adaptor forms a general V-configuration after ligation and cleavage (i.e., Y-shaped adapter minus the annealed lower stem part).

In particular embodiments, the cleavable region comprises: A) the modified non-canonical base, B) a nucleic acid backbone linkage (phosphorothioate or phosphodiester bond), or C) an endonuclease recognition site, wherein endonuclease recognition site is formed at the junction of the 5' and 3' regions or is composed of a sequence between the 5' and 3' regions, or D) one or more RNA bases, wherein optionally the rest of the first and second nucleic acid sequences are composed of DNA, or E) comprises a sequence that forms a endonuclease recognition sequence when a secondary oligonucleotide is added. In other embodiments, no end-repair and/or A-tailing is performed on the DNA duplex molecule(s).

In other embodiments, the temperature of the incubating is sufficient such that the first duplex end and/or second duplex end transiently separates. In particular embodiments, the temperature of the incubating is between 70 and 80 degrees Celsius or is about 75 degrees Celsius.

In further embodiments, the single strand ligase is a thermostable lysine-mutant ssDNA/RNA ligase which is a mutated version of a precursor thermostable ssDNA/RNA ligase, wherein the precursor thermostable ssDNA/RNA ligase has a Motif I EKx(D/N/H)G, and wherein the thermostable lysine-mutant replaces K in the Motif I with any other amino acid or is selected from alanine (A), serine(S), cysteine (C), valine (V), threonine (T), and Glycine (G). In certain embodiments, the thermostable lysine-mutant ssDNA/RNA ligase comprises a Motif sequence selected from the group consisting of: EGx(D/N/H)G (SEQ ID NO: 34), EPx(D/N/H)G (SEQ ID NO:35), EAx(D/N/H)G (SEQ ID NO:36), EVx(D/N/H)G (SEQ ID NO:37), ELx(D/N/H)G (SEQ ID NO:38), E Ix(D/N/H)G (SEQ ID NO:39), EMx (D/N/H)G (SEQ ID NO:40), ECx(D/N/H)G (SEQ ID NO:41), EFx(D/N/H)G (SEQ ID NO: 42), EYx(D/N/H)G (SEQ ID NO:43), EWx(D/N/H)G (SEQ ID NO:44), EHx (D/N/H)G (SEQ ID NO:45), ERx(D/N/H)G (SEQ ID NO:46), EQx(D/N/H)G (SEQ ID NO:47), ENx(D/N/H)G (SEQ ID NO:48), EEx(D/N/H)G (SEQ ID NO:49), EDx(D/ N/H)G (SEQ ID NO: 50), ESx(D/N/H)G (SEQ ID NO:51), ETx(D/N/H)G (SEQ ID NO:52) and Ex(D/N/H)G (SEQ ID NO:53), point deletion of lysine); wherein x is any amino acid. In particular embodiments, x is an amino acid with a small or smaller side chain compared to other amino acids. In some embodiments, the single strand ligase has an amino acid sequence that is 94% or 95% or 96% or 97% or 98% or 99% or 100% identical to any one of SEQ ID NOs: 1-21. In certain embodiments, the single strand ligase is a naturally occurring enzyme or is a mutant thereof. In particular embodiments, the single strand ligase is any one described in U.S. Pat. Pub. 20190062827, which is herein incorporated by reference in its entirety. In further embodiments, the single strand ligase is a naturally occurring enzyme or is a mutant thereof.

In further embodiments, the DNA duplex molecule(s) is cell free DNA (cfDNA) from a subject, wherein the first and second duplex ends of the DNA duplex molecule have not been changed by the addition or deletion of nucleotides. In additional embodiments, the subject is a human, and optionally wherein the cell free DNA duplex is extracted from a bodily fluid, which is optionally plasma, urine, blood, or CSF fluid.

In particular embodiments, the first duplex end of the DNA duplex molecule has a 3' single-strand protruding end. In other embodiments, the first duplex end of the DNA duplex molecule has a 5' single-strand protruding end. In additional embodiments, the second duplex end of the DNA duplex molecule has a 3' single-strand protruding end. In some embodiments, the second duplex end of the DNA duplex molecule has a 5' single-strand protruding end. In further embodiments, the first and/or second single-stranded adaptor comprises the 3' end blocking group, and wherein the c) is performed. In other embodiments, the first and/or second single-stranded adaptor does not have the 3' blocking group, and step c) is not performed.

In additional embodiments, the 5' and 3' regions of the second nucleic acid sequence each comprise at least one element selected from: a flow cell attachment sequence, a unique barcode sequence, a non-unique barcode sequence, a sample-identifying index sequence, a read 1 primer binding sequence, a read 2 primer binding sequence, and a universal PCR amplification primer binding sequence. In particular embodiments, the 5' and 3' regions of the first nucleic acid sequence each (or at least one of them) comprise at least one element selected from: a flow cell attachment sequence, a unique barcode sequence, a non-unique barcode sequence, a sample-identifying index sequence, a read 1 primer binding sequence, a read 2 primer binding sequence, and a universal PCR amplification primer binding sequence. In other embodiments, the 5' and 3' regions of the first nucleic acid sequence each comprise unique barcode sequences, and optionally wherein the barcodes sequences have a pre-defined relationship to each other, which is optionally based on a pre-defined association which may be a look up table (e.g., Tables 5-8) or other method to associate barcodes, and optionally wherein the barcode sequences are non-comple-mentary to each other, and optionally wherein the barcode sequences are same to each other, and optionally where the barcodes are of different lengths.

In additional embodiments, the methods further comprise contacting the sample with primers that hybridize to at least a portion of the 3' and 5' regions of the first nucleic acids sequence of the first two-part adaptor and performing PCR amplification to generate amplicons. In other embodiments, the methods further comprise: contacting sample with prim-ers that hybridize to at least a portion of the 3' and 5' regions of the first and second nucleic acid sequences of the first and second two part adaptors, and performing PCR amplification to generate amplicons. In further embodiments, the ampli-cons comprise barcodes, and the method further comprises: sequencing the amplicons to generate reads, grouping the reads bases at least in part on the barcodes, and optionally identifying original top and bottom strands of the DNA duplex molecule. In some embodiments, the methods further comprise: computationally determining the original first and second ends of the DNA duplex molecule.

In particular embodiments, the 3' end blocking group is selected from a nucleotide with 3'-phosphate group, and a nucleotide reversible terminator. In additional embodiments, the deblocking agent is selected from: an enzyme that has phosphatase activity, which is optionally selected from: T4 polynucleotide kinase, calf intestinal alkaline phosphatase (CIP), shrimp alkaline phosphatase (SAP), and chemical or physical agent for deblocking nucleotide reversible termi-nator, which is optionally buffered sodium nitrate, or UV light. In further embodiments, the ligase enzyme is selected from: Circligase I, Circligase II, Mth DNA ligase, RtcB ligase from *E. coli.*, thermostable RtcB, Taq DNA ligase, T4 RNA ligase 1, T4 RNA ligase 2. In further embodiments, the one more enzymes are selected from: an endonuclease, endonuclease V, endonuclease VIII, an endonuclease and uracil DNA glycosylase, thermostable oxoguanine glycosy-lase (OGG), and iodine.

In particular embodiments, the temperature of the incu-bating is sufficient such that the first duplex end and/or second duplex end transiently separates. In other embodi-ments, the temperature of the incubating is between 70 and 80 degrees Celsius (e.g., 70, 71, 72, 73, 74, 75, 76, 77, 78, 79, or 80) or is, or is about, 75 degrees Celsius.

In some embodiments, the 5' and 3' regions of the first nucleic acid sequence each comprise a barcode sequence, so that during analysis, reads with the same barcode sequence can be grouped together for error correction.

In some embodiments, the 5' and 3' regions of the first nucleic acid sequence each comprise a barcode sequence that has predefined relationship, and optionally wherein the barcode sequences are non-complementary to each other, and optionally wherein the barcode sequences are same to each other, and optionally where the barcodes are of differ-ent lengths. For example, they can be complementary to each other. Or, they may not be complementary and may be selected from a list of dual barcode pairs. During analysis, reads with barcodes that satisfy the predefined relationship can be paired to restore original duplex. In some embodi-ments, the paired duplex can be used for error correction. In some embodiments, original ends can be inferred from the paired duplex.

In particular embodiments, the 3' modified noncanonical nucleotide of the single strand adaptor is selected from: a nucleotide with 3'-phosphate group, or a nucleotide revers-ible terminator, for example, nucleotide reversible termina-tor with 3'-O-blocking group. For example, 3'-O-allyl (Ru-parel H, et al. (2005) Design and synthesis of a 3'-O-allyl photocleavable fluorescent nucleotide as a reversible termi-nator for DNA sequencing by synthesis. Proc Natl AcadSci USA, 102:5932-5937.) For another example, 3'-ONH2 (Chen F, et al (2009) Reconstructed evolutionary adaptive paths give polymerases accepting reversible terminators for sequencing and SNP detection, PNAS, 107: 1948-1953). Or nucleotide reversible terminator without 3'-blocking group, such as "virtual terminator" and can be deblocked by UV (cite: Wu W., et al. Termination of DNA synthesis by N6-alkylated, not 3-O-alkylated, photocleavable 2-deoxy-adenosine triphosphates. Nucleic Acids Res. 2007; 35:6339-6349).

In further embodiments, the deblocking agent is selected from: an enzyme with phosphatase activity, for example, T4 polynucleotide kinase, calf intestinal alkaline phosphatase (CIP), shrimp alkaline phosphatase (SAP). For nucleotide reversible terminator, chemical reagents or UV to remove the blocking group. For example, buffered (pH 5.5) sodium nitrite for reversing 3'-ONH2 to 3'-OH, as outlined in above referenced papers.

In some embodiments, the 5' and 3' regions of the first nucleic acid sequence each comprise a barcode sequence, so that during analysis, reads with the same barcode sequence can be grouped together for error correction.

In some embodiments, the 5' and 3' regions of the first nucleic acid sequence each comprise a barcode sequence that has predefined relationship, and optionally wherein the barcode sequences are non-complementary to each other, and optionally wherein the barcode sequences are same to each other, and optionally where the barcodes are of differ-ent lengths. For example, they can be complementary to each. Or, they may not be complementary and may be selected from a list of unique dual barcode pairs (e.g., as shown in Tables 5-8). During analysis, reads with barcodes that satisfy the predefined relationship can be paired to restore original duplex (e.g., such that original top and bottom strands can be identified). In some embodiments, the paired duplex can be used for error correction. In some embodiments, original ends can be inferred from the paired duplex.

In some embodiments, the 5' and 3' regions of the first nucleic acid sequence each comprise a barcode sequence that has predefined relationship, and optionally wherein the barcode sequences are non-complementary to each other, and optionally where the barcodes are of different lengths. For example, they can be complementary to each. Or, they may not be complementary and may be selected from a list of unique dual barcode pairs (e.g., look up tables such as Tables 5-8). During analysis, reads with barcodes that satisfy the predefined relationship can be paired to restore original duplex, and optionally wherein the barcode sequences are non-complementary to each other, and optionally where the barcodes are of different lengths. In some embodiments, the paired duplex can be used for error correction. In some embodiments, original ends can be inferred from the paired duplex.

In some embodiments, the kits and systems further comprise one or more containers for collectively or separately holding the recited components, optionally, wherein the components are present inside the container individually or in a mixed format. In additional embodiments, the one or more containers is selected from a cardboard box, a plastic bag or box, glass vials, and plastic vials.

BRIEF DESCRIPTION OF THE DRAWINGS

FIG. 1. Reaction temperature of exemplary DISTAL adaptor ligation methods. (A) Impact of reaction temperature to an exemplary DISTAL adaptor ligation method on a 320 bp duplex DNA. For DISTAL adaptor ligation methods series, lane 1-7 shows ligation of single strand adaptor to a DNA duplex approximately 300 bp at different temperatures. Lane 8 is duplex DNA only. Lane 9 is the same reaction catalyzed by the thermostable 5' App DNA/RNA Ligase (NEB) at 65° C. for 6 hours. Reaction samples were run on the high sensitivity D1000 screentape (Agilent) and analyzed by the TAPESTATION® automated electrophoresis system software. (B) Impact of reaction temperature to DISTAL adaptor ligation methods on a 180 bp duplex DNA. (C) Product distribution of reaction series in A and B. Molarity readings were obtained from TAPESTATION automated electrophoresis system analysis software.

FIG. 2 shows an exemplary DISTAL-seq adaptor ligation and sequencing methods workflow and results. (A) Diagram of this exemplary DISTAL-seq adaptor ligation and sequencing methods workflow. (B) TAPESTATION automated electrophoresis system trace of DISTAL-seq adaptor ligation and sequencing methods library using sheared *E. coli* genomic DNA. The distinct band around 150 bp is adaptor dimer. It's likely due to the residual unligated adaptors that go through deblocking, circularization, cleavage and amplification. (C) Sequence-specific bias for DISTAL adaptor ligation methods and Circligase II mediated ligation. (D) Coverage distribution for DISTAL-seq adaptor ligation and sequencing methods. (E) Mutation signature for the DISTAL-seq adaptor ligation and sequencing methods.

FIG. 3 shows an exemplary DUET-seq adaptor ligation and sequencing methods adaptor ligation and sequencing methods workflow and validation results on samples with known ends. (A) an exemplary DUET-seq adaptor ligation and sequencing methods adaptor ligation and sequencing methods adaptor preparation and read structure diagram. Unique molecular identifier (UMI) has 8 degenerate base, with 38-6561 possibly barcode on either end, totally 6561× 6561-4×$10^7$ possible combinations. Degenerate base uses B (B=G/C/T) to avoid USER enzymes (uracil DNA glycosylase and Endo VIII) cutting inside the UMI. After pair-end sequencing, first 8 bases of the read 1 is UMI and first 13 bases of read 2 is UMI, with 5 constant bases. (B) (C) TAPESTATION automated electrophoresis system traces of DUET-seq adaptor ligation and sequencing methods adaptor ligation and sequencing methods libraries using a mix of pre-digested lambda DNA. Lane B1: without ExoI/ExoIII treatment; Lane C1: with ExoI/ExoIII treatment. (C) Single strand end length after end restoration. After the duplex is restored, the end length is calculated as the 3'-end coordinate of the fragment mapped to the forward strand minus the 5'-end coordinate of the fragment mapped to the reverse strand, or the 5'-end coordinate of the fragment mapped to the forward strand minus the 3'-end coordinate of the fragment mapped to the reverse strand. Positive single strand end length denotes 5'-single-strand protruding end, while negative end length denotes 3'-single-strand protruding end. Value of zero denotes blunt end.

FIG. 4. End profiling of sheared genomic DNA and cell-free plasma DNA. (A) end length distribution of fragmented gDNA, including sonicated genomic DNA, enzymatically sheared genomic DNA and cell-free plasma DNA. (B) Insert distribution for the exemplary DUET-seq adaptor ligation and sequencing methods adaptor ligation and sequencing methods library of the cell free DNA. Data is taken from CollectInsertSizeMetrics from Picard Tools.

FIG. 11A shows an exemplary single stranded adaptor with a 3'-blocking group, which can be, for example: a 3'-phosphate, a 3'-dideoxyC, a 3'-biotin, a 3'-spacer, etc. Other 3' blocker examples are sold by IDT in their catalog at "Modifications/GetAllMods #3'." FIG. 11B shows an exemplary single stranded adaptor with an embedded cleavable site. A cleavable base can be, for example, an internal uracil (e.g., cleaved by UDG and Endo VIII), internal 5'-hydroxylmethyluracil, internal inosine (e.g., cleaved by Endo V), and internal 8-oxoGuanine (cleaved by OGG and EndoVIII). A cleavable backbone linkage can be a phosphodiester bond (e.g., cleaved by an endonuclease) or for example, could be a phosphorothioate DNA bond, which, for example, can be cleaved by iodine ($I_2$) (Qiang Huang et al. Origin of iodine preferential attack at sulfur in phosphorothioate and subsequent P—O or P—S bond dissociation, PNAS, vol 119, 2022, herein incorporated by reference). FIG. 11C shows an exemplary single stranded adaptor that can be cleaved by annealing a secondary oligo, forming a double-stranded region, which is then cleaved. This can be accomplished, for example, by embedding a few RNA bases, and cleaving by RNaseH, or by embedding a restriction enzyme site which is cleaved by restriction enzyme. FIG. 11D shows an exemplary single strand adaptor where more than one cleavage site is embedded inside the adaptor. Cleavage can be made, for example, sequentially. Such cleavage is also an alternative way to de-block the 3'-end. FIG. 11E shows two exemplary single stranded adaptors made of DNA and RNA, which may (top) or may not (bottom) employ a 3'-blocking group. FIG. 11F shows an exemplary single stranded adaptor with a 3' blocking group, which can be de-blocked by phosphatase, such as T4 PNK, shrimp alkaline phosphatase, etc. Another type of 3' block- ing that can be used is a nucleotide reversible terminator, for which the blocking group is removed by chemical agents.

FIG. 12A shows an exemplary single stranded adaptor that employs elements that, for example, can be used with ILLUMINA sequencers including: a read 2 primer sequence, a sample index 2, a P7 sequence, a P5 sequence, a sample index 1, and a read 1 primer sequence. FIG. 12B shows an exemplary single stranded adaptor that employs elements that, for example, can be used with ILLUMINA sequencers including: a second UMI (barcode) sequence, a read 2 primer sequence, a sample index 2, a P7 sequence, a P5 sequence, a sample index 1, a read 1 primer sequence, and a first UMI (barcode) sequence.

FIG. 13: RtcB Ligase from *E. coli* joins single stranded RNA with a 3'-phosphate or 2',3'-cyclic phosphate to another RNA with a 5'-hydroxyl end (25). It is also known that RtcB ligates 3'-phosphate end to 5'-hydroxyl end of single strand DNA (26). FIG. 13A shows the use RtcB to generally circularize the single-stranded adaptor sequences herein. For example, after hyigase ligation, one could use *E. coli* RtcB to directly ligate the 3'-phosphate end of the adaptor to the proximal 5'-end of the duplex, as shown in the FIG. 13A below, without de-blocking of the adaptor. In FIG. 13B, as *E. coli* RtcB catalyzes ligation at 37 degrees C., hyperligase ligation and RtcB ligation could occur in separate steps. As shown in FIG. 13B, by using thermostable RtcB, one could combine hyperligase ligation and RtcB in one reaction. Thermostable RtcBs have been reported (27) (28), both of which are herein incorporated by reference, particularly for the thermostable RtcBs reported therein.

FIG. 14A. Exemplary diagram of duplex recovery using 5' and 3' barcodes with predefined association (see look up tables 5-8). The Duplex DNA fragment shows one end with a protruding end of about 9 nucleotides, and a second end with a producing end of about six nucleotides. Duplex DNA fragment ends are ligated with single strand adaptor with 5' and 3' barcodes forming the dumb-bell DNA molecule shown with the protruding ends that are preserved. The two loops of this dumb-bell DNA molecule are then cleaved. PCR amplification is then employed, such as with universal primers. These amplicons are then sequenced to generate sequence reads. Read pairs with proper association are used to recover duplex, as shown in the figure. Note that the recovered duplex is not necessarily blunt ended. The end coordinates can be used to recover the ends present in the starting material. FIG. 14B shows the same exemplary figure as FIG. 14A, but without barcodes added and with 3' protruding ends.

FIGS. 15A and 15B show exemplary embodiments where the barcodes in the two adapters flanking a template sequence are of different lengths.

FIG. 16A shows how the methods and compositions herein preserve methylation on 3' and 5' protruding ends of target DNA as, for example, no end-repair or A-tailing is required of the target DNA. FIG. 16B shows an exemplary workflow using fully methylated nucleic acid sequences that form adapters herein.

FIG. 18A shows a workflow similar to that of FIG. 2, except once the dumbbell type structure if formed, a primer that is designed to anneal to the adaptor sequence is added to initiate rolling-circle amplification (RCA), to generate concatenated single-strand DNA with multiple copies of the duplex DNA templates. In FIG. 18B, after the first and second adaptors are ligated to the duplex DNA molecule, duplex DNA is denatured and subject to deblocking/ligation, so that each strand forms single strand circles with the adaptor sequence embedded inside. A primer that is designed to anneal to the adaptor sequence is added to initiate rolling-circle amplification (RCA), to generate con- catenated single-strand DNA with multiple copies of the strand-specific DNA templates.

FIG. 19A shows the nucleic acid sequence (SEQ ID NO:54) of an exemplary single-stranded adapter, which is composed of DNA bases (e.g., 4 canonical bases) except for one uracil base. The Read 2 primer binding site (AGATCG- GAAGAGCACACGTCTGAACTCCAGTCAC; SEQ ID NO:56) and Read 1 sequencing primer binding site (ACACTCTTTCCCTACACGACGCTCTTCCGATCT; SEQ ID NO:57), are used in certain Illumina sequencing instruments and are marked. The 5' end is adenylated and the 3' end has a phosphate group. FIG. 19B shows the same sequence as FIG. 19A, but further includes a 5 base random barcode at each end, to form SEQ ID NO:55. FIG. 19C shows the same sequence as FIG. 19A (SEQ ID NO:54), but further diagrammatically depicts Barcode 1 at one end and Barcode 2 at the other ends. Barcodes 1 and 2, in a pool of adapters, can be (for example) be any of the barcode pairs from Table 8, which can form 96 pairs. FIG. 19D shows an exemplary single strand adapter (SEQ ID NO:58) similar to FIG. 19A, but further includes a flow cell binding P7 sequence (ATCTCGTATGCCGTCTTCTGCTTG, SEQ ID NO:59) and a P5 flow cell binding sequence (AATGA- TACGGCGACCACCGAGATCTACAC, SEQ ID NO:60), that may be used, for example, when PCR is not used to add these sequences. FIG. 19E shows a similar sequence (SEQ ID NO:61) as FIG. 19D, but further adds an i7 (CT- GATCGT, SEQ ID NO:62) and an i5 (ATATGCGC, SEQ ID NO:63) index sequences.

DEFINITIONS

Figure 5:
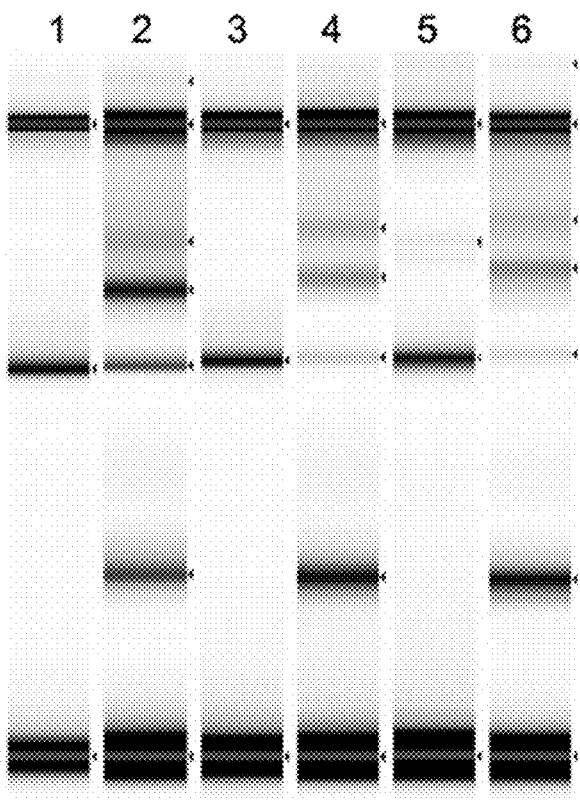
FIG. 5. Exemplary DISTAL adaptor ligation methods using 5'-single-strand protruding or 3'-single-strand protruding DNA, and comparison to blunt end DNA. Lane 1, blunt end DNA; lane 2, exemplary DISTAL adaptor ligation methods using blunt end DNA; lane 3, 5'-single-strand protruding DNA; lane 4, exemplary DISTAL adaptor ligation methods using 5'-single-strand protruding DNA; lane 5, 3'-single-strand protruding DNA; lane 6, DISTAL adaptor ligation methods using 3'-single-strand protruding DNA.

A single-stranded DNA/RNA ligase enzyme is considered to have "step 3 ligase activity" but not "step 2 adenylyl transfer activity," when it is able to ligate between 5'-ad- enylated end and 3'-hydroxyl end of single strand DNA/ RNA, but not able to transfer the AMP to the 5'-phosphate- terminated DNA or RNA strand to form a 5'-App-DNA/ RNA intermediate. All known DNA and RNA ligases perform the catalysis via a common pathway which involves three nucleotidyl transfer reactions (Lehman et al, Science, 1974; Lindahl et al, Annu Rev Biochem, 1992). In the case of ATP-dependent DNA or RNA ligases, the first step (step 1) involves the attack on the α-phosphate of ATP by ligase, which results in release of pyrophosphate and formation of a ligase-AMP intermediate. AMP is linked covalently to the amino group of a lysine residue within a conserved sequence motif. In the second step (step 2), the AMP nucleotide is transferred to the 5'-phosphate-terminated DNA or RNA strand to form a 5'-App-DNA/RNA intermediate. In the third and final step (step 3), attack by the 3'-OH strand on the 5'-App-DNA/RNA end joins the two polynucleotides and liberates AMP.

"End repair" means fill-in of the 3'-single-strand protrud- ing ends by polymerase and/or resection of the 5'-singlestrand protruding ends of the original DNA analyte DNA duplex. In certain embodiments, the methods herein do not employ any type of end repair.

DETAILED DESCRIPTION

Provided herein are compositions, kits, systems, and methods employing single-stranded end-preserving adaptors. Such single-stranded adaptors are attached to DNA duplex molecules while preserving original 5' or 3' single-strand protruding ends (e.g., present in cell-free DNA) by attaching such adapters to 3's ends the DNA duplex molecules using a single strand ligase that has step 3 ligase activity, but not step 2 adenylyl transfer activity, and attaching such adapters to the 5' ends of the DNA duplex molecules using a ligase enzyme (e.g., a circligase), thereby forming loop-like structures on one or each end of the DNA duplex molecules. In further embodiments, the loop-like structures are cleaved (e.g., by an endonuclease) as the single-stranded adapters have a cleavable portion, thereby generating a two-part adapter on one or both ends of the DNA duplex molecules that preserves the initial 5' or 3' single-strand protruding ends (or blunt ends), as the method does not require any end-repair or A-tailing. Such methods are particularly useful in sequencing library preparation and fragmentomic analyses, along with any methylation present.

Current end repair/A-tailing (ER/AT) chemistry during NGS library preparation results in "writing" and "erasing" activities to the starting material, which introduce a variety of artifacts and implications to the sequencing and data interpretation. In addition, conventional ER/AT abolishes the native DNA ends, which for some types of samples can be informative when they are generated biologically. Provided herein, in certain embodiments, is a sequencing library preparation workflow that employs ligation (e.g., before an amplification step). In some embodiments, an important step is the duplex-retaining single strand DNA tail ligation (DISTAL adaptor ligation methods) schema (e.g., as exemplified in FIG. 2), in which ligation occurs at elevated temperature between duplex and single strand adaptor, catalyzed by a thermostable single strand DNA ligase (e.g., a thermostable lysine-mutant, such as shown in Tables 1 and 2 below). Work conducted during development of embodiments herein shows that embodiments of DISTAL adaptor ligation methods enable new sequencing library preparation workflows in which no end repair or A-tailing is necessary. In addition, in some embodiments, by using a barcoded adaptor, it is feasible to restore originally paired DNA strands in the same duplex as well as the native DNA ends that comes with that pairing (DUET-seq adaptor ligation and sequencing methods adaptor ligation and sequencing methods). In certain embodiments, DUET-seq adaptor ligation and sequencing methods adaptor ligation and sequencing methods is applied to biological samples, such as those containing fragmented human genomic DNA and/or cell-free plasma DNA.

In particular embodiments, the single-strand adaptors herein comprise a 5' region and a 3' region, and wherein the 5' region comprises a first barcodes sequence, and the 3' region comprises a second barcode sequence. In some embodiments, the first and second barcodes sequences are complementary and may hybridize to each other. In other embodiments, the first and second barcodes are not complementary and do not hybridize to each other.

Such embodiments where the first and second barcode sequences do not hybridize to each other is different than the normal approach in the art where the barcode sequence is in the "stalk" of a Y shaped adaptor, necessitating that the first and second barcodes are always complementary to each other (due to the constraint of hybridization). As the result, in normal approach, adaptor with barcode A ligates to one end of the duplex and adaptor with barcode B ligates to the other end of the duplex, so that read pair from one strand has barcode "AB", and read pair from the other strand has barcode "BA,". During analysis, read pairs that share the same genomic coordinates of start and stop positions, and also AB/BA barcodes are considered as duplex.

In embodiments herein the 5' and 3' barcodes are not complementary to each other, as shown in Table 5 below: where AB, CD, EF, and GH each represent 5' barcode and 3' barcode and do not hybridize to each other. Single strand adaptors with unique combinations of AB, CD, EF, and GH may be synthesized individually, and used as a mixture. As an example, during ligation, first single strand adaptor with barcode A and B ligates to the first duplex end, and second single strand adaptor with barcode C and D ligates to the second duplex end. Read pair from one strand has barcode DA, and read pair from the other strand has barcode BC. During analysis, read pairs that overlap in their start and stop positions, and have the corresponding association as defined in the look up table (e.g., as long as they pair with each other in this table, DA/BC in the example, and therefore have a predetermined relationship that can be looked up) are considered duplex. The duplex ends can then be inferred from the genomic start and stop positions of the two strands at either end.

TABLE 5

| 5' barcode | 3' barcode |
|------------|------------|
| A          | B          |
| C          | D          |
| E          | F          |
| G          | H          |

Figure 14C:
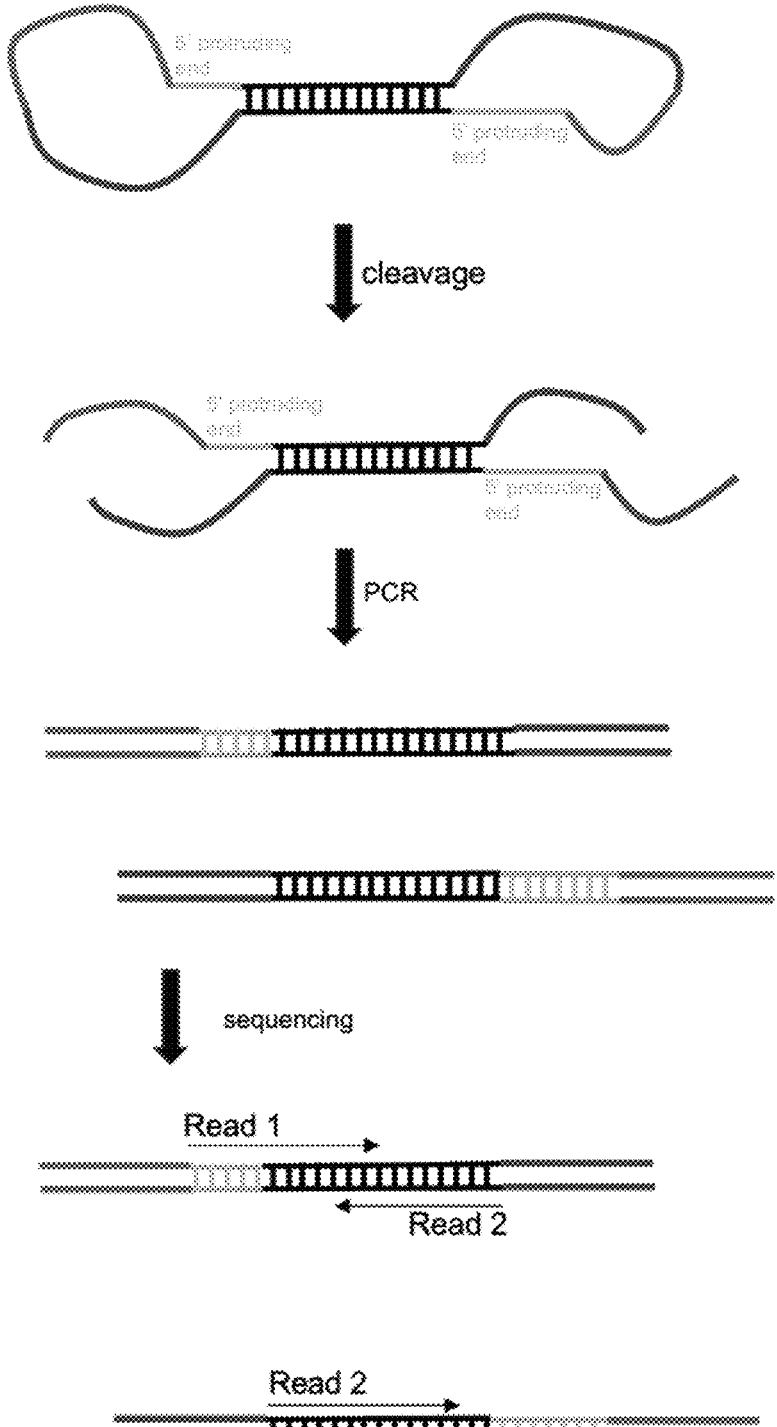
FIG. 14C shows a similar exemplary figure without barcodes and 5' protruding ends.
Figure 17:
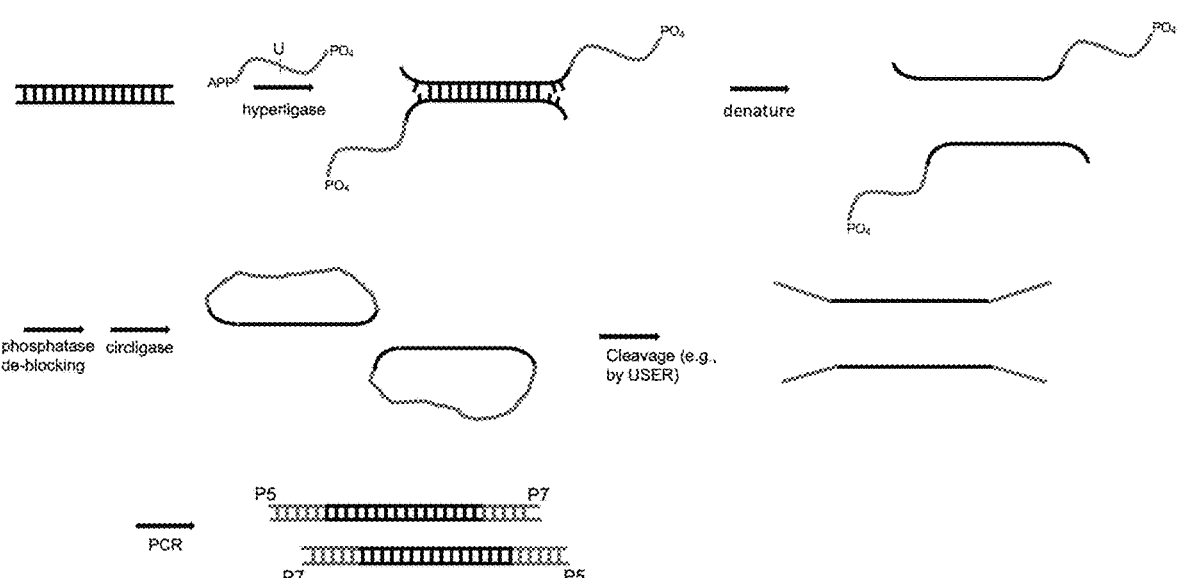
FIG. 17 shows a workflow where after ligation as described herein, instead of maintaining the duplex, DNA sample is denatured and each single strand DNA is circularized individually.

FIG. 14A provides an exemplary figure demonstrating the use of barcodes that can be looked up (for bottom and top strand) in a look up table such as Table 5 above. FIG. 14A shows that the Duplex DNA fragment with one end with a protruding end of about 9 nucleotides, and a second end with a producing end of about six nucleotides. Duplex DNA fragment ends are ligated with single strand adaptor with 5' and 3' barcodes forming the dumb-bell DNA molecule shown with the protruding ends that are preserved. The two loops of this dumb-bell DNA molecule are then cleaved. PCR amplification is then employed, such as with universal primers. These amplicons are then sequenced to generate sequence reads. Read pairs with proper association are used to recover duplex, as shown in the figure. Note that the recovered duplex is not necessarily blunt ended. After reads are mapped onto reference genome, the end coordinates can be used to recover the ends present in the starting material.

As discussed above, the barcodes herein do not need to be complimentary, which, for example, expands the design space to 16 possible combinations for 1-mers as shown in Table 6 below, in contrast to only 4 possible combinations if complementarity is required.

TABLE 6

| 1-mer duplex barcode design table | | |
|------------|------------|------------|
| 5'-barcode | 3'-barcode | Mismatch |
| A          | A          | 1          |
| A          | C          | 1          |
| A          | G          | 1          |
| A          | T          | 0          |

TABLE 6-continued

| 1-mer duplex barcode design table | | |
| --- | --- | --- |
| 5'-barcode | 3'-barcode | Mismatch |
| C | C | 1 |
| C | G | 0 |
| C | T | 1 |
| C | A | 1 |
| G | A | 1 |
| G | T | 1 |
| G | C | 0 |
| G | G | 1 |
| T | T | 1 |
| T | A | 0 |
| T | C | 1 |
| T | G | 1 |

A possible look up table for the 1 mer duplex barcode is:

TABLE 6.1

| 5'-barcode | 3'-barcode |
| --- | --- |
| A | A |
| C | T |
| G | G |
| T | C |

Another possible look up table for the 1 mer duplex barcode is:

TABLE 6.2

| 5'-barcode | 3'-barcode |
| --- | --- |
| A | C |
| C | T |
| G | A |
| T | G |

As another example, barcodes of equal or unequal length can be used as duplex barcodes.

TABLE 7

| barcodes of different length | |
| --- | --- |
| 5'-barcode | 3'-barcode |
| AA | CCT |
| CC | TT |
| GC | A |
| TA | CCGG |
| TC | CC |

As another example, barcodes of same sequences can be used duplex barcodes. This design has the added advantage that a look up table is not even needed.

TABLE 8

| an example design of 96 duplex barcodes with same sequences | |
| --- | --- |
| 5'-Barcode | 3'-Barcode |
| AATGCAC | AATGCAC |
| ATCCTTG | ATCCTTG |
| GTATGCT | GTATGCT |

TABLE 8-continued

| an example design of 96 duplex barcodes with same sequences | |
| --- | --- |
| 5'-Barcode | 3'-Barcode |
| AGATGCG | AGATGCG |
| ATGTGGC | ATGTGGC |
| CGATACT | CGATACT |
| GACTGTA | GACTGTA |
| GGTACGT | GGTACGT |
| TAACGCG | TAACGCG |
| TTACGGC | TTACGGC |
| AACCGCA | AACCGCA |
| AACGTCC | AACGTCC |
| ACGCAGT | ACGCAGT |
| AGGCACA | AGGCACA |
| CAACACA | CAACACA |
| GATCGCT | GATCGCT |
| GGATATA | GGATATA |
| GGATCAG | GGATCAG |
| TTGTGCG | TTGTGCG |
| ACCGAAC | ACCGAAC |
| AGCGACT | AGCGACT |
| AGGTTAA | AGGTTAA |
| ATATTGG | ATATTGG |
| ATCACAC | ATCACAC |
| ATTAGGT | ATTAGGT |
| CAATATC | CAATATC |
| CAGTGGA | CAGTGGA |
| CCGATAG | CCGATAG |
| CTACATT | CTACATT |
| CTGTATA | CTGTATA |
| GAGTGAG | GAGTGAG |
| GATCCAG | GATCCAG |
| GCTACAC | GCTACAC |
| GCTCGAA | GCTCGAA |
| GGATTCC | GGATTCC |
| GGTGCAA | GGTGCAA |
| GTAAGAG | GTAAGAG |
| GTACCTG | GTACCTG |
| GTAGTCG | GTAGTCG |
| GTGTACC | GTGTACC |

TABLE 8-continued

| an example design of 96 duplex barcodes with same sequences | |
| --- | --- |
| 5'-Barcode | 3'-Barcode |
| TCCGACA | TCCGACA |
| TTAGCCT | TTAGCCT |
| ACTGTTC | ACTGTTC |
| AGAATAC | AGAATAC |
| ATCAATA | ATCAATA |
| ATGCGCT | ATGCGCT |
| ATTGTAG | ATTGTAG |
| CAATGAT | CAATGAT |
| CATACAT | CATACAT |
| CATGCCA | CATGCCA |
| CGCGATA | CGCGATA |
| CGGCAAT | CGGCAAT |
| CTGTTAT | CTGTTAT |
| GAATAGG | GAATAGG |
| GATTATT | GATTATT |
| GCCTTAC | GCCTTAC |
| GTTAGTA | GTTAGTA |
| TACCATA | TACCATA |
| TATAATG | TATAATG |
| TCGAAGG | TCGAAGG |
| TCGACAT | TCGACAT |
| TGAAGTG | TGAAGTG |
| TGTCCAT | TGTCCAT |
| TGTTAAG | TGTTAAG |
| AACTTAG | AACTTAG |
| AAGCTGG | AAGCTGG |
| AATATCG | AATATCG |
| AATGTGT | AATGTGT |
| ACACTTA | ACACTTA |
| ACGAACC | ACGAACC |
| AGGTAGG | AGGTAGG |
| ATAGGCC | ATAGGCC |
| ATATAAC | ATATAAC |
| ATGATTC | ATGATTC |
| CACTCAC | CACTCAC |
| CAGGAAC | CAGGAAC |
| CCGGATT | CCGGATT |

TABLE 8-continued

| an example design of 96 duplex barcodes with same sequences | |
| --- | --- |
| 5'-Barcode | 3'-Barcode |
| CGGATGT | CGGATGT |
| CTAATAA | CTAATAA |
| CTCTGTG | CTCTGTG |
| CTGGTGA | CTGGTGA |
| CTTGTCC | CTTGTCC |
| GAGCAGA | GAGCAGA |
| GCAATGG | GCAATGG |
| GCCGTTA | GCCGTTA |
| GCTGAAG | GCTGAAG |
| GTTCTTC | GTTCTTC |
| GTTGGAT | GTTGGAT |
| TAACCTT | TAACCTT |
| TAGCGGT | TAGCGGT |
| TAGGACG | TAGGACG |
| TCGCTCA | TCGCTCA |
| TCGTAAC | TCGTAAC |
| TGATTAT | TGATTAT |
| TGCACAG | TGCACAG |
| TGGATCG | TGGATCG |

In certain embodiments, the two barcodes used herein (for a particular template) do not have the same length (and may or may not be complimentary, and may be the same sequence). Such embodiments are shown in exemplary FIG. 15A. This figure shows that the duplex barcodes are not complementary, and are not the same length. Thus, combinations of barcode design of different lengths further expands the design space that one may employ in the methods and compositions herein. It is noted that one exemplary advantage of this significantly expanded barcode design space reduces the requirement of barcode length for a same level of adaptor pool complexity. This can reduce the length of the adaptor oligonucleotides, and thereby reduce the synthesis cost. In further embodiments, as shown in FIG. 15B, the associated barcodes may contain additional degenerate bases of equal or unequal length.

In some embodiments, the barcodes (e.g., non-complementary barcodes; same sequence) may have a length of 1, 2, 3, 4, 5, 6, 7, or more nucleotides. In particular embodiments, the non-complementary barcodes have 1, 2, 3 or more mismatches. In particular embodiments, barcodes (e.g., only barcodes) that form pairs with maximal mismatches (hamming distance). In other embodiments, the barcodes are exactly the same. In further embodiments, the strand combinations of two barcodes have a length difference, such as 1, 2, 3, 4, or more differences. In particular embodiments, one of the two barcodes in the combination is not present (zero nucleotides). In other the barcodes have certain constant and/or degenerate bases.

In certain embodiments, the thermostable lysine-mutants employed in the methods, kits, systems, and compositions herein with the single stranded adaptors are as provided in SEQ ID Nos: 1-21 in Tables 1 and 2 below, or N or C terminal truncated, versions thereof.

TABLE 1

| Thermostable Lysine-Mutant ssDNA/RNA Ligases | | |
| --- | --- | --- |
| Amino Acid Sequence | SEQ ID NO: | Species name |
| MVSSYFRNLLLKLGLPEERLEVLEGKGALAEDEFEGIRYVRFRDSARNFRRG TVVFETGEAVLGFPHIKRVVQLENGIRRVFKNKPFYVEEXVDGYNVRVVKVK DKILAITRGGFVCPFTTERIEDFVNFDFFKDYPNLVLVGEMAGPESPYLVEG PPYVKEDIEFFLFDIQEKGTGRSLPAEERYRLAEEYGIPQVERFGLYDSSKV GELKELIEWLSEEKREGIVMKSPDMRRIAKYVTPYANINDIKIGSHIFFDLP HGYFMGRIKRLAFYLAENHVRGEEFENYAKALGTALLRPFVESIHEVANGGE VDETFTVRVKNITTAHKMVTHFERLGVKIHIEDIEDLGNGYWRITEKRVYPD ATREIRELWNGLAFVD Where X is any amino acid except K. | 1 | *Thermococcus kodakarensis* |
| MVSSHFKEILMRLGLPEDRIEVLEAKGGITEEEFDGIRYLRFKDSARGLRRG TVVFDEANVILGFPHIKRVVSLRAGVMRIFKRTPFYVEEXVDGYNVRVALVS DRVLAITRGGFVCPFTTERILDFVPEEFFKDYPHLVLVGEMAGPESPYLVEG PPYVEEDIRFFLFDIQEKGTGKSLPVQERLKLAEEYGIPHVKVFGLYTVDRI EDLYDLIERLSREGREGVVMKSPDMKRVVKYVTPFANVNDVKIGAKVFFELP PGYFMSRIMRLAFYVAERRIKGERFEELARNLGKALLEPFVESIWDVEQGDE IAEVFRIRVKRIETAYKMVTHFERLGLNIKIEDIEEVGGMWRITFKRAYDEA TREIRELIGGRAFVD Where X is any amino acid except K. | 2 | *Pyrococcus yayanosii* |
| MVSSKFKDILYRLGIPEGKVEDLEARGGLVEDKFDDIKYLRIRNSVGKLRRG TVVLNDKFIILGFPHIKRIVNLKNGIKRTFKRGEFYVEEXVDGYNVRVVKFR GKXLGITRGGFICPFTTERISDFIPEEFFKDHPNLILVGEMAGPESPYLVEG PPYVKEDIQFFLFDIQELGTGRSLPVEERLKIAEEYGISHVEVFGKFTYKDL EEIYEIVERLSREGREGIVMKSPDMRKMVKYVTPYANINDIKIGARVFYELP PGYFTSRISRLAFYIAEKRLRGENFEELAKELGKALLQPLVESIHDVEQEDE IAEVFKVRVKKIETAYKMVTHFEKLGLRIEIVDIEEMKGGWRITFKRLYPDA TEEIRELIGGKSFVD Where X is any amino acid except K. | 3 | *Pyrococcus horikoshii* |
| MKEVVSSVYKEILVKLGLTEDRIETLEMKGGIIEDEFDGIRYVRFKDSAGKL RRGTVVIDEEYVIPGFPHIKRIINLRSGIRRIFKRGEFYVEEXVDGYNVRVV MYKGKMLGITRGGFICPFTTERIPDFVPQEFFKDNPNLILVGEMAGPESPYL VEGPPYVKEDIQFFLFDVQEIKTGRSLPVEERLKIAEEYGINHVEVFGKYTK DDVDELYQLIERLSKEGREGIIMKSPDMKKIVKYVTPYANINDIKIGARVFY ELPPGYFTSRISRLAFYLAEKRIKGEEFERVAKELGSALLQPFVESIFDVEQ EEDIHELFKVRVKRIETAYKMVTHFEKLGLKIEIVDIEEIKDGWRITFKRLY PDATNEIRELIGGKAFVD Where X is any amino acid except K. | 4 | *Pyrococcus abyssi* |
| MENMVSSKFKELLYTLGIPEDKVEILEARGGIMEDEFEGIRYLRFKNSVGKL RRGTVLFEDGTTVFGFPHIKRIVNLSAGVRKIFKSSEFYVEEXVDGYNVRVV KFKDRILGITRGGFICPYTTERIAEFVPEEFFKDHKDLVLVGEMAGPESPYL VEGPPYVKEDIQFFLFDIQDIKTGSSLPVEERLKLAEEYGINHVEVFGRYSY KDIDDLYELIERLSREGREGIVMKSPDMKKIVKYVTPYANINDIKIGARVFY ELPGGYFTSRISRLAFYIAEKKIRGEELHNLALQLGKALLQPLVEAIHDVTQ GDVIAERFRVRVRKIETAYKMVTHFEKLGLEIEIEDIEEIEGGWRVTFKRVY PEATREIRDLIGGKAFVD Where X is any amino acid except K. | 5 | *Pyrococcus furiosus* |
| MTWIKNPEPWMVNLVAEKLGLDVERVETLARHGTIRFRGYRDVVYALLRREI AGHPEGTVVLLERNGARLVPGYPPIQRMVLPTIALPRHFIDKVVVEEXMNGY NVRLVMFHRKLLAVTRGGFICPYTTARLERLIGGRVRELFREIDPETYTIAG EVVGLENPYTRYFYPEAPRFDYFVFDLFHELKPLPPLERNELLEKYGLKHVR LLGVIDKNDVEMFKQIVAELDREGREGVVAKDPEYRVPPLKYTTSAVNIGDV RYGMRFFMEEGRSFLFSRLLRELFRAYEEGFGDAQLEKLALEFGRAATEPAL ESIRKVAMGDMLYEEFELVFADEVELEEFTSYMAELGVDIVVVSTSREDEGL RARMRKIKDTWIQLRKVLDTGLSPVD Where X is any amino acid except K. | 6 | *Hyperthermus butylicus* |
| MTWIKNPEPWMVNLVAEKLGLDVERVETLARHGTIRFRGYRDVVYALLRREI AGHPEGTVVLLERNGARLVPGYPPIQRMVLPTIALPRHFIDKVVVEEAMNGY NVRLVMFHRKLLAVTRGGFICPYTTARLERLIGGRVRELFREIDPETYTIAG EVVGLENPYTRYFYPEAPRFDYFVFDLFHELKPLPPLERNELLEKYGLKHVR LLGVIDKNDVEMFKQIVAELDREGREGVVAKDPEYRVPPLKYTTSAVNIGDV RYGMRFFMEEGRSFLFSRLLRELFRAYEEGFGDAQLEKLALEFGRAATEPAL ESIRKVAMGDMLYEEFELVFADEVELEEFTSYMAELGVDIVVVSTSREDEGL RARMRKIKDTWIQLRKVLDTGLSPVD | 7 | *HbuRN12K106A* |

TABLE 1-continued

Thermostable Lysine-Mutant ssDNA/RNA Ligases

| Amino Acid Sequence | SEQ ID NO: | Species name |
|---|---|---|
| MASAAEVLASALRAVGVDPGSVDLEALSTRRSVRVSRFEDVVYVGFRRQFRG<br>VPEGTLVAFRRGEQIVVWGYPSIKRMLLPRVAVPRWFPGPTVLVEEXMNGYN<br>VRVFTLGGMVYAATRGGLICPYTTRRLRRLYGGALQKILEDLGAEGSFIAGE<br>VVGLENPYTRYYYEEAPGFGYFIFDIFKGGRQLPPRVKFSLAPEYGLKTVNL<br>LAEIPATASGVERLYTIVEDLEKRGREGVIVKDPEGRVEPLKYTTSRINIGD<br>IRLGMRYPFEEGRSFLFPRILREIFREWETGRRRYGELGEAILAPAIEAVEA<br>VSRGGRLVEEFELVFANEVEAEEVIAYFASLGVHLEIAGVARGVDGVRVAFR<br>KPRKSEGEIARILETGISPLD<br>Where X is any amino acid except K. | 8 | *Aeropyrum pernix* |
| MDENELVNKLSDALGIEYEKLSKHIGRSIRLMKYGELNYVVERRDLLGYREG<br>TTILLGEEPLIVHGYPSIQRLAFIEGVSKHMIDNVVVEEXMNGYNVRVVYM<br>NNIYAITRGGYICPYTTARIRKLYSKNIKLAYQEYPDTILVGEVVGTENPYV<br>IYDYPEARGFDYFIFDTMKKDKLQPLRIRDEIAEKYSLKTVRILDIINKRDI<br>DRLKTIINRLEKERREGVVLKDPYQRVPPLKYTTIYINIRDIWEGMRYPFDE<br>GRGYLFSRIVRLIAQGYEYDWNNTELDRIALKLGRAILEPAINSLKKRANGE<br>IIASKYTLVFPSEDDLSKYIEYAESIGMDFIFRVVEKREDGCIVVELFKMKE<br>THNIYTKMLKTGYSPLD<br>Where X is any amino acid except K. | 9 | *Staphylothermus marinus* |
| MIRIPLERWMIEKLAEALNVNIEEAERLARRRNVVRLMKWRNVTYFSLRKDV<br>YGLREGTLIAVWPDGYRVVPGYPSIQRVLLPSVALPKHFIDKIVVEEXLNGY<br>NVRVVKLRDEIVAVTRGGLICPYTTQRIRKLYGDKLTSLFREEGELVVAGE<br>VIGLENPYVRFYYPEAGGFAYFIFDIVHGEKFLPPHERKEIVEKHGLLHVPV<br>LGEIDKNDIKAFRKIIEDLERRGREGVVLKDPEYRVPPLKYTTSFINIHDIE<br>IGMRFPFDEGRNYLFSRILREIFKAVEEGWDDRRLLLAEQNLGKAILEPAIE<br>AVKEVKNGKMLYEEFMLPEDTRDDFEEFLDYMASLGVDIIVAGVEQRSDGSI<br>VARIRKVKDTWREVQKILETGLSPID<br>Where X is any amino acid except K. | 10 | *Pyrolobus fumarii* |
| MISPELVKEALKKKKVRSEEAFGLEYLRENDDYKDIPRGTAIFKDFIIWGYP<br>HIGRIFLLETGLREQFEAPFWVEEXVDGYNTRIFKYGDNYYALSRGGFICPF<br>TTDRLPDLIDLRILDENPDLVICAEVAGPENPYIEESPPYVKEDVQLEVEDE<br>MKKNEQGFLSQEEKMELIEKYNLPHVEILGRETASEEGIKKIKEILKRENEE<br>GREGVVFKEDSERNKRAKYITSYANLMDIKTNAKNMLQLPPEYYTNRILRLV<br>LFMYEEGLKTTEHLYEELGRAFIDGLFQAIEQFEKEHKVYKTFTCKERKKEN<br>AIALLELLSKTSKHIQVKERRLEKEGDYWRLEFDKVFLNMTGLLGHLLSGGI<br>VYD<br>Where X is any amino acid except K. | 11 | *Aquifex aeolicus* |

TABLE 2

| Amino Acid Sequence | SEQ ID NO: | Species name |
|---|---|---|
| MTWIHSPESWMLDVVAEALGIDRERVEHLARHRTIRYRVERGILYASLRREV<br>AGHPEGTVIVFGRGWWRLIPGYPSIQRMVLPSVALPRHFVDKIVVEEXLNGY<br>NVRVALIDDRIIAVTRGGFICPYTTSRLERIMGNQLKDMLRELGPEEHVAAG<br>EVIGLENPYTRYFYPEAPRFGYFVFDVFREGKPLPPGWRDEVTEKHGVPHVP<br>VLGVLDKNDIEGFKKIVERLNQEGREGVIVKDPEYRVPPLKYTTPATNIGDI<br>RYGMRFFMEEGRGFLFSRLLREIFRVYEEGLTGPRLDALALELGRAALQPAI<br>ETVKKVAAGDMVYEEFELEFASRSELEEFMDYMQGLGVDLVLVEIREENGLL<br>KTRIRKMKETWLQVRKMLETGLTPID<br>Where X is any amino acid except K. | 12 | *Pyrodictium delaneyi* |
| MRRDVSQFANKLDIGKVSELLDIPEHRITGALKRKTIQYVWGKKELFRFDKP<br>VSSIEGGTSVFTEPFDIVRGFPKISRTLMLSPALQKHESSCRKVAVEEXMNG<br>YNVRVALIGDALVALTRGGFICPYTTEKAIDLIGYDFFNDHPDLVLCGEMVG<br>PDSPYVPKTFYDIESLDFFVEDIREKITGKPLSVMERRALVDKYGIKSVRLF<br>GEFEIGETHSEITRIIKDLGGSQHEGVVIKDPQMVVPPMKYTSSESNCADLR<br>YAFEFYNDFGRDFFFGRVCREAFQSVEWDEDEESVEKRCRQLGESLLLPMIK<br>TIKKKKDGERIAENVQIRVKSLDTVKEFEEYLKLVGVDAVFEEPEQTGNEYF<br>VRIRKMHQSTNDRTEAILGGQLWS<br><br>Where X is any amino acid except K. | 13 | *Candidatus Methanoperedens* |
| MTWIHRPEPWMLDVVADALGLPRERVEELASRRTLRFREFRGLLYASLRRGV<br>AGHHEGTAVVFGRGWWRVVPGYPPIQRMVLPSVALPRHELDRVVVEEXLNGY<br>NVRVVLVDDRILAVTRGGLICPYTTSRLERLMGDRLREMLRELGPEDHVAAG<br>EVIGLENPYTRYFYPEAPRFGYFVFDIFRGGRPLPPRMRDEAAEKHGVPHVP | 14 | *Pyrodictium occultum* |

TABLE 2-continued

| Amino Acid Sequence | SEQ ID NO: | Species name |
|---|---|---|
| VLGVLEKTDVEAFKRIVERLDREGREGVVVKDPDYRVPPLKYTTSSTNIGDI RLGMRFFMEEGWSFLFSRILREIFRVYEEGVEGPRLDAIALELGRAALQPAV ETVKKVAGGYMVYEEFELEFAGRDELEEFMDYMQSLGVDVVLVEAREEGGVL RARMRKIKETWIRVRRILETGVSPID Where X is any amino acid except K. | | |
| MGWVQPEPWMVDAVAEALGLERERVESLAKHRTIRFRVERGILYASLRRELG GYPEGTVVIFGRGWSRVVHGYPPIQRMVLPSVALPRHFVDRIVVEEXLNGYN VRVVLVDGRLLAVTRGGFICPYTTDRIERLLGGRLREMLRELGEEEHVAAGE VIGLENPYTRYYYPEAPRFGYFVFDIFRSGKPLPPRVRDEATEKHGVPHVPV LGVLDKGDIEGERSIVEALERRGREGVVVKDPEYRVHPLKYTTHATNVGDIR LGMRFFMEEGRGFLFSRLLREIFRAYEQGLQGPRLEKLATEIGLAALEPALE TVRLVAAGEPVYEEFELEFENRDRLEEFLEYMQSLGVDVVVAGTYERDGMLV ARVRKMRDTWLQVRRMLETGLTPID Where X is any amino acid except K. | 15 | *Thermoproteota archaeon* |
| MFVSESLGLSKHLGETLEERKILREALISHSFFSDVIEAVREDKKFGEIEEG TVVAKTINGVRIVRGFPKIKRALVLNPTLKKHFENEVAVEEXMNGYNVRIAR FGKNLYAMTRRGIICPYTTEKARELINPEFFKDHSDLVLCCEAVGEESPYVP KSMYGVEGLDFFVEDIREERTNRPLPVEEKLRLCEEYGLRHATYFGTYDVDV AHDEIKDIISDLAGKGREGVVIKDPEMKLSPLKYTTSQTNAEDLKYAFRFEN DYGKDFMESRIVREGFQSFEFNEGDKEFRERCLRLGMAILKPMVESIREVAL GGKVSEKLRLRFGSLDVMNLFFEQWKRSKVDFEITDIKKDGKDIVVFVNKTM RNTTDKIKAHLEGIPW Where X is any amino acid except K. | 16 | *Geoglobus acetivorans* |
| MKFIAEALGVSQAVIEKLNEKNLIRLAFIKHPFERDVIEAYKLERKVGEFEP GTLIAKTVEGLRVVRGYPKIKRALTLYPTIKKHFKGEVVLEEXMNGYNVRLV KFGENIYAITRGGFICPYTTEKARRLVNLDFFKDNPKLMLCCEAVGEESPFV PKDVYGVKTIDFYVEDIRDQKTNIALPIKQKEKLAEEYGLKLAPILAEVQVS KAHEIAKEIILELDKRGREGIVIKDPMMRRPPIKYTTSQCNCSDLSYAFRFF EEYGKDEMESRIIREAFQSFEFRENEEKFKDRCLRLGEAILSMVKSIKEVNE GKRIVEKMRLRFYDLEIFELFKEHIRRMGIRAEFSNPKREEDGYVVWVYRHI MSTTDKIKYILAGNLY Where X is any amino acid except K. | 17 | *Archaeoglobus profundus* |
| MVSSHFKSLLLELGISRERIEILESKGGIVEDEFEGIRYLRFKDSAGSLRRG TVVFDSHNIILGFPHIKRVVHLENGIKRVFKRKPFYVEEXVDGYNIRVAQIE GRVFAFTRGGFVCPFTTERIEDFVNMEFFKDYPNLVLCGEMAGPESPYLVEG PPYVKEDIEFFLFDIQEKKTGKSLTVEERLKIAEEYGIPSVEVFGVYDISKI DELKELIEQLSREKREGIVMKSPDMKKIVKYVTPYANVNDIKIGARIFFDLP HGYFMQRIKRLAFYLAEKRVQDEEFEKYARALGRALLEPFVESIWDVSAGEE IAEVFTVRVKHIETAYKMVSHFERLGLKIHIEDIEEMPQGYWRITFKRVYPD ATREIRELWSGHAFVD Where X is any amino acid except K. | 18 | *Thermococcus litoralis* |
| MVSSRFKDILTSLGISEERIEILEAKGGIVEDEYEGLRYLRFKDSAGKLRRG TVVFDFDKIILGFPHIKRVVNLEKGIRRIFKRGEFYVEEXVDGYNVRVTKVG ERILAITRGGFICPFTTERITDFVPEEFFKDNPNLVLVGEMAGPESPYLVEG PPYVKEDIKFFLEDVQEINTGKSLPVEERLKLAEEYGIPHVEVFGKYTRDDI GELYALIEKLSEEGREGIVMKSPDMKKIVKYVTPYANINDIKIGARVFYELP PGYFTSRISRLAFYIAERKIRDEELRKLAEDLGKALLQPFVEGILDVEQGEE IAETFKIRVKKIETAYKMVTHFEKLGLNIEIVDIEEMDGLWRITEKRVYSDA TEKIKELVGGKAFVD Where X is any amino acid except K. | 19 | *Pyrococcus sp.* ST04 |
| MKSERGIMKYKDFIYYPFKKGGFGKGSVIIYHNDDVKIVPGYPSIKRLVLLS KVPEHFPEGVSVEEXMNGYNVRAMIVGGDVAFITRGGYLCPYTNARLNTLYG EKVKALLEELPPGSFLAGEVVGVENPYVRVKYPEAPYFDYFIFDIFVKTEDG WRQMPVEERHEIVKRHGLRSVRLLGTFESSEAPLKIKEIIDREDKEGREGVV MKDPEYKRSPAKYTGSYTNIGDIREGMRYPFDEGKDYLFPRIVREIFKVYEE GLSDKELERRALELGMAILKPAVESLKEVAQGETLFERFVLRFPHEEDLEEY LNYTRSLGVKVIVEEKWEEGEWIVVKAKKFKNTSNVYRSMLKSGQTPLD Where X is any amino acid except K. | 20 | *Ignicoccus pacificus* DSM 13166 |
| MVSSYFKGILLNLGLDEERIEVLENKGGIVEDEFEGMRYLRLKDSARSLRRG TVVEDEHNIILGFPHIKRVVQLENGIRRAFKRKPFYVEEXVDGYNVRVAKIG EKILVFTRGGFVCPFTTERIEDFITLDFFKDYPNMVLCGEMAGPESPYLVEG PPYVKEDIQFFLEDIQEKKTGRSLPVEERLKLAEEYGIPSVEVEGLYDLSRI DELHALIDRLTKEKREGIVMKSPDMKKIVKYVTPYANINDIKIGARIFFDLP HGYFMQRIKRLAFYLAERKIRGEEFDEYARALGKVLLEPFVESIWDISSGDD EIAELFTVRVKKLETAHKMVTHFERLRLKIHIDDIEVLDNGYWRITEKRVYP DATKEMRELWNGHAFVD Where X is any amino acid except K. | 21 | *Palaeococcus pacificus* |

In some embodiments, the sequences in Table 1 or above are used to perform a sequence search (e.g., using BLAST or PSI-BLAST) to find other thermostable ssDNA/RNA ligases from other species (e.g., by finding those with 30% . . . 50% . . . 60% or more homology). For a particular candidate homolog that is identified, the next step is to find out the growth temperature of the species it is from. In general, a useful single strand ligase candidate would come from a species that has a growth temperature range higher than about 65° C. Next, one can perform a multiple sequence alignment, and locate the conserved catalytic motif, EKxxG (x is any amino acid; such as shown in Tables 1 and 2 above). Next, within the catalytic motif, mutate K to any other amino acid (e.g., to make a step 3 ligase mutant). In certain embodiments, the lysine (K) in such Motif I is mutated to another amino acid, preferably an alanine (A), serine(S), cysteine (C), valine (V), threonine (T), and Glycine (G). Such candidate enzymes (e.g., mutant enzymes) can then be screened for ssDNA and ssRNA activities (and thermostability), for example, using the same procedure as in Example 1 below (e.g., replacing the step 3 ligase mutant in Example 1 with the candidate mutant and measure performance).

In certain embodiments, the single stranded adaptors disclosed herein are used in library preparation ("library prep") and/or then in sequencing methods, such as in attaching adaptors to library fragments for subsequent sequencing. For example, in some embodiments, the disclosure provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), sequence-by-binding, semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety.

Any number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the present disclosure finds use in automated sequencing techniques understood in that art. In some embodiments, the present technology finds use in parallel sequencing of partitioned amplicons (PCT Publication No: WO2006084132, herein incorporated by reference in its entirety). In some embodiments, the technology finds use in DNA sequencing by parallel oligonucleotide extension (See, e.g., U.S. Pat. Nos. 5,750,341, and 6,306,597, both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485, 944, 6,511,803; all of which are herein incorporated by reference in their entireties), the 454 picotiter pyrosequencing technology (Margulies et al., 2005 Nature 437, 376-380; US20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; all of which are herein incorporated by reference in their entireties), and the Adessi PCR colony technology (Adessi et al. (2000). Nucleic Acid Res. 28, E87; WO 00018957; herein incorporated by reference in its entirety). In certain embodiments, the library preparation and sequencing technologies are as described in any of the following U.S. patents, each of which is herein incorporated by reference: U.S. Pat. Nos. 9,752,188; 10,570,451; 11,479,807; 8,383,345; 10,876,172; 9,598,731; 9,902,992; 10,801,063; 11,091,797; 8,532,930; 9,639,657; and 10,011,870.

In certain embodiments, the 3' end of the single-stranded adaptors here have a 3' end blocking group such as a phosphate group or a modified noncanonical nucleotide to prevent ligation between the 5'-adenylated end and 3' end of the adaptor. If the blocking group is, for example, a nucleotide with 3'-phosphate, such blocking group can be removed by T4 polynucleotide kinase, calf intestinal alkaline phosphatase (CIP), or shrimp alkaline phosphatase (SAP). In certain embodiments, where CIP or SAP are used, one may employ a round of T4 PNK to re-phosphorylate the 5'-end of the proximal strand.

Another class of the base blockers and de-blocking can leverage reversible terminator technologies widely used in the sequencing industry.

In certain embodiments, the single-strand adaptors herein comprises a non-canonical base in the cleavable region, such as inosine, uracil, 5-formylcytosine, 5-carboxylcytosine, or 8-oxoguanine. In some embodiments, wherein inosine is present in the cleavable region, Endonuclease V or similar enzyme is used to perform strand cleavage. In certain embodiments, wherein uracil, 5-formylcytosine, or 5-carboxylcytosine is present in the cleavage region, a combination of uracil DNA glycosylase (UDG) and Endonuclease VIII (or similar enzymes) are employed for strand cleavage. In particular embodiments, where 8-oxoguanine is present in the cleavable region, a thermostable OGG (oxoguanine glycosylase) is employed or strand cleavage. In particular embodiment, a cleavable backbone linkage can be, for example, phosphorothioate DNA and cleaved by iodine ($I_2$) (Qiang Huang et al. Origin of iodine preferential attack at sulfur in phosphorothioate and subsequent P—O or P—S bond dissociation, PNAS, vol 119, 2022).

In particular embodiments, the cleavable region is cut with an endonuclease. For example, a secondary oligo (as shown in FIG. 11C) is added to the sample and hybridizes to the single strand adaptor and creates a cleavage site in the cleavable region (e.g., which can be cleaved by a restriction endonuclease). In some embodiments, while most of the single strand adaptor is composed of DNA, the cleavage region contains one or more RNA bases, allowing cleavage by an Rnase H, Rnase H2, or site-specific endonuclease.

In certain embodiments, the methods and compositions preserve methylation on 3' and 5' protruding ends of target DNA as, for example, no end-repair or A-tailing is required of the target DNA. Conventional library prep uses end-repair and A-tailing (ER/AT) step as part of its workflow. The enzymatic reactions in ER/AT "write" to the starting DNA templates by filling in the 3'-recessed ends or "erase" to the starting DNA template by removing the 3'-protruding ends, as shown in FIG. 16A, losing information about potential methylation in protruding ends. The DNA patches that are filled in during this step are void of biologically relevant base modification, such as 5-methylcytosine (5mC), 5-hydroxylmethylcytosine (5hmC) etc. As a result, they introduce dilution effect to the CpG sites near the ends of the template DNA. Such artifacts exist extensively in conventional genome-wide methyl-seq results (see, e.g., Jiang et al., Genome Res. 2020 August; 30(8): 1144-1153, herein incorporated by reference, particularly FIG. 1). As the methods and compositions herein do not require ER/AT, no "writing" is involved during the library preparation process. As the result, no artifactual DNA patches are introduced during the library preparation workflow and high-fidelity methylome data can be obtained (e.g., by bisulfite and similar methods). In other words, as most methods rely on bisulfite conversion of DNA to detect unmethylated cytosines (which changes unmethylated cytosines to uracil during library preparation), converted bases are identified (after PCR) as thymine in the sequencing data, and read counts are used to determine the % methylated cytosines. Thus, the methods and compositions herein allow for a more realistic and higher fidelity methylation detection (e.g., which has implications for more accurate cancer detection).

In certain embodiments, the first and/or second nucleic acid sequence (e.g., that make up the adapters) is/are methylated at every (or almost every) cytosine present. In certain embodiments, the methylation is 5-methylcytosine (5mC) and/or 5-hydroxylmethylcytosine (5hmC). Such methylation, for example, can be introduced during synthesis of the nucleic acid sequences. During bisulfite conversion (e.g., as part of bisulfite sequencing methods herein) 5'-methylcytosine (or 5hmC) will not be converted during the conversion step while unmodified cytosine will be converted to uracil. The conversion can either be chemical based (such as bisulfite conversion) or enzyme based (such as EM-seq). Methylation of the nucleic acid sequences herein prevents, for example, any elements present in the adapters (such as flow cell binding sequences and universal primer binding sites) from having their sequences changed during bisulfite conversion (or other conversion). In this regard, the adapter sequences can still bind to universal primers employed and can still bind to flow cell sequences (e.g., such as in Illumina sequencers). An exemplary workflow employing such methylated nucleic acid sequences is shown in FIG. 16B.

In certain embodiments, rolling circle amplification is performed instead of PCR amplification, as shown in FIGS. 18A and 18B. In FIG. 18A, after the first and second adaptors are ligated onto the duplex DNA molecule and dumbbell loop structures are formed, a primer that is designed to anneal to the adaptor sequence is added to initiate rolling-circle amplification (RCA), to generate concatenated single-strand DNA with multiple copies of the duplex DNA templates. In FIG. 18B, after the first and second adaptors are ligated to the duplex DNA molecule, duplex DNA is denatured and subject to deblocking/ligation, so that each strand forms single strand circles with the adaptor sequence embedded inside. A primer that is designed to anneal to the adaptor sequence is added to initiate rolling-circle amplification (RCA), to generate concatenated single-strand DNA with multiple copies of the strand-specific DNA templates.

EXPERIMENTAL

Example 1

Single-Stranded End-Preserving Adaptors for
Library Preparation

In this Example, a library preparation approach (DISTAL-seq adaptor ligation and sequencing methods) is illustrated based on a ligation schema termed "duplex-retaining single strand tail ligation" (DISTAL adaptor ligation methods). In certain embodiments of DISTAL adaptor ligation methods, a 5'-adenylated single strand adaptor DNA is ligated to the 3'-ends of the duplex DNA at elevated temperature (e.g., 75° C.) catalyzed by a step 3 ligase mutant (hyperligase in this example), with the DNA duplex still retained (see, FIGS. 1 and 2A). After DISTAL adaptor ligation methods, since the 3'-end of the adaptor is brought to the proximity of the 5'-end of the duplex DNA, a more efficient intramolecular ligation is readily feasible. The resulting "dumb-bell"-shaped DNA can then be processed for PCR enrichment (FIG. 2A). A unique feature of embodiments of the DISTAL-seq adaptor ligation and sequencing methods is that the ligations at the 5'-ends and the 3'-ends of the library duplex DNA occur in single strand form, so that conventional ER/AT is not necessary.

Based on embodiments of DISTAL-seq adaptor ligation and sequencing methods, DUET-seq adaptor ligation and sequencing methods adaptor ligation and sequencing methods (duplex end restoration sequencing) was developed by incorporating strand-specific unique molecular identifiers (UMIs, aka barcodes which can be unique or non-unique) into the single strand adaptor, so that a portion of the resulting reads can be paired to its original duplex form (FIG. 3A). As a result of the strand pairing, native DNA ends are also restored. For validation, certain embodiments of DUET-seq adaptor ligation and sequencing methods adaptor ligation and sequencing methods were shown to recover known DNA ends with no strand swapping from a pool of restriction enzyme digested DNA. Embodiments of DUET-seq adaptor ligation and sequencing methods adaptor ligation and sequencing methods was then used to compare the end profiles between sonicated genomic DNA and enzymatically fragmented DNA, and revealed that while ends of the sonicated DNA can be either 5'-single-strand protruding or 3'-single-strand protruding with equal probability and tend to be rather short, ends from enzymatically fragmentation are predominantly 3'-single-strand protruding and have a wider length distribution. Finally, embodiments of DUET-seq adaptor ligation and sequencing methods adaptor ligation and sequencing methods was applied to a cell free plasma DNA sample, for which the ends are generated and polished from an in vivo setting. Intriguingly, predominantly 3'-single-strand protruding ends are discovered in the cell free plasma DNA.

In summary, this example demonstrates the principles and utilities of certain embodiments of DISTAL adaptor ligation methods, and the library preparation workflows (embodiments of DISTAL-seq adaptor ligation and sequencing methods and DUET-seq adaptor ligation and sequencing methods adaptor ligation and sequencing methods) that starts with it. These methods provide advantageous alternatives to the conventional ER/AT-based NGS preparation methods.

METHODS AND MATERIALS

Single-Strand Adaptor Preparation

Two types of single-strand adaptors were prepared and used in this example, one for an embodiment of regular DISTAL-seq adaptor ligation and sequencing methods workflow and one for duplex end-restoration sequencing (DUET-seq adaptor ligation and sequencing methods adaptor ligation and sequencing methods), as listed in Table 3. All oligos were order from Integrated DNA Technologies (IDT). All oligo purification was done by using Monarch DNA purification kit (NEB). For AMPure® DNA binding beads clean-up, AMPure XP beads were purchased from Beckman-Coulter.

glycosylase and Endo VIII) was then used to cleave at the dU site and generate the 3'-phosphate end. This is done by mixing 26 ul extended dupada_3, 3 ul 10× T4 ligase buffer

TABLE 3

| Single-strand adaptor oligos and PCR primers used in this example | | | |
|---|---|---|---|
| Name | sequence | SEQ ID NO: | Purification |
| ILMNAda2 | NNNNNAGATCGGAAGAGCACACGTCTGAACTCCAGTCAC/ ideoxyU/ACACTCTTTCCCTACACGACGCTCTTCCGATCTNNNNN/ 3Phos/ | 22 | HPLC |
| dupada_3 | GTCGABBBBBBBBAGATCGGAAGAGCACACGTCTGAACTCCAG TCAC/ideoxyI/TACACTCTTTCCCTACACGACGCTCTTCCGATCT | 23 | HPLC |
| pBR322_ 4288F | ACTCTTCCTTTTTCAATATTATTGAAG | 24 | Desalted |
| pBR322_ 85R | ACACGGTGCCTGACTGCGTTAGCAATTTAAC | 25 | Desalted |
| pBR322_ 4320R | AGGTTAATGTCATGATAATAATGGTTTC | 26 | Desalted |
| lambda_ 4500F | GGGTTTTCTTTTGTGCGCTTGCAGGCCAGC | 27 | Desalted |
| lambda_ 4800R | AGCAGAATGCCGTCCACCATCGGATCGCTGG | 28 | Desalted |
| lambda_ 4500F_ 3'res | GGGTTTCCTCAGCTCTTTTGTGCGCTTGCAGGCCAGC | 29 | Desalted |
| lambda_ 4800R_ 3'res | AGCAGAACCTCAGCTGCCGTCCACCATCGGATCGCTGG | 30 | Desalted |
| lambda_ 4500F_ 5'res | GGGTTTTGCTGAGGCTTTTGTGCGCTTGCAGGCCAGC | 31 | Desalted |
| lambda_ 4800R_ 5'res | AGCAGAATGCTGAGGGCCGTCCACCATCGGATCGCTGG | 32 | Desalted |

1. List of base modifications: /ideoxyU/: internal dU; /idoxylI/: internal dI; /3Phos/: 3'- phosphate; B = C/G/A; N = A/C/G/T
2. Underline sites denote Nb.BbVCI recognition sites.

To prepare a DISTAL-seq adaptor ligation and sequencing methods adaptor, ILMNAda2 (Table 3) was resuspended in water to 20 uM. 5'-phosporylation was done by mixing 26 ul ILMNAda2, 3 ul 10× T4 ligase buffer (NEB) and 1 ul T4 polynucleotide kinase (3' phosphatase minus) (NEB). Reaction was incubated at 37° C. for 1 hour and column purified with 30 ul elution volume. 5'-adenylation was done by using 5'-adenylation kit (NEB), by mixing 6 ul phosphorylated ILMNAda2, 2 ul 10× adenylation buffer, 2 ul of 1 mM ATP, and 2 ul Mth RNA ligase in 20 ul reaction volume. Reaction was incubated at 65° C. for 1 hour and heat-inactivated at 85° C. for 5 minutes. Reaction was then column purified with 10 ul elution volume in low-TE buffer.

For an exemplary DUET-seq adaptor ligation and sequencing methods adaptor ligation and sequencing methods adaptor, dupada_3 (Table 3) was first resuspended in water to 20 uM. 3'-extension was done by mixing 26 ul dupada_3, 5 ul 10× reaction buffer, 1 ul dA/U/C/GTP mix (10 mM each), 1 ul Taq-Klenow (cat #TT-100, MCLAB) in a total volume of 50 ul. Extension reaction was programmed to first heat to 95° C. for 1 min, and then 68° C. for 10 min. Reaction was column purified with 26 ul elution volume. Since the extension will incorporate a single dU in the newly synthesized 3' end, USER reagent (NEB) (uracil DNA (NEB), 1 ul T4 polynucleotide kinase (3' phosphatase minus) (NEB) and 0.5 ul USER reagent (uracil DNA glycosylase and Endo VIII). Reaction was incubated at 37° C. for 40 min and column purified with 25 ul elution volume. 5'-adenylation was done similarly as above with the 5'-adenylation kit (NEB), by mixing 6 ul 5'- and 3'-phosphorylated dupada_3, 2 ul 10× adenylation buffer, 2 ul of 1 mM ATP, and 2 ul Mth RNA ligase in 20 ul reaction volume. Reaction was incubated at 65° C. for 1 hour and heat-inactivated at 85° C. for 5 minutes, and was then column purified with 10 ul elution volume in low-TE buffer.

DISTAL Adaptor Ligation Methods and DNA Substrate Preparation

Purified HyperLigase is from RGENE Inc. (10). Cloning and purification of HyperLigase was described earlier in (10, herein incorporated by reference).

A typical 50 ul HyperLigase ligation is composed of: 5 ul 10× HyperLigase reaction buffer (700 mM Tris, pH=7.5), 5 ul MnCl₂ (100 mM), 5 ul adenylated adaptor (10 uM), 15 ul 40% (w/v) PEG8000, 1.5 ul 5M NaCl, 2.5 ul purified HyperLigase and 15 ul input sample solution containing duplex DNA. Reactions are incubated in PCR machine at 75° C. (with heated lid on) for 6 hours. Reaction series in FIG. 1 were incubated at various temperature in separate runs (not with gradient option). Reactions were then purified twice using 1× bead clean-up and run on TAPESTATION automated electrophoresis system using High sensitivity D1000 screentape (Agilent). For reaction using thermostable App DNA ligase (cat #M0319, NEB), reaction was set up according to manufacturer's recommendation and incubated at 65° C. for 6 hours.

For DNA duplex substrates used in FIG. 1, primers were designed based on pBR322 sequence (Table 3). pBR322_4280F and pBR322_4360R were used to generate ~180 bp amplicon and pBR322_4280F and pBR322_85R were used to generate ~320 bp amplicon. PCRs were done by using Taq2× master mix (cat #M0270, NEB) and followed manufacturer's recommended protocol. To generate duplex DNA with defined 3'-single-strand protruding and 5'-single-strand protruding ends, PCRs using lambda_4500F_3'res/lambda_4800R_3'res, and lambda_4500F_5'res/lambda_4800R_5'res as primers, lambda DNA as the template, were done separately. Purified PCR products were then subject to Nb.BbVCI (NEB) digestion at 37° C. for 2 hours. Purified digested DNA with defined 3'-single-strand protruding and 5'-single-strand protruding ends were then used in DISTAL adaptor ligation methods. Blunt-ended duplex DNA were generated by using lambda_4500F/lambda_4800R as PCR primers, purified and used in DISTAL adaptor ligation methods.

DISTAL-Seq Adaptor Ligation and Sequencing Methods and DUET-Seq Adaptor Ligation and Sequencing Methods Adaptor Ligation and Sequencing Methods Library Preparation Genomic DNA of *E. coli* O157 strain EDL933 was ordered from Sigma (cat #IRMM449). Human genomic DNA extracted from blood (buffy coat) was purchased from Sigma (cat #11691112001, Roche). Human cell-free plasma DNA was purchased from PlasmaLab International (Everett, WA). Fragmentation was either done by using Covaris ultrasonicator M220 model or by using NEBNext® library prep kit dsDNA fragmentase (NEB cat #M0348) following manufacturer's instructions. For sonicated genomic DNA, an extra round of end polishing was done by treating DNA with T4 polynulceotide kinase (PNK) in the T4 ligase buffer and purified by bead clean-up.

In this example, exemplary DISTAL-seq adaptor ligation and sequencing methods and DUET-seq adaptor ligation and sequencing methods adaptor ligation and sequencing methods start directly with hyperligase ligation using 50 ng fragmented DNA. Briefly, 50 ul reaction consists of: 5 ul 10× reaction buffer, 5ul MnCl$_2$, 2.5 ul HyperLigase, 15 ul 40% (w/v) PEG8000, 5 ul adaptor, 1.5 ul 5M NaCl, and 15 ul DNA solution. Reaction was incubated at 75° C. for 6 hours and purified by 2 rounds of 1× AMPure DNA binding beads clean-up with elution volume of 26 ul in water. De-blocking of the adaptor 3'-ends was done by using 26 ul DNA from the previous step, 3 ul 10× T4 ligase buffer, and 1 ul T4 PNK. Reaction was incubated at 37° C. for 40 min, after which another 1× beads clean-up was done to the reaction mix with elution volume of 10 ul. Circularization was done by using 10 ul DNA solution from the previous step, 1 ul 10× circligase reaction buffer, 0.5 ul CircLigase II and 0.5 ul MnC12 (Biosearch Technologies, cat #CL9021). Reaction was incubated at 60° C. for 1 hour, after which another 1× AMPure DNA binding beads clean-up was done with elution volume of 18 ul. "Dumb-bell" DNA digestion is done by using 18 ul DNA solution from the previous step, 2 ul of 10× rCutSmart, and 0.2 ul of endonuclease. For regular DISTAL-seq adaptor ligation and sequencing methods, in which internal dU is embedded within the adaptor, USER reagent (uracil DNA glycosylase and Endo VIII) was used; for DUET-seq adaptor ligation and sequencing methods adaptor ligation and sequencing methods, in which internal dI is embedded within the adaptor, Endonuclease V was used (cat #M0305, NEB). Digestion reaction was incubated at 37° C. for 15 min followed with heat-inactivation at 65° C. for 20 min. For PCR enrichment. 25 ul of Kapa HiFi HotStart ReadyMix (KR0370, Roche Sequencing) and 5 ul UDI primer mix (part number 10005922, IDT) were added to the digestion reaction mix. PCR conditions followed manufacturer's protocol. For *E. coli* library, 12 cycles were performed; for DUET-seq adaptor ligation and sequencing methods adaptor ligation and sequencing methods, 16 cycles were performed. After PCR, purification was done by 0.9× beads clean-up.

Sequencing and Data Analysis

All libraries were quantified by qPCR (KR0405, Roche Sequencing) and pooled based on library concentration and planned read allocation. Sequencing was carried out 2×151 cycles on an Illumina NextSeq 500 using a High-output kit according to manufacturer's protocol.

Programs and commands with parameters to process the read data is listed in Table 4.

TABLE 4

| | Computational programs and commands for analysis | |
|---|---|---|
| Programs | Commands | notes |
| Trimmomatic | java -jar ~/Trimmomatic-0.39/trimmomatic-0.39.jar PE s7__R1.fastq.gz s7__R2.fastq.gz s7__paired__R1.fq.gz output__forward__unpaired.fq.gz s7__paired__R2.fq.gz output__reverse__unpaired.fq.gz ILLUMINACLIP:TruSeq3-PE.fa:2:30:10:2: True LEADING: 3 TRAILING: 3 MINLEN: 36 | Read trimming. S7 is the representative sample used. |
| Picard | picard FastqToSam F1=s7__paired__R1.fq.gz F2=s7__paired__R2.fq.gz O=s7__unaligned.bam SM=s7 | Merge read 1 and read2 |
| Fgbio | java -jar ~/picard/fgbio-2.2.0.jar ExtractUmisFromBam --input=s7__unaligned.bam --output=s7__unaligned__withumi.bam --read-structure=8M143T 13M138T --molecular-index-tags=ZA ZB --single-tag=RX | Extract UMIs from reads |
| picard | picard SamToFastq I=s7__unaligned__withumi.bam F=s7__unaligned__withumi.fastq INTERLEAVE=TRUE | regenerate fastq read file |
| Bwa | bwa mem -t 4 -p ~/reference/human/GCA__000001405.15__GRCh38__no__alt__analysis__set.fna s7__unaligned__withumi.fastq -o s7__aligned__withoutumi.sam | Alignment to reference |
| samtools | samtools view s7__aligned__withoutumi.sam -b -o s7__aligned__withoutumi.bam | Conversion of sam to bam |

TABLE 4-continued

| Computational programs and commands for analysis | | |
|---|---|---|
| Programs | Commands | notes |
| picard | picard MergeBamAlignment UNMAPPED=s7_unaligned_withumi.bam ALIGNED=s7_aligned_withoutumi.bam O=s7_aligned_withumi.bam R=/home/zhengyuhudson/reference/human/GCA_000001405.15_GRCh38_no_alt_analy sis_set.fna SO=coordinate ALIGNER_PROPER_PAIR_FLAGS=true MAX_GAPS=−1 ORIENTATIONS=FR VALIDATION_STRINGENCY=SILENT CREATE_INDEX=true | Merge bam, adding UMI info back |
| picard | picard MarkDuplicates I=s7_aligned_withumi.bam O=markduplicates_umi.bam M=markduplicates.txt BARCODE_TAG=RX REMOVE_DUPLICATES=true | De-deplication |

Briefly, adaptor sequences and polyG sequences were first trimmed off reads by using Trimmomatic (11). Reads were then aligned to the reference genomes by using bwa (12) and files were processed with samtools (13). Alignment statistics were generated by Picard tools (14). UMI-aware read processing was done by using fgbio (15). Customary scripts for pairing duplex strands and end restoration were written using PERL scipt within PERL programming language.

RESULTS

Biochemical Characteristics of DISTAL Adaptor Ligation Methods

In this Example, DISTAL adaptor ligation methods is catalyzed by a mutant thermostable single strand ligase (named "HyperLigase"), which originates from *Hyperthermus butilycus*, a hyperthermophilic archaebacterium that grows optimally between 95° C. and 106° C. (16). A lysine to alanine mutation was introduced at the catalytic site so that the mutant ligase is only capable of ligation between a 5'-adenylated end and a 3'-hydroxyl end of single strand DNA/RNA at elevated temperature (up to 95° C.) (10). Another mutant ligase (thermostable Mth App ligase, NEB cat #0319) from *Methanobacterium* thermoautotrophicum, with optimal reaction temperature at 65° C., was reported in (17) and also tested in this example.

Although the 3'-hydroxyl end is typically provided by a single strand DNA, the hypothesis tested here is on whether duplex DNA, with duplexes at the ends transiently separating into single strand conformation due to thermodynamics ("DNA breathing" (18)), can facilitate ligation at the 3'-ends catalyzed by the single strand DNA ligases. The duplex is ideally retained before and after the ligation (hence the name), with the benefits of retaining strand pairing signals for the later end restoration (see below DUET-seq adaptor ligation and sequencing methods adaptor ligation and sequencing methods).

To test the impact of the reaction temperature, DISTAL adaptor ligation methods reactions were set up and incubated at various temperature for 6 hours (FIG. 1). As shown in FIG. 1A, both one-sided ligation product and two-sided ligation product can be readily seen above the starting duplex DNA substrate, which is around 320 bp (lane 8, FIG. 1A). This first observation demonstrates that hyperligase ligation is clearly feasible at elevated temperature. The intensity of the two-sided ligation product band peaks at 75° C. and starts to decrease at either higher or lower temperature. When the reaction temperature drops below 70° C., the ligation reaction becomes inefficient so that there is almost no observable two-sided ligation product (FIG. 1A). Similar experimental set up was repeated for a duplex DNA of different size (~180 bp). FIG. 1B shows that in general same trends hold for the smaller-sized duplex DNA. The testing of hyperligase ligation near the 180 bp range is important because for some type of DNA, such as cell free plasma DNA, majority of the fragments may fall into the vicinity of that size range.

As a comparison, the thermostable Mth App ligase (NEB) was used to test ligation between duplex DNA and single strand DNA at 65° C. for 6 hours. However, almost no ligation products can be observed (lane 9, FIG. 1A). This observation, together with the low ligation efficiency below 70° C. observed for HyperLigase (FIG. 1AB), further supports the importance of reaction temperature.

The quantitative conversion efficiency of hyperligase ligation, as measured by the percentage of conversion from substrate to either one-sided or two-sided ligation product is shown in FIG. 1C. At 75° C., more than 80% of the duplex DNA can be ligated either at one end or at both ends, with 30-40% being two-sided and 40-50% being one-sided (FIG. 1C). Since only two-sided product will be efficiently amplified during PCR (DISTAL-seq adaptor ligation and sequencing methods, FIG. 2A), it suggests, for the conditions in this example, a ceiling of about 30% to 40% of the duplex DNA fragments that are converted to sequencable DNA templates. Time-course experiments suggest that ligation products keep accumulating over time but appear to reach a plateau after 6-8 hours (data not shown).

A notable feature of the hyperligase ligation in FIG. 1 is that ligation can only occur between 5'-adenylated end of the single strand adaptor DNA and the 3'-hydroxyl end of the duplex DNA. The 3'-end of the single strand adaptor DNA is modified (3'-phosphate in this example) so that self-circularization or cross concatenation of the adaptor is blocked. There is no added ATP in the ligation reaction so that no additional 5'-adenylated ends can be generated, which also precludes ligation among the input DNA themselves, whether in a single strand or in a duplex form. The uni-direction feature of the hyperligase ligation increases efficiency as well as preventing sequencing artifacts due to the formation of chimeras.

To investigate the potential impact of end configuration to hyperligase ligation, duplex DNA with 5'-single-strand protruding end or 3'-single-strand protruding end were prepared by subjecting blunt end PCR DNA to nicking enzyme (Nb.BbVCI) digestion. Nicking enzyme recognition sites were introduced from the primers used in PCR (Table 3). After digestion, 5'-single-strand protruding ends have 9-10 nt single strand portion while 3'-single-strand protruding ends have 11-12 nt on either side of the duplex DNA. The digested DNA were then used as substrate for hyperligase ligation, and compared with blunt end DNA, as shown in FIG. 5. The results there show that hyperligase ligation does not exhibit bias for the ends tested. This conclusion provides support that hyperligase ligation can be used to attach adaptor to the 3'-ends of a complex library with heterogenous DNA end configuration.

DISTAL Adaptor Ligation Methods Enable Sequencing Library Preparation (DISTAL-Seq Adaptor Ligation and Sequencing Methods)

FIG. 2A illustrate a sequencing library preparation workflow based on DISTAL adaptor ligation methods (DISTAL-seq adaptor ligation and sequencing methods), which can be grouped into 4 stages: (1) hyperligase ligation, in which 5'-adenylated single strand adaptor is ligated to the 3'-end of the duplex library DNA; (2) adaptor 3'-end deblocking, during which the phosphate group at the 3'-end of the adaptor is removed by the phosphatase activity of the T4 PNK. Other DNA phosphatases can be used for this purpose as well (data not shown). (3) circular ligation between the proximal 5'- and 3'-ends by the single strand DNA/RNA ligase CircLigaseII. Similar to hyperligase ligation, this ligation step occurs at elevated temperature (60° C.). The difference is that instead of being inter-molecular for hyperligase ligation, this ligation is intra-molecular; (4) Cleavage of the adaptor at pre-designed site by endonucleases, and followed by PCR enrichment (FIG. 2A).

Figure 6:
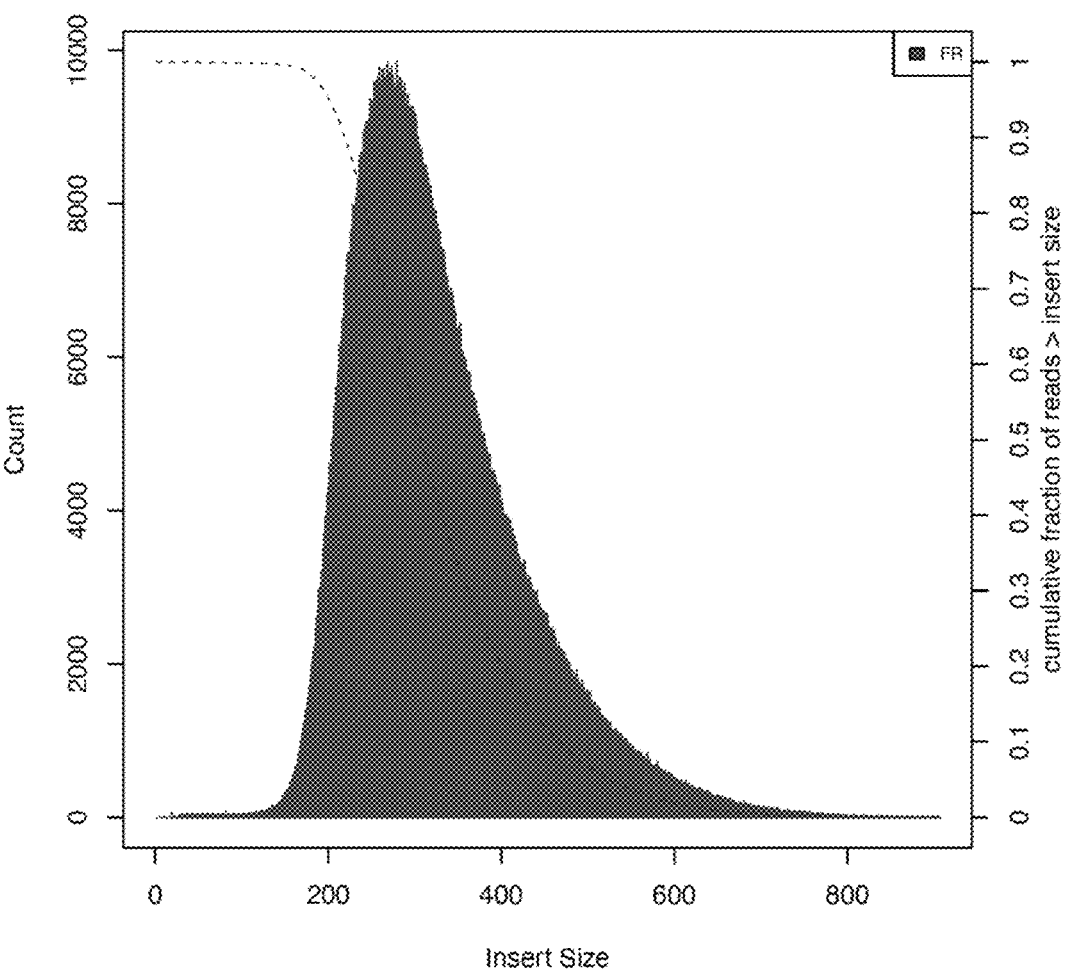
FIG. 6. Insert size distribution of the exemplary *E. coli* DISTAL-seq adaptor ligation and sequencing methods library. The figure was generated by using CollectInsertSizeMetrics in Picard tools.
Figure 7:
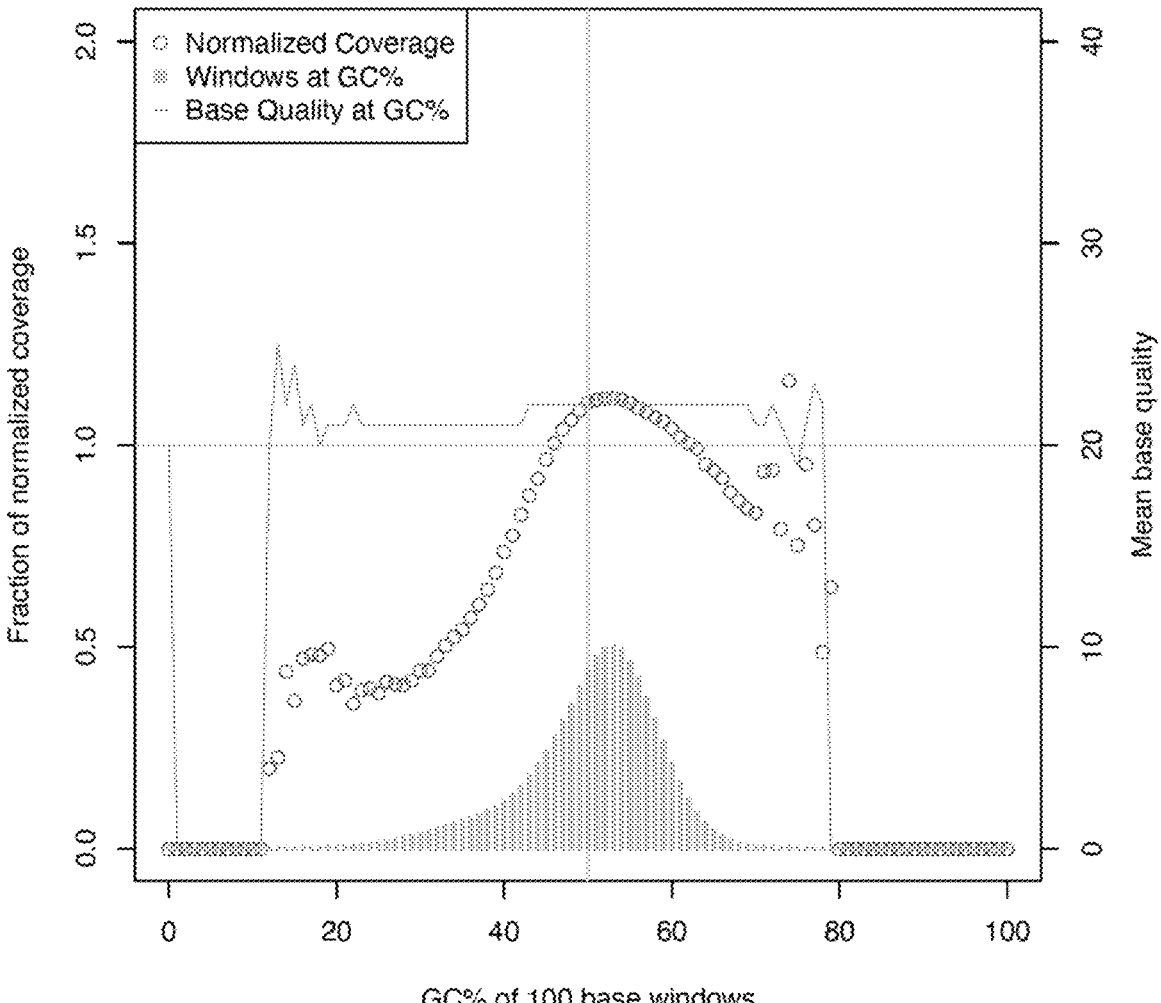
FIG. 7. GC bias for the exemplary *E. coli* DISTAL-seq adaptor ligation and sequencing methods library. The plot is generated by CollectGcBiasMetrics in Picard tools.

As a proof of principle experiment, library from 50 ng of reference material *Escherichia coli* 0157 (EDL933) gDNA was made using the DISTAL-seq adaptor ligation and sequencing methods workflow (FIG. 2AB) and sequenced. Approximately 4.8 million of pair-end reads (2.4 million of each direction) were obtained and aligned to the reference genome. The mean coverage is around 85× and the median coverage is around 95× (FIG. 2C). The read mapping is of high quality, with low error rate (PF_HQ_ERROR_RATE=0.0064, PF_INDEL_RATE=0.00010) and low chimera rate (PCT_CHIMERAS=0.003. All metrics were reported by CollectAlignmentMetrics in Picard Tools). FIG. 6 shows the distribution of insert sizes, which is consistent with the intended 300 bp size range during sonication. A moderate level of GC-bias is observed for both high-GC and low-GC bins, with normalized coverage dropping to around 0.5 at either extreme (FIG. 7). Nevertheless, the GC-bias does not appear to impact the overall coverage uniformity significantly since >90% of the bases are covered with more than 0.2× of the mean coverage (17×) (FIG. 2D).

To investigate the sequence-specific bias of both hyperligase ligation and circular ligation, stretches of randomized nucleotides (NNNNN, N=A/T/C/G) were designed at both 5'- and 3'-ends of the single strand adaptor. Mapped read1 and read2 of the *E. coli* DISTAL-seq adaptor ligation and sequencing methods data were aligned and sequence context on either side of the ligation junction was analyzed for potential bias (FIG. 2C). As shown in FIG. 2C, no significant sequence bias is present at the ligation junction on the side of the genomic insert. There is slight sequence bias present on the adaptor side for either DISTAL adaptor ligation methods or for the circular ligation, which should not be concerning and could be associated with the synthetic degenerate adaptor itself. In addition, having the degenerate regions at both ends of the adaptor provides additional utility of serving as unique molecular identifiers (UMIs) and can be used for further error suppression (FIG. 2D).

Figure 8:
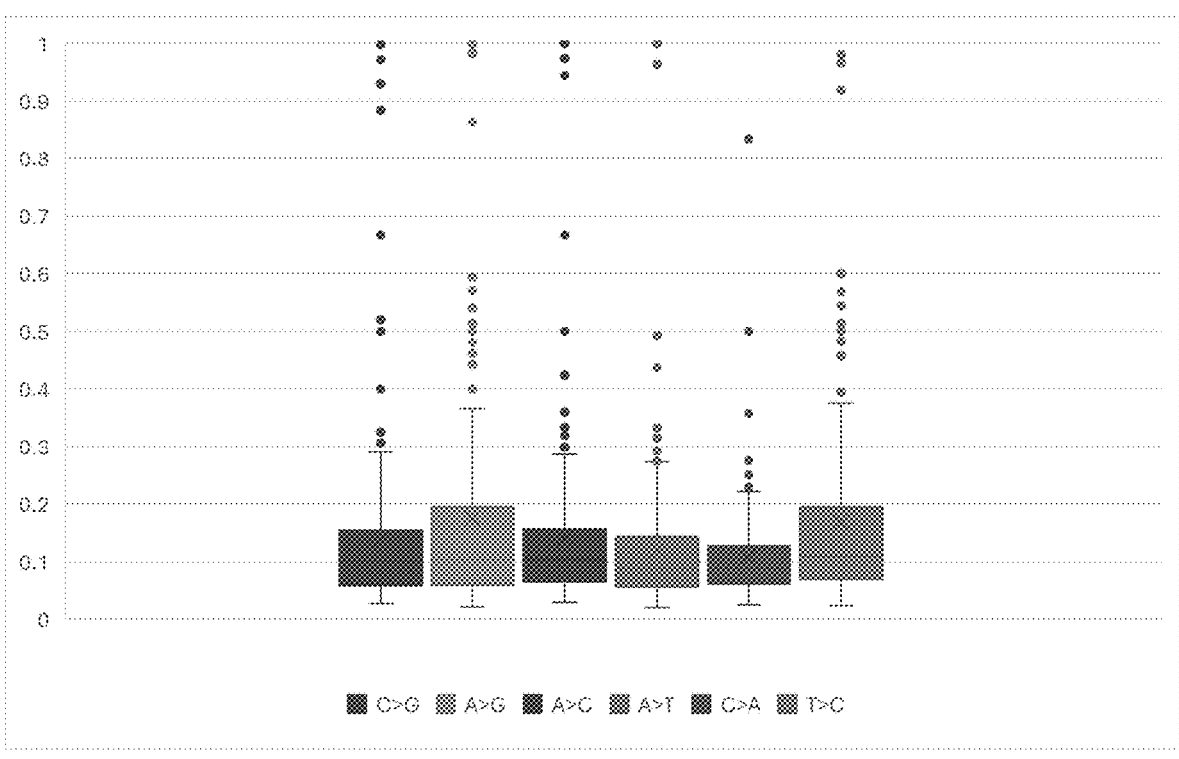
FIG. 8. Mutation AF distribution in *E. coli* DISTAL-seq adaptor ligation and sequencing methods.

Since there are a few steps during this exemplary DISTAL-seq adaptor ligation and sequencing methods library preparation that requires long incubation at elevated temperature (6 hours at 75° C. for hyperligase ligation and 1 hour at 60° C. for CirgligaseII reaction), a potential concern is on the DNA damage heat may introduce, including but not limited to C>T transition and G>T transversion (19). To address this question, DISTAL-seq adaptor ligation and sequencing methods data from the reference genomic material (*Escherichia coli* O157 (EDL 933)) is used and mutations were called from the sequencing data (see Methods). As show in FIG. 2E, all possible mutation types are at relatively comparable levels, supporting a minimal impact of heat as a source for the artifactual mutations. The allele fractions of each mutation type are shown in FIG. 8. Moreover, since UMIs are designed into both ends of the DISTAL-seq adaptor ligation and sequencing methods adaptor, further error suppression can be achieved by grouping reads with same UMIs and (FIG. 2E).

Duplex End Restoration Sequencing (DUET-Seq Adaptor Ligation and Sequencing Methods Adaptor Ligation and Sequencing Methods) and Validation Duplex sequencing uses a strategy of tagging each strand separately by distinct but corresponding UMIs so that two strands can be paired during analysis (5). Duplex sequencing has been used to detect rare genomic mutations with high positive predictive value (PPV) (5), and proven valuable in a variety of research and clinical application. As discussed earlier, with the current duplex sequencing library preparation methods, native ends are either filled in or resected to blunt ends so that they cannot be restored after the duplex is reconstructed. The principle of the DISTAL-seq adaptor ligation and sequencing methods provides a feasible framework where if strands can be paired, duplex and native end restoration sequencing (DUET-seq adaptor ligation and sequencing methods adaptor ligation and sequencing methods) may become possible.

FIG. 3A illustrates an exemplary adaptor design and preparation process for the DUET-seq adaptor ligation and sequencing methods adaptor ligation and sequencing methods. Strand-specific UMIs are complementary to each other through primer extension. A single dU base is present in the newly synthesized portion, which can later be cleaved by USER reagent (uracil DNA glycosylase and Endo VIII) enzyme and generate a blocked 3'-phosphate end (FIG. 3A). The rest of the template for the primer extension is designed so that no additional dU will be incorporated to avoid unintended USER cleavage. In addition, due to the incorporation of dU, a single dI is designed into the loop region and can be readily cleaved by endonuclease V. The 5'-end of the DUET-seq adaptor ligation and sequencing methods adaptor ligation and sequencing methods adaptor can be enzymatically phosphorylated and adenylated (FIG. 3A). Similar to DISTAL-seq adaptor ligation and sequencing methods library preparation process, since both ligations are performed at elevated temperature (75° C. for hyperligase and 60° C. for circligase), the DUET-seq adaptor ligation and sequencing methods adaptor ligation and sequencing methods adaptor is generally expected to adopt single strand form instead of stem-loop form and ligate to each strand separately.

The read structure and the strand paring diagram are also shown in FIG. 3A. Two sets of pair-end reads are considered to originate from the same duplex if their coordinates overlap by more than a heuristic threshold (150 bp used in this study) and they share the same sets of UMIs with the structure of A-B and B-A (read1 UMI-read2 UMI).

To validate DUET-seq adaptor ligation and sequencing methods adaptor ligation and sequencing methods, a mixture of DNA with known ends was used: lambda DNA (48 kb) digested with FauI (CCCGC(N)$_4$↓/GGGCG(N)$_6$↓) was spiked into lambda DNA digested with AluI (AG↓CT/ TC↓GA) at 1:2000 ratio. FauI is expected to generate 2-nt 3'-single-strand protruding ends while Alu generates blunt ends. In 50 ng of starting DNA mixture for DUET-seq adaptor ligation and sequencing methods adaptor ligation and sequencing methods, there are about $4.5 \times 10^5$ copies of FauI-digested genome equivalent in the background of $9 \times 10^8$ copies of AluI-digested genome equivalent. The theoretical diversity of the barcode combination from the DUET-seq adaptor ligation and sequencing methods adaptor ligation and sequencing methods adaptor is $4 \times 10^7$ (FIG. 3A). Thus, for FauI-digested DNA fragments, it is less likely that fragments sharing the same start and stop coordinates will be tagged with a same set of unique UMI combination. For other applications with much larger genome size, e.g., human genomic DNA, 50 ng contains about $1.39 \times 10^4$ copies of haploid genome equivalent, much less than the diversity of the barcode combination. The likelihood of the "UMI clash" is much less concerning. The goal of the validation experiment is to test whether DUET-seq adaptor ligation and sequencing methods adaptor ligation and sequencing methods can faithfully restore the FauI-digested duplex and recover the FauI cutting pattern.

Duplex sequencing is reported to be inefficient in recovering both strands and often requires excess level of sequencing (20). During DUET-seq adaptor ligation and sequencing methods adaptor ligation and sequencing methods, an extra step of exonuclease treatment can be added before the endonuclease V digestion step (FIG. 3B). Un-ligated and partially ligated products, but not fully ligated product, are substrates for Exonuclease I and III, and subject to degradation. The benefit of the exonuclease treatment is to enrich DNA with both strands fully ligated so that both strands can be sequenced and represented in the sequencing data. FIG. 3C shows the TAPESTATION automated electrophoresis system trace of the lambda DUET-seq adaptor ligation and sequencing methods adaptor ligation and sequencing methods library with and without exonuclease treatment. Sequencing was then done on these libraries, with 3.1M paired reads on the Exo-DUET-seq adaptor ligation and sequencing methods adaptor ligation and sequencing methods library (median coverage ~250×) and 2.9M paired reads on Exo+ DUET-seq adaptor ligation and sequencing methods adaptor ligation and sequencing methods library (median coverage ~250×).

Figure 9:
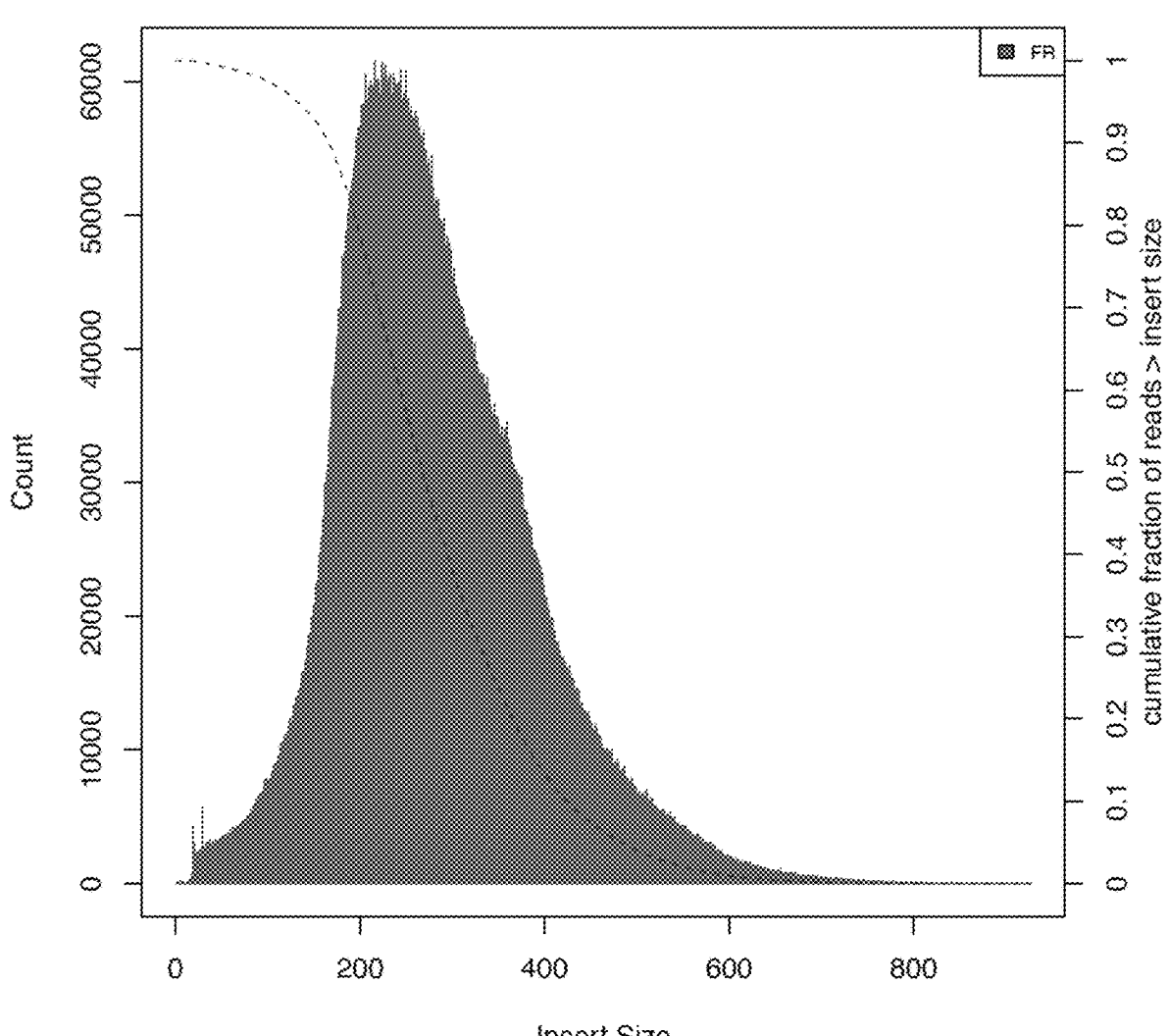
FIG. 9. Insert size distribution for sonicated gDNA DUET-seq adaptor ligation and sequencing methods adaptor ligation and sequencing methods library.
Figure 10:
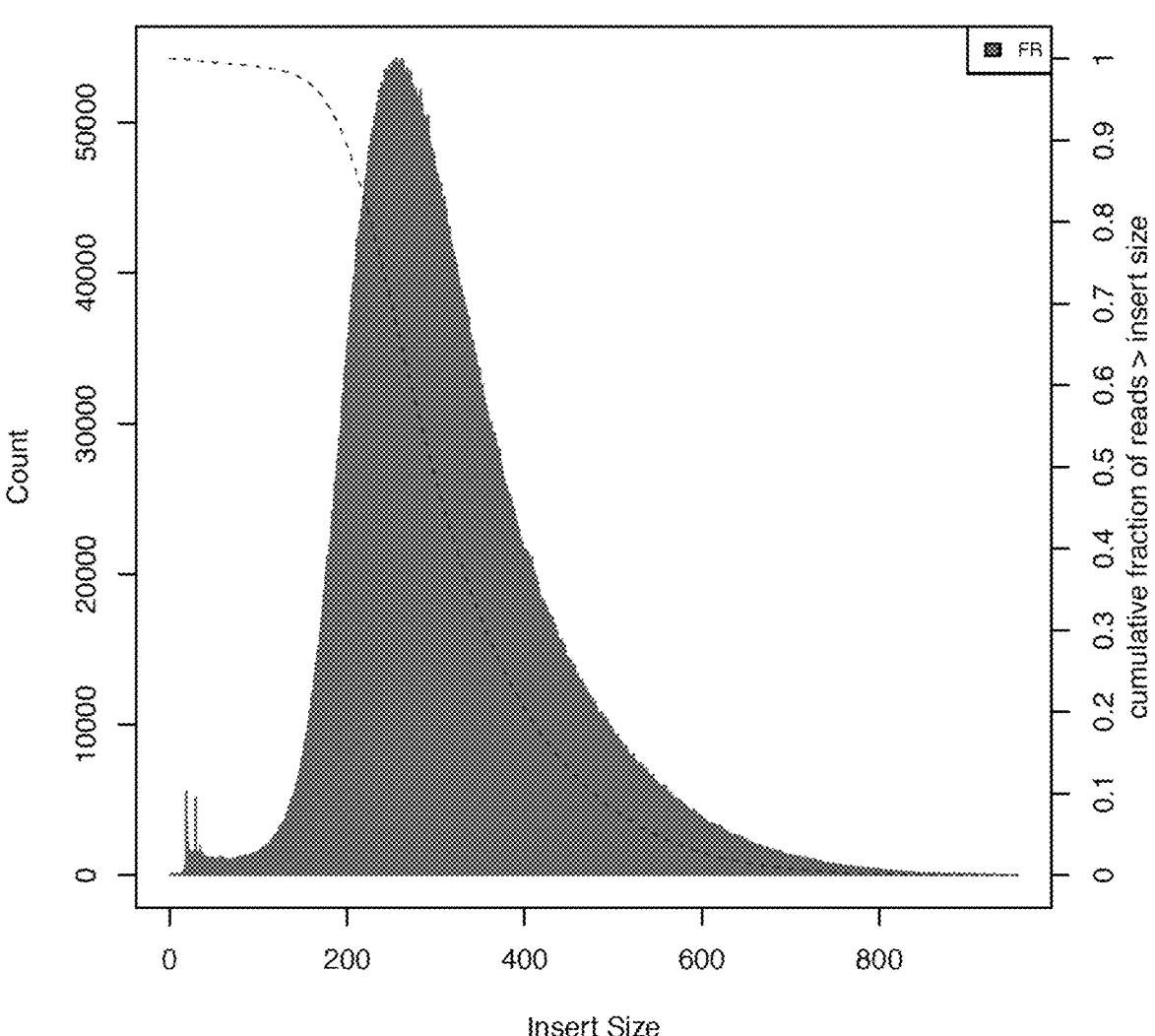
FIG. 10. Insert size distribution for enzymatically fragmented DUET-seq adaptor ligation and sequencing methods adaptor ligation and sequencing methods library.

The strand pairing analysis identified 1 duplex FauI-digested fragment from the Exo-library, as compared to 11 duplex FauI-digested fragments were, which represents about 10-fold enrichment in duplex recovery. For the duplex FauI-digested fragments identified from both libraries, both strands of the duplex originate from bona fide FauI cleavage, with no strand swapping between FauI-digested and AluI-digested strands. The signed single strand end length (FIG. 3D) shows that majority of the ends are 3'-single-strand protruding with 2-nt overhang, while a small proportion showing a 3-nt overhang. The 3-nt overhang observation is interesting in that it is known that type IIs-like restriction enzyme (FauI) may be wobbling in their cutting sites (21). Nevertheless, the relatively low sequencing depth might also contribute to a sampling bias. Overall, these results support that DUET-seq adaptor ligation and sequencing methods adaptor ligation and sequencing methods can recover duplex DNA as well as the native ends associated with the duplexes. Application of DUET-Seq Adaptor Ligation and Sequencing Methods Adaptor Ligation and Sequencing Methods to Human Genomic DNA and Cell-Free DNA Finally, this exemplary DUET-seq adaptor ligation and sequencing methods adaptor ligation and sequencing methods was applied to a few real-world samples to profile the states of the native ends. First, DUET-seq adaptor ligation and sequencing methods was used to compare the end profiles between sonicated genomic DNA and enzymatically fragmented genomic DNA. As shown in FIG. 4A, majority of the DNA fragments in sonicated genomic DNA possesses either blunt ends or ends with short single strand overhangs (2-3 nt). There is an almost equal population of ends being 5'-single-strand protruding or 3'-single-strand protruding. The enzymatically fragmented genomic DNA, however, has majority of ends being 3'-single-strand protruding, with a much wider size distribution of the single strand overhang. A major peak at −1 nt, which stands for 1-base 3'-single-strand protruding, accounts for ~10% of all the ends. The 3'-single-strand protruding nature of the ends likely reflects nucleases' preference in the fragmentase product mix. FIGS. 9 and 10 show the insert size distributions for the sonicated and enzymatically fragmented library separately, which are similar. Although both fragmentation methods are commonly used in NGS library preparation, the results here show that it is important to recognize the distinct difference in the end pattern generated by the two methods, since it may result in different levels of end-repair during ER/AT.

For cell free plasma DNA, interestingly, a first observation is that its end pattern has an intriguing resemblance to the enzymatically fragmented DNA: majority of the ends is 3'-single-strand protruding, with a major peak at −2 nt (~10%). As a quality check of the DUET-seq adaptor ligation and sequencing methods library, FIG. 4B shows the insert size distribution for the cell-free DNA library. It clearly shows the characteristic ~170 bp mono-nucleosomal major peak and the ~340 bp di-nucleosomal minor peak, consistent with previously reports (22). Sequence motif finding was attempted in the vicinity of the 5'- and 3'-ends, but yielded no significant findings (data not shown). There is also similarity in size distribution of the single strand overhang between the two types of DNA: with (min=−47 nt, max=37 nt, mean=−7.9 nt) for the cell free DNA and (min=−118 nt, max=49 nt, mean=−8.7 nt) for the enzymatically fragmented DNA. Majority of the ends has a single strand end length in the (−25,2) interval (FIG. 4B). Compared with the previous report on the end length distribution (FIG. 5A in (3)), one of the main differences is that fragments with long single strand overhang (>30 nt) is much rare in the results here.

The attachment of an adaptor with defined sequence to library DNA is crucial in driving creative ways to make sequencable libraries for the interrogation of genomic alterations. Many ligation strategies have been described including duplex to duplex ligation, such as A/T ligation, blunt-blunt ligation, etc., and single strand ligation, for example, mediated by splint or direct single strand to single strand ligation. Here, an alternative strategy is illustrated in which single strand adaptor is directly ligated to duplex DNA. It is termed DISTAL adaptor ligation methods (duplex retaining single strand tail) ligation. As shown in this example, DISTAL adaptor ligation methods enable sequencing library preparation workflows where conventional end repair is no longer necessary.

Reaction temperature plays a role in driving the efficiency of the DISTAL adaptor ligation methods, as shown in FIG. 1. It appears that hyperligase ligation occurs within a temperature window around 75° C. Lower temperature might affect the thermodynamics of DNA ends by reducing the duration of "breathing", thus reducing the accessibility of the 3'-ends. This is supported by significantly lower efficiency at 65° C. for the HyperLigase, as well as the observation that the thermostable Mth App ligase is not able to drive ligation at 65° C. On the other hand, much higher temperature may increase the likelihood of separating the entire duplex, and introduce bias to sequencing data. Indeed, when DISTAL adaptor ligation methods was performed at 80° C., DISTAL-seq adaptor ligation and sequencing methods data using *E. coli* gDNA shows higher GC bias at the high GC bins (data not shown). Other experimental techniques to lower duplex melting temperature, such as supplementing with betaine, or by using thermostable single strand binding protein etc., could be employed.

Another element for DISTAL adaptor ligation methods is the choice of thermostable ligase capable of ligating between two single strand DNA molecules. In this example, a thermostable mutant ligase with a wide range of temperature tolerance was chosen to enable hyperligase ligation (10). In addition, the mutation at the catalytic lysine in the enzyme dictates the uni-directional ligation between the 5'-adenylated end and the 3'-hydroxyl end, minimizing the chance of undesired by-product generation. Other enzymes with similar characteristics through database mining may be useful for this purpose.

Embodiments, of DISTAL adaptor ligation methods allow insights for adaptor design for the sequencing library preparation. For example, unlike the conventional Y-adaptor for which a short duplex is needed due to the substrate requirement of the T4 DNA ligase, ligations in embodiments of DISTAL-seq adaptor ligation and sequencing methods are generally completed in two separate steps, and in either step, the substrates are in the form of single strand DNA. In particular embodiments, the substrate requirement might make the duplex portion of the conventional Illumina adaptor unnecessary. This may have an added benefit of reducing adaptor length as well as adaptor dimer length, making adaptor dimer more efficiently removed by size selection.

Although designed for ligation to duplex DNA, DISTAL adaptor ligation methods workflow does not preclude single strand DNA in the starting material ligating to the adaptor. These ligated products can also go through the later steps of the library preparation, get amplified and sequenced. As such, DISTAL-seq adaptor ligation and sequencing methods and DUET-seq adaptor ligation and sequencing methods data may have captured both double and single strand DNA population in the starting material. Indeed, for the cell free plasma DNA, as shown in FIG. 4B, in addition to mono-nucleosomal and di-nucleosomal cfDNA, there are sequenced inserts within the small size range, such as less than 50 bp, which may have gone through DISTAL adaptor ligation methods workflow as single strand to single strand ligation. These inserts could exist as single strand DNA, or part of nicked double strand DNA in the starting cfDNA samples (23).

For DUET-seq adaptor ligation and sequencing methods, note that as a proof of principle, the strand-specific UMIs were designed as complementary through primer extension for the ease of synthesis (FIG. 3A). However, due to the nature of the separate ligation steps, the strand-specific UMIs do not need to be complementary. As long as there is a corresponding table to link the two distinct UMIs, the strands from the same duplex can be paired during the computational analysis. For example, one can design and synthesize multiple adaptor oligos, each with distinct 5'- and 3'-UMIs, and pool them for use in DUET-seq adaptor ligation and sequencing methods. Given the advances in high-throughput oligo synthesis, this provides another route for DUET-seq adaptor ligation and sequencing methods adaptor preparation.

Finally, since no ER/AT is used in the library prep, DISTAL-seq adaptor ligation and sequencing methods can be extended to workflows for readout of epigenetic base modifications. The dilution of epigenetic signals, especially present at the start of read 2, as observed in (3), is not expected to exist for the collected dataset. Such high-fidelity epigenomic datasets should be useful in illuminating epigenetic changes in the disease process, especially at an early onset. current examples are by sequencing genetics. When the adaptor is methylated, for example, an example of sequencing epigenome can be demonstrated.

REFERENCES

1. Gregory, et al. (2020) Characterization and mitigation of fragmentation enzyme-induced dual stranded artifacts. NAR Genom Bioinform, 2.
2. Xiong et al. (2022) Duplex-Repair enables highly accurate sequencing, despite DNA damage. Nucleic Acids Res, 50, e1-e1.
3. Jiang, et al. (2020) Detection and characterization of jagged ends of double-stranded DNA in plasma. Genome Res, 30, 1144-1153.
4. Thierry, A. R. (2023) Circulating DNA fragmentomics and cancer screening. Cell Genomics, 3, 100242.
5. Schmitt, et al. (2012) Detection of ultra-rare mutations by next-generation sequencing. Proceedings of the National Academy of Sciences, 109, 14508-14513.
6. Picelli, et al., (2014) Tn5 transposase and tagmentation procedures for massively scaled sequencing projects. Genome Res, 24, 2033-2040.
7. Gansauge, M.-T. and Meyer, M. (2013) Single-stranded DNA library preparation for the sequencing of ancient or damaged DNA. Nat Protoc, 8, 737-748.
8. Troll, et al., (2019) A ligation-based single-stranded library preparation method to analyze cell-free DNA and synthetic oligos. BMC Genomics, 20, 1023.
9. Harkins, et al., (2020) A novel NGS library preparation method to characterize native termini of fragmented DNA. Nucleic Acids Res, 48, e47-e47.
10. Zheng, Y. and Hong, M. HYPER-THERMOSTABLE LYSINE-MUTANT SSDNA/RNA LIGASES. EP3 430 154B1.
11. Bolger, A. M., Lohse, M. and Usadel, B. (2014) Trimmomatic: a flexible trimmer for Illumina sequence data. Bioinformatics, 30, 2114-2120.
12. Li, H. and Durbin, R. (2009) Fast and accurate short read alignment with Burrows-Wheeler transform. Bioinformatics, 25, 1754-60.
13. Li, et al., (2009) The Sequence Alignment/Map format and SAMtools. Bioinformatics, 25, 2078-2079.
14. GitHub-Broad Institute/picard.
15. GitHub-fulcrumgenomics/fgbio.
16. Zillig, et al. (1990) *Hyperthermus butylicus*, a hyper-thermophilic sulfur-reducing archaebacterium that ferments peptides. J Bacteriol, 172, 3959-3965.
17. Zhelkovsky, A. M. and McReynolds, L. A. (2012) Structure-function analysis of *Methanobacterium* thermoautotrophicum RNA ligase-engineering a thermostable ATP independent enzyme. BMC Mol Biol, 13, 24.
18. Phelps, et al., (2013) Single-molecule FRET and linear dichroism studies of DNA breathing and helicase binding at replication fork junctions. Proceedings of the National Academy of Sciences, 110, 17320-17325.
19. Costello, et al. (2013) Discovery and characterization of artifactual mutations in deep coverage targeted capture sequencing data due to oxidative DNA damage during sample preparation. Nucleic Acids Res, 41, e67-e67.

20. Bae, et al. (2023) Single duplex DNA sequencing with CODEC detects mutations with high sensitivity. Nat Genet, 55, 871-879.
21. Zheng, et al., (2010) A unique family of Mrr-like modification-dependent restriction endonucleases. Nucleic Acids Res, 38, 5527-5534.
22. Jiang, et al. (2015) Lengthening and shortening of plasma DNA in hepatocellular carcinoma patients. Proceedings of the National Academy of Sciences, 112.
23. Snyder, et al., (2016) Cell-free DNA Comprises an In Vivo Nucleosome Footprint that Informs Its Tissues-Of-Origin. Cell, 164, 57-68.
24. Lanman, et al. (2015) Analytical and Clinical Validation of a Digital Sequencing Panel for Quantitative, Highly Accurate Evaluation of Cell-Free Circulating Tumor DNA. PLOS One, 10, e0140712.
25. Tanaka, N. and Shuman, S. (2011) RtcB Is the RNA Ligase Component of an *Escherichia coli* RNA Repair Operon. Journal of Biological Chemistry, 286, 7727-7731.
26. Das, et al., (2013) Rewriting the rules for end joining via enzymatic splicing of DNA 3-PO 4 and 5-OH ends. Proceedings of the National Academy of Sciences, 110, 20437-20442.

27. Duan, et al., (2019) Purification and enzymatic characterization of the RNA ligase RTCB from *Thermus thermophilus*. Biotechnol Lett, 41, 1051-1057.
28. Desai, et al., (2015) Coevolution of RtcB and Archease created a multiple-turnover RNA ligase. RNA, 21, 1866-1872.
29. U.S. Pat. Pub. 2022/0356467.
30. Jacewicz A., et al (2022) Structures of RNA ligase RtcB in complexes with divalent cations and GTP, RNA, 28 (11): 1509-1518

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

---

I claim:

1. A kit comprising:

a) a plurality of single-stranded adaptors, wherein each of said single-stranded adaptors comprises: i) a nucleic acid sequence comprising a 5' end and a 3' end and ii) a 3' end blocking group attached to said 3' end of said nucleic acid sequence, wherein said 3' end blocking group is a phosphate group, wherein said 5' end of said nucleic acid sequence is adenylated, and wherein said nucleic acid sequence further comprises: a 5' region, a 3' region, and a cleavable region between said 5' and 3' regions, wherein said cleavable region comprise a nucleic acid backbone linkage, and is optionally methylated at every, or nearly every, cytosine present in said nucleic acid sequence;

b) a single strand ligase that is a thermostable lysine-mutant ssDNA/RNA ligase which is a mutated version of a precursor thermostable ssDNA/RNA ligase that has a Motif I EKx(D/N/H)G, wherein said thermostable lysine-mutant replaces lysine (K) in said Motif I with an amino acid selected from alanine (A), serine(S), cysteine (C), valine (V), threonine (T), and Glycine (G), and wherein replacement of said lysine (K) in said Motif I results in said thermostable lysine-mutant ssDNA/RNA ligase to have step 3 ligase activity, but not step 2 adenylyl transfer activity that is present in said precursor thermostable ssDNA/RNA ligase.

2. The kit claim 1, wherein said amino acid is said alanine (A).

3. The kit of claim 1, wherein said single strand ligase has an amino acid sequence that is 95% or 100% identical to SEQ ID NOs: 6.

4. The kit of claim 1, wherein said 3' region of said first nucleic acid sequence comprises a read 1 primer binding sequence, and wherein said 5' region of said first nucleic acid sequence comprises a read 2 primer binding sequence.

5. The kit of claim 1, wherein said 5' and 3' regions of said first nucleic acid sequence each comprise a barcode sequence that have a predefined relationship to each other, wherein said barcode sequences are non-complementary to each other.

6. The kit of claim 1, further comprising a deblocking agent.

7. The kit of claim 1, further comprising a ligase enzyme selected from: Circligase I, Circligase II, RtcB ligase from E. coli, or homologs, thermostable RtcB or homologs, TS2126 RNA ligase, and Mth DNA ligase, T4 RNA ligase 1, and T4 RNA ligase 2.

8. The kit of claim 1, further comprising one or more enzymes capable of cleaving said cleavable region of said nucleic acid sequence.

9. The kit of claim 8, wherein said one more enzymes, or reagent, are selected from: an endonuclease, endonuclease V, endonuclease VIII, an endonuclease and uracil DNA glycosylase, and thermostable oxoguanine glycosylase (OGG), and iodine.

10. The kit of claim 1, further comprising a plurality of DNA duplex molecules, wherein each of said DNA duplex molecule comprise: i) a first duplex end that comprises a 3' strand end and a 5' strand end, and has a 3' or 5' single-strand protruding end that is either a single non-adenine nucleotide or is at least two nucleotides in length, and ii) a second duplex end that comprises a 3' strand end and a 5' strand end which optionally has a 3' or 5' single-strand protruding or blunt end, and optionally wherein any of, or all of, said protruding ends comprise at least one cytosine that is methylated.

11. The kit of claim 10, wherein each of said DNA duplex molecules comprises a loop-like structure on the first duplex end and second duplex end, wherein said loop-like structure is composed of said nucleic acid sequence.

12. The kit of claim 1, further comprising one or more containers for collectively or separately holding the recited components, optionally, wherein said components are present inside said container.

13. The kit of claim 12, wherein said one or more containers is selected from a cardboard box, a plastic bag or box, glass vials, and plastic vials.

14. A kit comprising:

a) a plurality of single-stranded adaptors, wherein each of said single-stranded adaptors comprises: i) a nucleic acid sequence comprising a 5' end and a 3' end and ii) optionally a 3' end blocking group attached to said 3' end of said nucleic acid sequence, wherein said 3' end blocking group is optionally a modified non-canonical nucleotide or a phosphate group, wherein said 5' end of said nucleic acid sequence is adenylated, and wherein said nucleic acid sequence further comprises: a 5' region, a 3' region, and a cleavable region between said 5' and 3' regions, wherein said cleavable region comprise a nucleic acid backbone linkage, and is optionally methylated at every, or nearly every, cytosine present in said nucleic acid sequence;

b) a single strand ligase that is a thermostable lysine-mutant ssDNA/RNA ligase which is a mutated version of a precursor thermostable ssDNA/RNA ligase that has a Motif I EKx(D/N/H)G, wherein said thermostable lysine-mutant replaces lysine (K) in said Motif I with an amino acid selected from alanine (A), serine(S), cysteine (C), valine (V), threonine (T), and Glycine (G), and wherein replacement of said lysine (K) in said Motif I results in said thermostable lysine-mutant ssDNA/RNA ligase to have step 3 ligase activity, but not step 2 adenylyl transfer activity that is present in said precursor thermostable ssDNA/RNA ligase, and c) an RtcB enzyme.

15. The kit of claim 14, wherein said amino acid is said alanine (A).

16. The kit of claim 14, wherein said 3' region of said first nucleic acid sequence comprises a read 1 primer binding sequence, and wherein said 5' region of said first nucleic acid sequence comprises a read 2 primer binding sequence.

17. The kit of claim 14, wherein said 5' and 3' regions of said first nucleic acid sequence each comprise a barcode sequence that have a predefined relationship to each other, wherein said barcode sequences are non-complementary to each other.

* * * * *

SEQUENCE LISTING

```
Sequence total quantity: 63
SEQ ID NO: 1              moltype = AA  length = 380
FEATURE                  Location/Qualifiers
source                   1..380
                         mol_type = protein
                         organism = Synthetic construct
VARIANT                  92
                         note = X is any amino acid except K
SEQUENCE: 1
MVSSYFRNLL LKLGLPEERL EVLEGKGALA EDEFEGIRYV RFRDSARNFR RGTVVFETGE  60
AVLGFPHIKR VVQLENGIRR VFKNKPFYVE EXVDGYNVRV VKVKDKILAI TRGGFVCPFT  120
TERIEDFVNF DFFKDYPNLV LVGEMAGPES PYLVEGPPYV KEDIEFFLFD IQEKGTGRSL  180
PAEERYRLAE EYGIPQVERF GLYDSSKVGE LKELIEWLSE EKREGIVMKS PDMRRIAKYV  240
TPYANINDIK IGSHIFFDLP HGYFMGRIKR LAFYLAENHV RGEEFENYAK ALGTALLRPF  300
VESIHEVANG GEVDETFTVR VKNITTAHKM VTHFERLGVK IHIEDIEDLG NGYWRITFKR  360
VYPDATREIR ELWNGLAFVD                                            380

SEQ ID NO: 2              moltype = AA  length = 379
FEATURE                  Location/Qualifiers
source                   1..379
                         mol_type = protein
                         organism = Synthetic construct
VARIANT                  92
                         note = X is any amino acid except K
SEQUENCE: 2
MVSSHFKEIL MRLGLPEDRI EVLEAKGGIT EEEFDGIRYL RFKDSARGLR RGTVVFDEAN  60
VILGFPHIKR VVSLRAGVMR IFKRTPFYVE EXVDGYNVRV ALVSDRVLAI TRGGFVCPFT  120
TERILDFVPE EFFKDYPHLV LVGEMAGPES PYLVEGPPYV EEDIRFFLFD IQEKGTGKSL  180
PVQERLKLAE EYGIPHVKVF GLYTVDRIED LYDLIERLSR EGREGVVMKS PDMKRVVKYV  240
TPFANVNDVK IGAKVFFELP PGYFMSRIMR LAFYVAERRI KGERFEELAR NLGKALLEPF  300
VESIWDVEQG DEIAEVFRIR VKRIETAYKM VTHFERLGLN IKIEDIEEVG GMWRITFKRA  360
YDEATREIRE LIGGRAFVD                                             379

SEQ ID NO: 3              moltype = AA  length = 379
FEATURE                  Location/Qualifiers
source                   1..379
                         mol_type = protein
                         organism = Synthetic construct
VARIANT                  92
                         note = X is any amino acid except K
SEQUENCE: 3
MVSSKFKDIL YRLGIPEGKV EDLEARGGLV EDKFDDIKYL RIRNSVGKLR RGTVVLNDKF  60
IILGFPHIKR IVNLKNGIKR TFKRGEFYVE EXVDGYNVRV VKFRGKXLGI TRGGFICPFT  120
TERISDFIPE EFFKDHPNLI LVGEMAGPES PYLVEGPPYV KEDIQFFLFD IQELGTGRSL  180
PVEERLKIAE EYGISHVEVF GKFTYKDLEE IYEIVERLSR EGREGIVMKS PDMRKMVKYV  240
TPYANINDIK IGARVFYELP PGYFTSRISR LAFYIAEKRL RGENFEELAK ELGKALLQPL  300
VESIHDVEQE DEIAEVFKVR VKKIETAYKM VTHFEKLGLR IEIVDIEEMK GGWRITFKRL  360
YPDATEEIRE LIGGKSFVD                                             379
```

```
SEQ ID NO: 4               moltype = AA   length = 382
FEATURE                    Location/Qualifiers
source                     1..382
                           mol_type = protein
                           organism = Synthetic construct
VARIANT                    95
                           note = X is any amino acid except K
SEQUENCE: 4
MKEVVSSVYK EILVKLGLTE DRIETLEMKG GIIEDEFDGI RYVRFKDSAG KLRRGTVVID     60
EEYVIPGFPH IKRIINLRSG IRRIFKRGEF YVEEXVDGYN VRVVMYKGKM LGITRGGFIC    120
PFTTERIPDF VPQEFFKDNP NLILVGEMAG PESPYLVEGP PYVKEDIQFF LFDVQEIKTG    180
RSLPVEERLK IAEEYGINHV EVFGKYTKDD VDELYQLIER LSKEGREGII MKSPDMKKIV    240
KYVTPYANIN DIKIGARVFY ELPPGYFTSR ISRLAFYLAE KRIKGEEFER VAKELGSALL    300
QPFVESIFDV EQEEDIHELF KVRVKRIETA YKMVTHFEKL GLKIEIVDIE EIKDGWRITF    360
KRLYPDATNE IRELIGGKAF VD                                            382

SEQ ID NO: 5               moltype = AA   length = 382
FEATURE                    Location/Qualifiers
source                     1..382
                           mol_type = protein
                           organism = Synthetic construct
VARIANT                    95
                           note = X is any amino acid except K
SEQUENCE: 5
MENMVSSKFK ELLYTLGIPE DKVEILEARG GIMEDEFEGI RYLRFKNSVG KLRRGTVLFE     60
DGTTVFGFPH IKRIVNLSAG VRKIFKSSEF YVEEXVDGYN VRVVKFKDRI LGITRGGFIC    120
PYTTERIAEF VPEEFFKDHK DLVLVGEMAG PESPYLVEGP PYVKEDIQFF LFDIQDIKTG    180
SSLPVEERLK LAEEYGINHV EVFGRYSYKD IDDLYELIER LSREGREGIV MKSPDMKKIV    240
KYVTPYANIN DIKIGARVFY ELPGGYFTSR ISRLAFYIAE KKIRGEELHN LALQLGKALL    300
QPLVEAIHDV TQGDVIAERF RVRVRKIETA YKMVTHFEKL GLEIEIEDIE EIEGGWRVTF    360
KRVYPEATRE IRDLIGGKAF VD                                            382

SEQ ID NO: 6               moltype = AA   length = 390
FEATURE                    Location/Qualifiers
source                     1..390
                           mol_type = protein
                           organism = Synthetic construct
VARIANT                    100
                           note = X is any amino acid except K
SEQUENCE: 6
MTWIKNPEPW MVNLVAEKLG LDVERVETLA RHGTIRFRGY RDVVYALLRR EIAGHPEGTV     60
VLLERNGARL VPGYPPIQRM VLPTIALPRH FIDKVVVEEX MNGYNVRLVM FHRKLLAVTR    120
GGFICPYTTA RLERLIGGRV RELFREIDPE TYTIAGEVVG LENPYTRYFY PEAPRFDYFV    180
FDLFHELKPL PPLERNELLE KYGLKHVRLL GVIDKNDVEM FKQIVAELDR EGREGVVAKD    240
PEYRVPPLKY TTSAVNIGDV RYGMRFFMEE GRSFLFSRLL RELFRAYEEG FGDAQLEKLA    300
LEFGRAATEP ALESIRKVAM GDMLYEEFEL VFADEVELEE FTSYMAELGV DIVVVSTSRE    360
DEGLRARMRK IKDTWIQLRK VLDTGLSPVD                                    390

SEQ ID NO: 7               moltype = AA   length = 390
FEATURE                    Location/Qualifiers
source                     1..390
                           mol_type = protein
                           organism = Synthetic construct
SEQUENCE: 7
MTWIKNPEPW MVNLVAEKLG LDVERVETLA RHGTIRFRGY RDVVYALLRR EIAGHPEGTV     60
VLLERNGARL VPGYPPIQRM VLPTIALPRH FIDKVVVEEA MNGYNVRLVM FHRKLLAVTR    120
GGFICPYTTA RLERLIGGRV RELFREIDPE TYTIAGEVVG LENPYTRYFY PEAPRFDYFV    180
FDLFHELKPL PPLERNELLE KYGLKHVRLL GVIDKNDVEM FKQIVAELDR EGREGVVAKD    240
PEYRVPPLKY TTSAVNIGDV RYGMRFFMEE GRSFLFSRLL RELFRAYEEG FGDAQLEKLA    300
LEFGRAATEP ALESIRKVAM GDMLYEEFEL VFADEVELEE FTSYMAELGV DIVVVSTSRE    360
DEGLRARMRK IKDTWIQLRK VLDTGLSPVD                                    390

SEQ ID NO: 8               moltype = AA   length = 385
FEATURE                    Location/Qualifiers
source                     1..385
                           mol_type = protein
                           organism = Synthetic construct
VARIANT                    99
                           note = X is any amino acid except K
SEQUENCE: 8
MASAAEVLAS ALRAVGVDPG SVDLEALSTR RSVRVSRFED VVYVGFRRQF RGVPEGTLVA     60
FRRGEQIVVW GYPSIKRMLL PRVAVPRWFP GPTVLVEEXM NGYNVRVFTL GGMVYAATRG    120
GLICPYTTRR LRRLYGGALQ KILEDLGAEG SFIAGEVVGL ENPYTRYYYE EAPGFGYFIF    180
DIFKGGRQLP PRVKFSLAPE YGLKTVNLLA EIPATASGVE RLYTIVEDLE KRGREGVIVK    240
DPEGRVEPLK YTTSRTNIGD IRLGMRYPFE EGRSFLFPRI LREIFREWET GRRRYGELGE    300
AILAPAIEAV EAVSRGGRLV EEFELVFANE VEAEEVIAYF ASLGVHLEIA GVARGVDGVR    360
VAFRKPRKSE GEIARILETG ISPLD                                         385
```

```
SEQ ID NO: 9                  moltype = AA   length = 381
FEATURE                       Location/Qualifiers
source                        1..381
                              mol_type = protein
                              organism = Synthetic construct
VARIANT                       92
                              note = X is any amino acid except K
SEQUENCE: 9
MDENELVNKL SDALGIEYEK LSKHIGRSIR LMKYGELNYV VFRRDLLGYR EGTTILLGEE  60
PLIVHGYPSI QRLAFIEGVS KHMIDNVVVE EXMNGYNVRV VYYMNNIYAI TRGGYICPYT  120
TARIRKLYSK NIKLAYQEYP DTILVGEVVG TENPYVIYDY PEARGFDYFI FDTMKKDKLQ  180
PLRIRDEIAE KYSLKTVRIL DIINKRDIDR LKTIINRLEK ERREGVVLKD PYQRVPPLKY  240
TTIYINIRDI WEGMRYPFDE GRGYLFSRIV RLIAQGYEYD WNNTELDRIA LKLGRAILEP  300
AINSLKKRAN GEIIASKYTL VFPSEDDLSK YIEYAESIGM DFIFRVVEKR EDGCIVVELF  360
KMKETHNIYT KMLKTGYSPL D                                            381

SEQ ID NO: 10                 moltype = AA   length = 390
FEATURE                       Location/Qualifiers
source                        1..390
                              mol_type = protein
                              organism = Synthetic construct
VARIANT                       100
                              note = X is any amino acid except K
SEQUENCE: 10
MIRIPLERWM IEKLAEALNV NIEEAERLAR RRNVVRLMKW RNVTYFSLRK DVYGLREGTL  60
IAVWPDGYRV VPGYPSIQRV LLPSVALPKH FIDKIVVEEX LNGYNVRVVK LRDEIVAVTR  120
GGLICPYTTQ RIRKLYGDKL TSLFREEGEE LVVAGEVIGL ENPYVRFYYP EAGGFAYFIF  180
DIVHGEKFLP PHERKEIVEK HGLLHVPVLG EIDKNDIKAF RKIIEDLERR GREGVVLKDP  240
EYRVPPLKYT TSFININHDIE IGMRFPFDEG RNYLFSRILR EIFKAVEEGW DDRRLLLAEQ  300
NLGKAILEPA IEAVKEVKNG KMLYEEFMLP FDTRDDFEEF LDYMASLGVD IIVAGVEQRS  360
DGSIVARIRK VKDTWREVQK ILETGLSPID                                   390

SEQ ID NO: 11                 moltype = AA   length = 367
FEATURE                       Location/Qualifiers
source                        1..367
                              mol_type = protein
                              organism = Synthetic construct
VARIANT                       77
                              note = X is any amino acid except K
SEQUENCE: 11
MISPELVKEA LKKKKVRSEE AFGLEYLRFN DDYKDIPRGT AIFKDFIIWG YPHIGRIFLL  60
ETGLREQFEA PFWVEEXVDG YNTRIFKYGD NYYALSRGGF ICPFTTDRLP DLIDLRILDE  120
NPDLVICAEV AGPENPYIEE SPPYVKEDVQ LFVFDFMKKN EQGFLSQEEK MELIEKYNLP  180
HVEILGRFTA SEEGIKKIKE ILKRFNEEGR EGVVFKEDSE RNKRAKYITS YANLMDIKTN  240
AKNMLQLPPE YYTNRILRLV LFMYEEGLKT TEHLYEELGR AFIDGLFQAI EQFEKEHKVY  300
KTFTCKFRKK ENAIALLELL SKTSKHIQVK ERRLEKEGDY WRLEFDKVFL NMTGLLGHLL  360
SGGIVYD                                                            367

SEQ ID NO: 12                 moltype = AA   length = 390
FEATURE                       Location/Qualifiers
source                        1..390
                              mol_type = protein
                              organism = Synthetic construct
VARIANT                       100
                              note = X is any amino acid except K
SEQUENCE: 12
MTWIHSPESW MLDVVAEALG IDRERVEHLA RHRTIRYRVF RGILYASLRR EVAGHPEGTV  60
IVFGRGWWRL IPGYPSIQRM VLPSVALPRH FVDKIVVEEX LNGYNVRVAL IDDRIIAVTR  120
GGFICPYTTS RLERIMGNQL KDMLRELGPE EHVAAGEVIG LENPYTRYFY PEAPRFGYFV  180
FDVFREGKPL PPGWRDEVTE KHGVPHVPVL GVLDKNDIEG FKKIVERLNQ EGREGVIVKD  240
PEYRVPPLKY TTPATNIGDI RYGMRFFMEE GRGFLFSRLL REIFRVYEEG LTGPRLDALA  300
LELGRAALQP AIETVKKVAA GDMVYEEFEL EFASRSELEE FMDYMQGLGV DLVLVEIREE  360
NGLLKTRIRK MKETWLQVRK MLETGLTPID                                   390

SEQ ID NO: 13                 moltype = AA   length = 388
FEATURE                       Location/Qualifiers
source                        1..388
                              mol_type = protein
                              organism = Synthetic construct
VARIANT                       101
                              note = X is any amino acid except K
SEQUENCE: 13
MRRDVSQFAN KLDIGKVSEL LDIPEHRITG ALKRKTIQYV WGKKELFRFD KPVSSIEGGT  60
SVFTEPFDIV RGFPKISRTL MLSPALQKHF SSCRKVAVEE XMNGYNVRVA LIGDALVALT  120
RGGFICPYTT EKAIDLIGYD FFNDHPDLVL CGEMVGPDSP YVPKTFYDIE SLDFFVFDIR  180
EKITGKPLSV MERRALVDKY GIKSVRLFGE FEIGETHSEI TRIIKDLGGS QHEGVVIKDP  240
QMVVPPMKYT SSESNCADLR YAFEFYNDFG RDFFFGRVCR EAFQSVEWDE DEESVEKRCR  300
QLGESLLLPM IKTIKKKKDG ERIAENVQIR VKSLDTVKEF EEYLKLVGVD AVFEEPEQTG  360
NEYFVRIRKM HQSTNDRTEA ILGGQLWS                                     388
```

-continued

```
SEQ ID NO: 14                 moltype = AA   length = 390
FEATURE                       Location/Qualifiers
source                        1..390
                              mol_type = protein
                              organism = Synthetic construct
VARIANT                       100
                              note = X is any amino acid except K
SEQUENCE: 14
MTWIHRPEPW MLDVVADALG LPRERVEELA SRRTLRFREF RGLLYASLRR GVAGHHEGTA    60
VVFGRGWWRV VPGYPPIQRM VLPSVALPRH FLDRVVVEEX LNGYNVRVVL VDDRILAVTR   120
GGLICPYTTS RLERLMGDRL REMLRELGPE DHVAAGEVIG LENPYTRYFY PEAPRFGYFV   180
FDIFRGGRPL PPRMRDEAAE KHGVPHVPVL GVLEKTDVEA FKRIVERLDR EGREGVVVKD   240
PDYRVPPLKY TTSSTNIGDI RLGMRFFMEE GWSFLFSRIL REIFRVYEEG VEGPRLDAIA   300
LELGRAALQP AVETVKKVAG GYMVYEEFEL EFAGRDELEE FMDYMQSLGV DVVLVEAREE   360
GGVLRARMRK IKETWIRVRR ILETGVSPID                                   390

SEQ ID NO: 15                 moltype = AA   length = 389
FEATURE                       Location/Qualifiers
source                        1..389
                              mol_type = protein
                              organism = Synthetic construct
VARIANT                       99
                              note = X is any amino acid except K
SEQUENCE: 15
MGWVQPEPWM VDAVAEALGL ERERVESLAK HRTIRFRVFR GILYASLRRE LGGYPEGTVV    60
IFGRGWSRVV HGYPPIQRMV LPSVALPRHF VDRIVVEEXL NGYNVRVVLV DGRLLAVTRG   120
GFICPYTTDR IERLLGGRLR EMLRELGEEE HVAAGEVIGL ENPYTRYYYP EAPRFGYFVF   180
DIFRSGKPLP PRVRDEATEK HGVPHVPVLG VLDKGDIEGF RSIVEALERR GREGVVVKDP   240
EYRVHPLKYT THATNVGDIR LGMRFFMEEG RGFLFSRLLR EIFRAYEQGL QGPRLEKLAT   300
EIGLAALEPA LETVRLVAAG EPVYEEFELE FENRDRLEEF LEYMQSLGVD VVVAGTYERD   360
GMLVARVRKM RDTWLQVRRM LETGLTPID                                    389

SEQ ID NO: 16                 moltype = AA   length = 380
FEATURE                       Location/Qualifiers
source                        1..380
                              mol_type = protein
                              organism = Synthetic construct
VARIANT                       94
                              note = X is any amino acid except K
SEQUENCE: 16
MFVSESLGLS KHLGETLEER KILREALISH SFFSDVIEAV RFDKKFGEIE EGTVVAKTIN    60
GVRIVRGFPK IKRALVLNPT LKKHFENEVA VEEXMNGYNV RIARFGKNLY AMTRRGIICP   120
YTTEKARELI NPEFFKDHSD LVLCCEAVGE ESPYVPKSMY GVEGLDFFVF DIREERTNRP   180
LPVEEKLRLC EEYGLRHATY FGTYDVDVAH DEIKDIISDL AGKGREGVVI KDPEMKLSPL   240
KYTTSQTNAE DLKYAFRFFN DYGKDFMFSR IVREGFQSFE FNEGDKEFRE RCLRLGMAIL   300
KPMVESIREV ALGGKVSEKL RLRFGSLDVM NLFFEQWKRS KVDFEITDIK KDGKDIVVFV   360
NKTMRNTTDK IKAHLEGIPW                                             380

SEQ ID NO: 17                 moltype = AA   length = 380
FEATURE                       Location/Qualifiers
source                        1..380
                              mol_type = protein
                              organism = Synthetic construct
VARIANT                       95
                              note = X is any amino acid except K
SEQUENCE: 17
MKFIAEALGV SQAVIEKLNE KNLIRLAFIK HPFFRDVIEA YKLERKVGEF EPGTLIAKTV    60
EGLRVVRGYP KIKRALTLYP TIKKHFKGEV VLEEXMNGYN VRLVKFGENI YAITRGGFIC   120
PYTTEKARRL VNLDFFKDNP KLMLCCEAVG EESPFVPKDV YGVKTIDFYV FDIRDQKTNI   180
ALPIKQKEKL AEEYGLKLAP ILAEVQVSKA HEIAKEIILE LDKRGREGIV IKDPMMRRPP   240
IKYTTSQCNC SDLSYAFRFF EEYGKDFMFS RIIREAFQSF EFRENEEKFK DRCLRLGEAI   300
LSMVKSIKEV NEGKRIVEKM RLRFYDLEIF ELFKEHIRRM GIRAEFSNPK REEDGYVVWV   360
YRHIMSTTDK IKYILAGNLY                                             380

SEQ ID NO: 18                 moltype = AA   length = 380
FEATURE                       Location/Qualifiers
source                        1..380
                              mol_type = protein
                              organism = Synthetic construct
VARIANT                       92
                              note = X is any amino acid except K
SEQUENCE: 18
MVSSHFKSLL LELGISRERI EILESKGGIV EDEFEGIRYL RFKDSAGSLR RGTVVFDSHN    60
IILGFPHIKR VVHLENGIKR VFKRKPFYVE EXVDGYNIRV AQIEGRVFAF TRGGFVCPFT   120
TERIEDFVNM EFFKDYPNLV LCGEMAGPES PYLVEGPPYV KEDIEFFLFD IQEKKTGKSL   180
TVEERLKIAE EYGIPSVEVF GVYDISKIDE LKELIEQLSR EKREGIVMKS PDMKKIVKYV   240
TPYANVNDIK IGARIFFDLP HGYFMQRIKR LAFYLAEKRV QDEEFEKYAR ALGRALLEPF   300
VESIWDVSAG EEIAEVFTVR VKHIETAYKM VSHFERLGLK IHIEDIEEMP QGYWRITFKR   360
```

-continued

```
VYPDATREIR ELWSGHAFVD                                                    380

SEQ ID NO: 19          moltype = AA   length = 379
FEATURE                Location/Qualifiers
source                 1..379
                       mol_type = protein
                       organism = Synthetic construct
VARIANT                92
                       note = X is any amino acid except K
SEQUENCE: 19
MVSSRFKDIL TSLGISEERI EILEAKGGIV EDEYEGLRYL RFKDSAGKLR RGTVVFDFDK   60
IILGFPHIKR VVNLEKGIRR IFKRGEFYVE EXVDGYNVRV TKVGERILAI TRGGFICPFT   120
TERITDFVPE EFFKDNPNLV LVGEMAGPES PYLVEGPPYV KEDIKFFLFD VQEINTGKSL   180
PVEERLKLAE EYGIPHVEVF GKYTRDDIGE LYALIEKLSE EGREGIVMKS PDMKKIVKYV   240
TPYANINDIK IGARVFYELP PGYFTSRISR LAFYIAERKI RDEELRKLAE DLGKALLQPF   300
VEGILDVEQG EEIAETFKIR VKKIETAYKM VTHFEKLGLN IEIVDIEEMD GLWRITFKRV   360
YSDATEKIKE LVGGKAFVD                                               379

SEQ ID NO: 20          moltype = AA   length = 361
FEATURE                Location/Qualifiers
source                 1..361
                       mol_type = protein
                       organism = Synthetic construct
VARIANT                67
                       note = X is any amino acid except K
SEQUENCE: 20
MKSERGIMKY KDFIYYPFKK GGFGKGSVII YHNDDVKIVP GYPSIKRLVL LSKVPEHFPE   60
GVSVEEXMNG YNVRAMIVGG DVAFITRGGY LCPYTNARLN TLYGEKVKAL LEELPPGSFL   120
AGEVVGVENP YVRVKYPEAP YFDYFIFDIF VKTEDGWRQM PVEERHEIVK RHGLRSVRLL   180
GTFESSEAPL KIKEIIDRFD KEGREGVVMK DPEYKRSPAK YTGSYTNIGD IREGMRYPFD   240
EGKDYLFPRI VREIFKVYEE GLSDKELERR ALELGMAILK PAVESLKEVA QGETLFERFV   300
LRFPHEEDLE EYLNYTRSLG VKVIVEEKWE EGEWIVVKAK KFKNTSNVYR SMLKSGQTPL   360
D                                                                 361

SEQ ID NO: 21          moltype = AA   length = 381
FEATURE                Location/Qualifiers
source                 1..381
                       mol_type = protein
                       organism = Synthetic construct
VARIANT                92
                       note = X is any amino acid except K
SEQUENCE: 21
MVSSYFKGIL LNLGLDEERI EVLENKGGIV EDEFEGMRYL RLKDSARSLR RGTVVFDEHN   60
IILGFPHIKR VVQLENGIRR AFKRKPFYVE EXVDGYNVRV AKIGEKILVF TRGGFVCPFT   120
TERIEDFITL DFFKDYPNMV LCGEMAGPES PYLVEGPPYV KEDIQFFLFD IQEKKTGRSL   180
PVEERLKLAE EYGIPSVEVF GLYDLSRIDE LHALIDRLTK EKREGIVMKS PDMKKIVKYV   240
TPYANINDIK IGARIFFDLP HGYFMQRIKR LAFYLAERKI RGEEFDEYAR ALGKVLLEPF   300
VESIWDISSG DDEIAELFTV RVKKLETAHK MVTHFERLRL KIHIDDIEVL DNGYWRITFK   360
RVYPDATKEM RELWNGHAFV D                                            381

SEQ ID NO: 22          moltype = DNA   length = 77
FEATURE                Location/Qualifiers
source                 1..77
                       mol_type = other DNA
                       organism = Synthetic construct
SEQUENCE: 22
nnnnnagatc ggaagagcac acgtctgaac tccagtcaca cactctttcc ctacacgacg   60
ctcttccgat ctnnnnn                                                77

SEQ ID NO: 23          moltype = DNA   length = 81
FEATURE                Location/Qualifiers
source                 1..81
                       mol_type = other DNA
                       organism = Synthetic construct
SEQUENCE: 23
gtcgavvvvv vvvagatcgg aagagcacac gtctgaactc cagtcactac actctttccc   60
tacacgacgc tcttccgatc t                                           81

SEQ ID NO: 24          moltype = DNA   length = 27
FEATURE                Location/Qualifiers
source                 1..27
                       mol_type = other DNA
                       organism = Synthetic construct
SEQUENCE: 24
actcttcctt tttcaatatt attgaag                                     27

SEQ ID NO: 25          moltype = DNA   length = 31
FEATURE                Location/Qualifiers
source                 1..31
```

-continued

```
                              mol_type = other DNA
                              organism = Synthetic construct
SEQUENCE: 25
acacggtgcc tgactgcgtt agcaatttaa c                                   31

SEQ ID NO: 26           moltype = DNA   length = 28
FEATURE                 Location/Qualifiers
source                  1..28
                        mol_type = other DNA
                        organism = Synthetic construct
SEQUENCE: 26
aggttaatgt catgataata atggtttc                                       28

SEQ ID NO: 27           moltype = DNA   length = 30
FEATURE                 Location/Qualifiers
source                  1..30
                        mol_type = other DNA
                        organism = Synthetic construct
SEQUENCE: 27
gggttttctt ttgtgcgctt gcaggccagc                                     30

SEQ ID NO: 28           moltype = DNA   length = 31
FEATURE                 Location/Qualifiers
source                  1..31
                        mol_type = other DNA
                        organism = Synthetic construct
SEQUENCE: 28
agcagaatgc cgtccaccat cggatcgctg g                                   31

SEQ ID NO: 29           moltype = DNA   length = 37
FEATURE                 Location/Qualifiers
source                  1..37
                        mol_type = other DNA
                        organism = Synthetic construct
SEQUENCE: 29
gggtttcctc agctcttttg tgcgcttgca ggccagc                             37

SEQ ID NO: 30           moltype = DNA   length = 38
FEATURE                 Location/Qualifiers
source                  1..38
                        mol_type = other DNA
                        organism = Synthetic construct
SEQUENCE: 30
agcagaacct cagctgccgt ccaccatcgg atcgctgg                            38

SEQ ID NO: 31           moltype = DNA   length = 37
FEATURE                 Location/Qualifiers
source                  1..37
                        mol_type = other DNA
                        organism = Synthetic construct
SEQUENCE: 31
gggttttgct gaggcttttg tgcgcttgca ggccagc                             37

SEQ ID NO: 32           moltype = DNA   length = 38
FEATURE                 Location/Qualifiers
source                  1..38
                        mol_type = other DNA
                        organism = Synthetic construct
SEQUENCE: 32
agcagaatgc tgagggccgt ccaccatcgg atcgctgg                            38

SEQ ID NO: 33           moltype =    length =
SEQUENCE: 33
000

SEQ ID NO: 34           moltype =    length =
SEQUENCE: 34
000

SEQ ID NO: 35           moltype =    length =
SEQUENCE: 35
000

SEQ ID NO: 36           moltype =    length =
SEQUENCE: 36
000

SEQ ID NO: 37           moltype =    length =
SEQUENCE: 37
```

-continued

```
000

SEQ ID NO: 38          moltype =   length =
SEQUENCE: 38
000

SEQ ID NO: 39          moltype =   length =
SEQUENCE: 39
000

SEQ ID NO: 40          moltype =   length =
SEQUENCE: 40
000

SEQ ID NO: 41          moltype =   length =
SEQUENCE: 41
000

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
000

SEQ ID NO: 51          moltype =   length =
SEQUENCE: 51
000

SEQ ID NO: 52          moltype =   length =
SEQUENCE: 52
000

SEQ ID NO: 53          moltype =   length =
SEQUENCE: 53
000

SEQ ID NO: 54          moltype = DNA  length = 68
FEATURE                Location/Qualifiers
source                 1..68
                       mol_type = other DNA
                       organism = Synthetic construct
modified_base          35
                       mod_base = OTHER
                       note = Uracil
SEQUENCE: 54
agatcggaag agcacacgtc tgaactccag tcactacact ctttccctac acgacgctct    60
tccgatct                                                              68

SEQ ID NO: 55          moltype = DNA  length = 78
```

```
FEATURE              Location/Qualifiers
source               1..78
                     mol_type = other DNA
                     organism = Synthetic construct
modified_base        40
                     mod_base = OTHER
                     note = Uracil
SEQUENCE: 55
nnnnnagatc ggaagagcac acgtctgaac tccagtcact acactctttc cctacacgac   60
gctcttccga tctnnnnn                                                 78

SEQ ID NO: 56        moltype = DNA   length = 34
FEATURE              Location/Qualifiers
source               1..34
                     mol_type = other DNA
                     organism = Synthetic construct
SEQUENCE: 56
agatcggaag agcacacgtc tgaactccag tcac                               34

SEQ ID NO: 57        moltype = DNA   length = 33
FEATURE              Location/Qualifiers
source               1..33
                     mol_type = other DNA
                     organism = Synthetic construct
SEQUENCE: 57
acactctttc cctacacgac gctcttccga tct                                33

SEQ ID NO: 58        moltype = DNA   length = 121
FEATURE              Location/Qualifiers
source               1..121
                     mol_type = other DNA
                     organism = Synthetic construct
modified_base        59
                     mod_base = OTHER
                     note = Uracil
SEQUENCE: 58
agatcggaag agcacacgtc tgaactccag tcacatctcg tatgccgtct tctgcttgta   60
atgatacggc gaccaccgag atctacacac actctttccc tacacgacgc tcttccgatc  120
t                                                                  121

SEQ ID NO: 59        moltype = DNA   length = 24
FEATURE              Location/Qualifiers
source               1..24
                     mol_type = other DNA
                     organism = Synthetic construct
SEQUENCE: 59
atctcgtatg ccgtcttctg cttg                                          24

SEQ ID NO: 60        moltype = DNA   length = 29
FEATURE              Location/Qualifiers
source               1..29
                     mol_type = other DNA
                     organism = Synthetic construct
SEQUENCE: 60
aatgatacgg cgaccaccga gatctacac                                     29

SEQ ID NO: 61        moltype = DNA   length = 137
FEATURE              Location/Qualifiers
source               1..137
                     mol_type = other DNA
                     organism = Synthetic construct
modified_base        67
                     mod_base = OTHER
                     note = Uracil
SEQUENCE: 61
agatcggaag agcacacgtc tgaactccag tcacacgatc agatctcgta tgccgtcttc   60
tgcttgtaat gatacggcga ccaccgagat ctacacatat gcgcacactc tttccctaca  120
cgacgctctt ccgatct                                                 137

SEQ ID NO: 62        moltype =   length =
SEQUENCE: 62
000

SEQ ID NO: 63        moltype =   length =
SEQUENCE: 63
000
```